United States Patent
Mercier et al.

(10) Patent No.: US 12,006,316 B2
(45) Date of Patent: *Jun. 11, 2024

(54) 9H-PYRROLO-DIPYRIDINE DERIVATIVES

(71) Applicant: UCB Biopharma SPRL, Brussels (BE)

(72) Inventors: Joel Mercier, Brussels (BE); Laurent Provins, Brussels (BE); Celine Vermeiren, Brussels (BE); Yogesh Anil Sabnis, Brussels (BE)

(73) Assignee: UCB BIOPHARMA SRL, Brussels (BE)

( * ) Notice: Subject to any disclaimer, the term of this patent is extended or adjusted under 35 U.S.C. 154(b) by 145 days.

This patent is subject to a terminal disclaimer.

(21) Appl. No.: 17/700,075

(22) Filed: Mar. 21, 2022

(65) Prior Publication Data

US 2022/0213103 A1    Jul. 7, 2022

Related U.S. Application Data

(63) Continuation of application No. 16/749,537, filed on Jan. 22, 2020, now Pat. No. 11,312,716, which is a continuation of application No. 15/547,980, filed as application No. PCT/EP2016/051993 on Jan. 29, 2016, now abandoned.

(30) Foreign Application Priority Data

Feb. 2, 2015   (EP) .................................... 15153448

(51) Int. Cl.
| | | |
|---|---|---|
| C07D 471/14 | (2006.01) | |
| A61K 31/437 | (2006.01) | |
| A61K 51/04 | (2006.01) | |
| C07B 59/00 | (2006.01) | |

(52) U.S. Cl.
CPC ........ *C07D 471/14* (2013.01); *A61K 51/0455* (2013.01); *A61K 51/0459* (2013.01); *A61K 51/0463* (2013.01); *C07B 59/002* (2013.01); *C07B 2200/05* (2013.01)

(58) Field of Classification Search
CPC .. C07D 471/14; C07D 471/04; A61K 31/437; A61K 51/0455; A61P 25/28

USPC ............................................ 546/82; 514/293
See application file for complete search history.

(56) References Cited

U.S. PATENT DOCUMENTS

| | | |
|---|---|---|
| 3,560,361 A | 2/1971 | Malcolm et al. |
| 11,312,716 B2 * | 4/2022 | Mercier ................. A61P 25/00 |

FOREIGN PATENT DOCUMENTS

| | | |
|---|---|---|
| WO | 2008132454 | 11/2008 |
| WO | 2009102498 | 8/2009 |
| WO | 2013176698 | 11/2013 |
| WO | 2015052105 | 4/2015 |
| WO | 2015110263 | 7/2015 |

OTHER PUBLICATIONS

Jonckers, T.H.M. et al.: Synthesis of Isocryptolepine via a Pd-catalyzed amination-arylation approach. Synlett, vol. 5, pp. 615-618, 2003.*
International Search Report dated Mar. 23, 2016 for International Application PCT/US2016/051993 filed Jan. 29, 2016, 11 pages.
Extended European Search Report dated May 7, 2015 for European Application No. 15153448, 6 pages.

* cited by examiner

*Primary Examiner* — Charanjit Aulakh
(74) *Attorney, Agent, or Firm* — McDonnell Boehnen Hulbert & Berghoff LLP

(57) ABSTRACT

The invention relates to 9H-pyrrolo-dipyridine derivatives of formula I, processes for preparing them, pharmaceutical compositions containing them and their use as radiopharmaceuticals in particular as imaging agents for the detection of Tau aggregates.

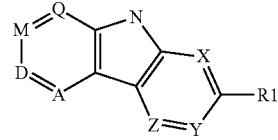

4 Claims, No Drawings

9H-PYRROLO-DIPYRIDINE DERIVATIVES

REFERENCE TO RELATED APPLICATION(S)

This application is a continuation of U.S. application Ser. No. 16/749,537, filed Jan. 22, 2020, which is a continuation of U.S. application Ser. No. 15/547,980, filed Aug. 1, 2017, which is a U.S. national phase application under 35 U.S.C. § 371 of International Patent Application no. PCT/EP2016/051993 filed on Jan. 29, 2016, which claims the benefit of priority of European Application no. 15153448.4 filed Feb. 2, 2015.

FIELD OF THE INVENTION

The invention relates to 9H-pyrrolo-dipyridine derivatives, processes for preparing them, pharmaceutical compositions containing them and their use as radiopharmaceuticals in particular as imaging agents for the detection of Tau aggregates.

BACKGROUND OF THE INVENTION

Alzheimer's disease (AD) and progressive supranuclear palsy (PSP) are neurodegenerative diseases with high medical unmet needs that cause substantial morbidity and mortality, high healthcare costs, and high burden for the families and caregivers of the affected individuals. AD initially causes impaired cognition, especially memory, but eventually AD leads to impairments in multiple domains and the need for patients to live in a nursing home. Ultimately, AD causes death. PSP initially causes symptoms that are often misdiagnosed for Parkinson's disease, affecting balance, gait and eye movement. The disease progresses rapidly, with patients falling, being wheelchair bound and requiring nursing home care. Ultimately, PSP causes death.

Symptomatic treatments for AD and PSP provide limited benefit and there are currently no disease-modifying treatments available.

The brain pathology observed in AD includes amyloid plaques and neurofibrillary tangles. Neurofibrillary tangles are also observed in PSP. The main protein component of neurofibrillary tangles is hyperphosphorylated, aggregated microtubule-associated protein tau (Tau) forming paired helical filaments (PHF).

Tau is a neuronal protein that is unfolded under physiological conditions, associated with microtubules, and which may play a role with their assembly and stabilization (Clavaguera et al. Brain Pathol. 2013 2013 23(3):342-9). Six isoforms were described, three containing three microtubule binding regions (MTBR), three containing four MTBR; the longest form comprises 441 amino acids.

In pathological conditions, Tau undergoes post-translational modifications (hyper-phosphorylation, acetylation, nitrosylation, glycosylation, etc) and self-aggregates on its MTBR. This aggregated post-translationally modified protein is the major component of paired helical filament (PHF) which is the building block of neurofibrillary tangles observed in a range of tauopathy diseases.

The following tauopathies have been described to contain Tau inclusions (Clavaguera et al. Brain Pathol. 2013 2013 23(3):342-9) and may be caused by Tau accumulation: Alzheimer's disease; Amyotrophic lateral sclerosis/parkinsonism-dementia complex; Argyrophilic grain disease; Chronic traumatic encephalopathy; Corticobasal degeneration; Diffuse neurofibrillary tangles with calcification; Down syndrome; Familial British dementia; Familial Danish dementia; Frontotemporal dementia and parkinsonism linked to chromosome 17 caused by MAPT mutations; Frontotemporal lobar degeneration (caused by C9ORF72 mutations); Gerstmann-Sträussler-Scheinker disease; Guadeloupean parkinsonism; Myotonic dystrophy; Neurodegeneration with brain iron accumulation; Niemann-Pick disease, type C; Non-Guamanian motor neuron disease with neurofibrillary tangles; Pick disease; Post-encephalitic parkinsonism; Prion protein cerebral amyloid angiopathy; Progressive subcortical gliosis; Progressive supranuclear palsy; SLC9A6-related mental retardation; Subacute sclerosing panencephalitis; Tangle-only dementia; White matter tauopathy with globular glial inclusions. Direct correlation was shown between tau aggregates in cortical areas and severity of dementia (Braak et al. Acta Neuropathol. 1991 82(4):239-59) suggesting that Tau aggregation might be a potential marker of neurodegenerative disease progression.

An imaging agent that is selective for Tau aggregates compared to other aggregated pathological proteins (beta-amyloid, α-synuclein, TDP-43, . . . ) would allow in-vivo visualization of Tau aggregates in patients therefore allowing a more accurate diagnosis and monitoring of treatment effects. Additionally it would better define the time course of the disease in each individual patient, and assess the efficacy of disease-modifying, tau-targeted treatments.

SUMMARY OF THE INVENTION

The present invention relates to 9H-pyrrolo-dipyridine derivatives, compositions, methods and use as imaging agents for the in vivo detection of Tau aggregates in the brain.

A further aspect of the present invention consists of novel agents that demonstrate high binding to Tau aggregates and have low non-specific binding and high selectivity compared to other aggregated proteins and other unrelated proteins.

Further aspects of the invention will become apparent from the detailed specification.

DETAILED DESCRIPTION OF THE INVENTION

Description

In vivo imaging of Tau pathology would provide novel insights into the time course of deposition of Tau aggregates in the human brain, associations between Tau load and symptoms and between changes in Tau load and symptoms over time, and changes in Tau load when testing novel tau-targeting disease-modifying treatments.

Potential ligands for detecting Tau aggregates in the living brain must be brain penetrant and possess high affinity for Tau aggregates and specificity, especially compared to other aggregated proteins (beta-amyloid, α-synuclein, TDP-43, . . . ) and compared to other unrelated proteins. To achieve this objective, it is known that successful neuroimaging radiotracers must have appropriate lipophilicity (log D 1-3), low non-specific brain tissue binding (Fu≥5%), low molecular weight (<450) and show rapid clearance from blood. (Zhang et al J Med Chem. 2013 56(11):4568-4579).

Potential Tau PET ligands have been described for example in Chien et al. J Alzheimers Dis. 2013; 34(2):457-68 and Maruyama et al. Neuron. 2013 79(6):1094-108. However, it is reported that they may have insufficient sensitivity and specificity to detect changes in Tau load (Villemagne et al. Lancet Neurol. 2015 (1):114-124). The object of the present application is to identify a Tau PET ligand that will improve the identification of potential patients with excess of Tau aggregates in the brain.

The present invention describes compounds that may be used for binding and imaging Tau aggregates, especially for diagnostic and monitoring imaging of Tau aggregates in neurodegenerative diseases such as Progressive supranuclear palsy, Alzheimer's patients, Pick's disease, chronic traumatic encephalopathy, corticobasal degeneration, Frontotemporal dementia and parkinsonism linked to chromosome 17 caused by MAPT mutations, Frontotemporal lobar degeneration, Amyotrophic lateral sclerosis/parkinsonism-dementia complex, Down syndrome and related tauopathies as listed in the background section.

Tricyclic carboline and carbazole compounds are described for example in U.S. Pat. No. 6,177,440 as inhibitors of the human non-pancreatic secretory phospholipase A2 (sPLA$_2$) for the treatment of septic shock and in WO 2013/176698 and U.S. Pat. No. 8,491,869 as senile plaques and neurofibrillary tangles binders for the imaging of β-Amyloid deposits and Tau aggregates.

WO 2009/102498 describes compounds and methods of diagnosing Alzheimer's Disease or a predisposition thereto in a mammal, the method comprising administering to the mammal a diagnostically effective amount of a radiolabeled compound, wherein the compound is selected from the group consisting of radiolabeled flavones, coumarins, carbazoles, quinolinones, chromenones, imidazoles and triazoles derivatives, allowing the compound to distribute into the brain tissue, and imaging the brain tissue, wherein an increase in binding of the compound to the brain tissue compared to a normal control level of binding indicates that the mammal is suffering from or is at risk of developing Alzheimer's Disease.

It has now surprisingly been found that certain tricyclic analogs described hereafter have high affinity to Tau aggregates and are markedly more specific than the compounds described in WO2013/176698, WO 2009/102498 and U.S. Pat. No. 8,491,869. The invention provides imaging agents having a higher selectivity over related and unrelated targets compared to WO2013/176698, WO 2009/102498 and U.S. Pat. No. 8,491,869. The compounds of the present invention display significantly less non-specific binding to brain tissue proteins as demonstrated by the significantly higher rat brain free fractions (Fu). Importantly, the compounds of the present invention are more specific when tested on an extended selectivity profile on unrelated targets, comprising targets highly expressed in the brain. Specifically, they are characterized by a 10-100 fold lower affinity for the monoamine oxidase-A enzyme (MAO-A) and therefore produce significantly less background signal due to MAO-A binding. Because MAO-A is found at higher levels in regions where Tau accumulates initially in PSP (Saura et al. J Neurosci. 1992 (5):1977-1999, Williams et al. Brain. 2007 130 (Pt 6):1566-1576), the use of PET tracers for Tau with affinity for MAO-A may not provide useable information about Tau load in PSP. Whether affinity for MAO-A is a potential problem for Tau imaging in AD is not known.

WO 2015/052105 describes diazacarbazole derivatives of general formula Ro I. as follows

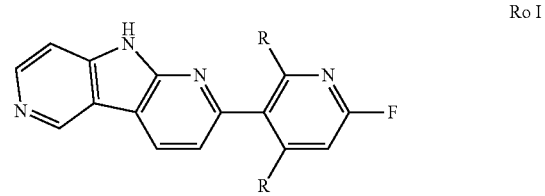

Ro I wherein R is hydrogen or tritium; and F is fluoro or $^{18}$fluoro or to a pharmaceutically acceptable acid addition salt.

WO 2015/052105 describes specifically 2-(6-fluoro-pyridin-3-yl)-9H-dipyrido[2,3-b;3',4'-d]pyrrole (IUPAC name: 2-(6-fluoropyridin-3-yl)-9H-pyrrolo[2,3-b:4,5-c']dipyridine); $^3$H-2-(6-fluoro-pyridin-3-yl)-9H-dipyrido[2,3-b;3',4'-d]pyrrole (IUPAC names: 2-[6-fluoro(2,4-$^3$H$_2$)pyridin-3-yl]-9H-pyrrolo[2,3-b:4,5-c'] dipyridine; 2-[6-fluoro(2-$^3$H)pyridin-3-yl]-9H-pyrrolo [2,3-b:4,5-c']dipyridine; 2-[6-fluoro(4-$^3$H)pyridin-3-yl]-9H-pyrrolo[2,3-b:4,5-c']dipyridine) and [$^{18}$F]-2-(6-fluoro-pyridin-3-yl)-9H-dipyrido[2,3-b;3',4'-d]pyrrole2-(6-fluoropyridin-3-yl)-9H-pyrrolo[2,3-b:4,5-c']dipyridine (IUPAC name: 2-[6-($^{18}$F)fluoropyridin-3-yl]-9H-pyrrolo[2,3-b:4,5-c']dipyridine). These compounds may be used for binding and imaging tau aggregates and related beta-sheet aggregates including besides others beta-amyloid aggregates or alpha-synuclein aggregates.

In one aspect, the present invention relates to compounds of general formula I, or a pharmaceutically acceptable acid addition salt, a racemic mixture or its corresponding enantiomer and/or optical isomers thereof,

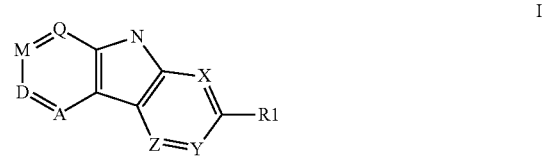

I wherein

R1 is heterocyclyl selected from the group consisting of azetidine, pyrrolidine, piperidine and piperazine, optionally substituted by R2; or heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxy or C1-C6 alkoxy, cyano, amino optionally substituted by C1-C6 alkyl optionally substituted by halogens, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group optionally substituted by halogens or C1-C6 alkyls optionally substituted by halogens; or —NH—C (O)—R2;

R2 is heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxyl or C1-C6 alkoxy, cyano, amino, mono- or di-methyl-amino, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group, X, Y, Z is independently N or CH, one and only one of them having to be a N;

A, D, M, Q is independently N or C—R3, one and only one of them having to be a N;

R3 is H; halogens; C1-C6 alkyls optionally substituted by halogens, hydroxy or C1-C6 alkoxy; C1-C6 alkoxy optionally substituted by halogens, hydroxy or C1-C6 alkoxy; di-methyl-amino; NH—C1-C6 alkyls optionally substituted by halogens, hydroxy or C1-C6 alkoxy; and wherein any H of the formula is H or its $^2$H or $^3$H isotope; any C of the general formula is C or its radioactive isotope $^{14}$C, or $^{11}$C; any F of the formula is F or its radioactive isotope $^{18}$F; any I of the formula is I or its radioactive isotope $^{123}$I, or $^{124}$I;

provided that the compounds of formula I is not a compound selected from the group consisting of 2-(6-fluoropyridin-3-yl)-9H-pyrrolo[2,3-b:4,5-c']dipyridine;

2-[6-fluoro(2,4-$^3$H$_2$)pyridin-3-yl]-9H-pyrrolo[2,3-b:4,5-c']dipyridine;

2-[6-fluoro(2-$^3$H)pyridin-3-yl]-9H-pyrrolo[2,3-b:4,5-c']dipyridine;

2-[6-fluoro(4-$^3$H)pyridin-3-yl]-9H-pyrrolo[2,3-b:4,5-c']dipyridine;

and 2-[6-($^{18}$F)fluoropyridin-3-yl]-9H-pyrrolo[2,3-b:4,5-c']dipyridine.

In another aspect, the present invention relates to compounds of general formula I, or a pharmaceutically acceptable acid addition salt, a racemic mixture or its corresponding enantiomer and/or optical isomers thereof,

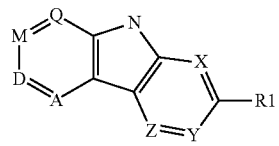

I wherein

R1 is heterocyclyl selected from the group consisting of azetidine, pyrrolidine, piperidine and piperazine, optionally substituted by R2; or heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxy or C1-C6 alkoxy, cyano, amino optionally substituted by C1-C6 alkyl optionally substituted by halogens, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group optionally substituted by halogens or C1-C6 alkyls optionally substituted by halogens; or —NH—C(O)—R2;

R2 is heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxyl or C1-C6 alkoxy, cyano, amino, mono- or di-methyl-amino, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group;

X, Y, Z is independently N or CH, one and only one of them having to be a N;

A, D, M, Q is independently N or C—R3, one and only one of them having to be a N;

R3 is H; halogens; C1-C6 alkyls optionally substituted by halogens, hydroxy or C1-C6 alkoxy; C1-C6 alkoxy optionally substituted by halogens, hydroxy or C1-C6 alkoxy; di-methyl-amino; NH—C1-C6 alkyls optionally substituted by halogens, hydroxy or C1-C6 alkoxy; and wherein any H of the formula is H or its $^2$H or $^3$H isotope; any C of the general formula is C or its radioactive isotope $^{14}$C, or $^{11}$C; any F of the formula is F or its radioactive isotope $^{18}$F; any I of the formula is I or its radioactive isotope $^{123}$I, or $^{124}$I;

provided that the compounds of formula I is not a compound selected from the group consisting of diazacarbazole derivatives of general formula Ro I.

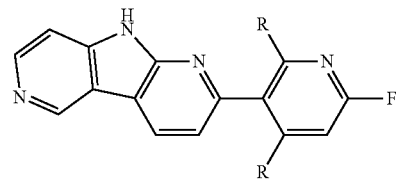

Ro I wherein R is hydrogen or tritium; and F is fluoro or $^{18}$fluoro or to a pharmaceutically acceptable acid addition salt.

Preferably R1 is piperidine and piperazine, optionally substituted by R2; or heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino optionally substituted by methyl or fluoro-ethyl, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group optionally substituted by fluorine or fluoromethyl.

More preferred R1 is pyrazole, thiazole, pyridine, pyrimidine optionally substituted by one or two substituents selected from fluorine, methyl or ethyl or propyl optionally substituted by fluorine or methoxy, cyano, amino optionally substituted by methyl or fluoro-ethyl, nitro, C(O)N-methyl or ethyl or propyl optionally substituted by fluorine or methoxy, methoxy or ethoxy or propoxy optionally substituted by fluorine or methoxy; a morpholine or piperazine or piperidine, optionally substituted by fluorine or fluoromethyl.

Preferably R2 is heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino, mono- or di-methyl-amino, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group.

More preferred R2 is pyrazole, thiazole, pyridine, pyrimidine optionally substituted by one or two substituents selected from fluorine, methyl or ethyl or propyl optionally substituted by fluorine or methoxy, cyano, amino, mono- or di-methyl-amino, nitro, C(O)N-methyl or ethyl or propyl optionally substituted by fluorine or methoxy, methoxy or ethoxy or propoxy optionally substituted by fluorine or methoxy; a morpholine or piperazine.

Preferably X is N, Y is CH and Z is CH; or X is CH, Y is N, and Z is CH.

Preferably A is CH, D is N, M is C—R3, and Q is CH; or A is CH, D is N, M is CH, and Q is CR3; or A is CH, D is C—R3, M is N, and Q is CH; or A is CH, D is CH, M is C—R3, and Q is N.

Preferably R3 is H; fluorine; methyl or ethyl or propyl optionally substituted by fluorine, hydroxy or methoxy; methoxy or ethoxy or propoxy optionally substituted by fluorine or hydroxyl or methoxy; di-methyl-amino; NH-methyl or ethyl or propyl optionally substituted by fluorine, hydroxy or methoxy.

Usually any H of the general formula I is H or is its $^2$H or $^3$H isotope.

Usually C of the general formula I on a benzylic methyl or a methoxy is C or is its radioactive isotope $^{14}$C or $^{11}$C.

Usually any F of the general formula I is F or is its radioactive isotope $^{18}$F.

Usually I of the general formula I on an alkyl or aromatic or heteroaromatic position is I or its radioactive isotope $^{123}$I, or $^{124}$I.

A further embodiment of the present invention consists in compounds of formula I-A, or a pharmaceutically acceptable acid addition salt, a racemic mixture or its corresponding enantiomer and/or optical isomers thereof,

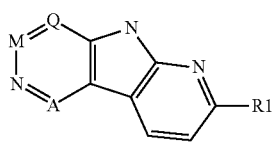

I-A wherein
R1 is heterocyclyl selected from the group consisting of azetidine, pyrrolidine, piperidine and piperazine, optionally substituted by R2; or
heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxy or C1-C6 alkoxy, cyano, amino optionally substituted by C1-C6 alkyl optionally substituted by halogens, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group optionally substituted by halogens or C1-C6 alkyls optionally substituted by halogens; or —NH—C(O)—R2;

R2 is heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxyl or C1-C6 alkoxy, cyano, amino, mono- or di-methyl-amino, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group;

A, M, Q is CR3;
R3 is H; halogen; C1-C6 alkyls optionally substituted by halogens, hydroxy or C1-C6 alkoxy; C1-C6 alkoxy optionally substituted by halogens, hydroxy or C1-C6 alkoxy; di-methyl-amino; NH—C1-C6 alkyls optionally substituted by halogens, hydroxy or C1-C6 alkoxy;

and wherein any H of the formula is H or its $^2$H or $^3$H isotope; any C of the general formula is C or its radioactive isotope $^{14}$C, or $^{11}$C; any F of the formula is F or its radioactive isotope $^{18}$F; any I of the formula is I or its radioactive isotope $^{123}$I, or $^{124}$I;

provided that the compounds of formula I-A is not a compound selected from the group consisting of
2-(6-fluoropyridin-3-yl)-9H-pyrrolo[2,3-b:4,5-c']dipyridine,
2-[6-fluoro(2,4-$^3$H$_2$)pyridin-3-yl]-9H-pyrrolo[2,3-b:4,5-c']dipyridine,
2-[6-fluoro(2-$^3$H)pyridin-3-yl]-9H-pyrrolo[2,3-b:4,5-c']dipyridine,
2-[6-fluoro(4-$^3$H)pyridin-3-yl]-9H-pyrrolo[2,3-b:4,5-c']dipyridine, and
2-[6-($^{18}$F)fluoropyridin-3-yl]-9H-pyrrolo[2,3-b:4,5-c']dipyridine.

Preferably R1 is
piperidine and piperazine, optionally substituted by R2; or
heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino optionally substituted by methyl or fluoro-ethyl, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group optionally substituted by fluorine or fluoromethyl.

More preferred R1 is pyrazole, thiazole, pyridine, pyrimidine optionally substituted by one or two substituents selected from fluorine, methyl or ethyl or propyl optionally substituted by fluorine or methoxy, cyano, amino optionally substituted by methyl or fluoro-ethyl, nitro, C(O)N-methyl or ethyl or propyl optionally substituted by fluorine or methoxy, methoxy or ethoxy or propoxy optionally substituted by fluorine or methoxy; a morpholine or piperazine or piperidine, optionally substituted by fluorine or fluoromethyl.

Preferably R2 is heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino, mono- or di-methyl-amino, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group.

More preferred R2 is pyrazole, thiazole, pyridine, pyrimidine optionally substituted by one or two substituents selected from fluorine, methyl or ethyl or propyl optionally substituted by fluorine or methoxy, cyano, amino, mono- or di-methyl-amino, nitro, C(O)N-methyl or ethyl or propyl optionally substituted by fluorine or methoxy, methoxy or ethoxy or propoxy optionally substituted by fluorine or methoxy; a morpholine or piperazine.

Preferably A is CH, M is C—R3, and Q is CH; or A is CH, M is CH, and Q is CR3.

Preferably R3 is H; fluorine; methyl or ethyl or propyl optionally substituted by fluorine, hydroxy or methoxy; methoxy or ethoxy or propoxy optionally substituted by fluorine or hydroxyl or methoxy; di-methyl-amino; NH-methyl or ethyl or propyl optionally substituted by fluorine, hydroxy or methoxy.

Usually any H of the general formula I is H or is its $^2$H or $^3$H isotope.

Usually C of the general formula on a benzylic methyl or a methoxy is C or is its radioactive isotope $^{14}$C or $^{11}$C.

Usually any F of the general formula is F or is its radioactive isotope $^{18}$F.

Usually I of the general formula I on an alkyl or aromatic or heteroaromatic position is I or its radioactive isotope $^{123}$I, or $^{124}$I.

Specific compounds of the present invention are those selected from the group consisting of:
2-(pyridin-4-yl)-9H-pyrrolo[2,3-b:4,5-c']dipyridine
2-(2-methoxypyridin-4-yl)-9H-pyrrolo[2,3-b:4,5-c']dipyridine
2-(pyridin-3-yl)-9H-pyrrolo[2,3-b:4,5-c']dipyridine
2-(1-methyl-1H-pyrazol-4-yl)-9H-pyrrolo[2,3-b:4,5-c']dipyridine
2-(6-methoxypyridin-3-yl)-9H-pyrrolo[2,3-b:4,5-c']dipyridine
5-(9H-pyrrolo[2,3-b:4,5-c']dipyridin-2-yl)pyridin-2(1H)-one
2-(5-fluoro-6-methoxypyridin-3-yl)-9H-pyrrolo[2,3-b:4,5-c']dipyridine
2-(furan-3-yl)-9H-pyrrolo[2,3-b:4,5-c']dipyridine
2-(1H-pyrazol-4-yl)-9H-pyrrolo[2,3-b:4,5-c']dipyridine
2-[2-(morpholin-4-yl)pyrimidin-5-yl]-9H-pyrrolo[2,3-b:4,5-c']dipyridine
N-methyl-5-(9H-pyrrolo[2,3-b:4,5-c']dipyridin-2-yl)pyridine-2-carboxamide
3-fluoro-5-(9H-pyrrolo[2,3-b:4,5-c']dipyridin-2-yl)pyridin-2-amine
2-[4-(pyrimidin-2-yl)piperazin-1-yl]-9H-pyrrolo[2,3-b:4,5-c']dipyridine
2-[4-(pyridin-4-yl)piperazin-1-yl]-9H-pyrrolo[2,3-b:4,5-c']dipyridine
2-(1H-pyrazol-3-yl)-9H-pyrrolo[2,3-b:4,5-c']dipyridine
4-(9H-pyrrolo[2,3-b:4,5-c']dipyridin-2-yl)pyridin-2-amine
4-(9H-pyrrolo[2,3-b:4,5-c']dipyridin-2-yl)pyridin-2(1H)-one
2-(5-fluoropyridin-2-yl)-9H-pyrrolo[2,3-b:4,5-c']dipyridine
2-fluoro-5-(9H-pyrrolo[2,3-b:4,5-c']dipyridin-2-yl)pyridin-3-amine
N-methyl-5-(9H-pyrrolo[2,3-b:4,5-c']dipyridin-2-yl)pyrimidin-2-amine
2-[6-(morpholin-4-yl)pyridin-3-yl]-9H-pyrrolo[2,3-b:4,5-c']dipyridine
N-(2-methoxyethyl)-5-(9H-pyrrolo[2,3-b:4,5-c']dipyridin-2-yl)pyrimidin-2-amine
2-[2-(piperazin-1-yl)pyrimidin-5-yl]-9H-pyrrolo[2,3-b:4,5-c']dipyridine
2-(5-methyl-1H-pyrazol-3-yl)-9H-pyrrolo[2,3-b:4,5-c']dipyridine
2-[1-(2-fluoroethyl)-1H-pyrazol-4-yl]-9H-pyrrolo[2,3-b:4,5-c']dipyridine
N-methyl-2-[4-(9H-pyrrolo[2,3-b:4,5-c']dipyridin-2-yl)-1H-pyrazol-1-yl]acetamide
N-methyl-6-(9H-pyrrolo[2,3-b:4,5-c']dipyridin-2-yl)pyridine-3-carboxamide
N,N-dimethyl-5-(9H-pyrrolo[2,3-b:4,5-c']dipyridin-2-yl)pyridine-2-carboxamide
N-(2-fluoroethyl)-5-(9H-pyrrolo[2,3-b:4,5-c']dipyridin-2-yl)pyridine-2-carboxamide
N-(2-methoxyethyl)-5-(9H-pyrrolo[2,3-b:4,5-c']dipyridin-2-yl)pyridine-2-carboxamide
2-(4-methoxy-1H-pyrazol-1-yl)-9H-pyrrolo[2,3-b:4,5-c']dipyridine
2-[2-(morpholin-4-yl)-1,3-thiazol-5-yl]-9H-pyrrolo[2,3-b:4,5-c']dipyridine
1-{4-[5-(9H-pyrrolo[2,3-b:4,5-c']dipyridin-2-yl)pyrimidin-2-yl]piperazin-1-yl}ethanone
6-fluoro-N-(9H-pyrrolo[2,3-b:4,5-c']dipyridin-2-yl)pyridine-3-carboxamide
6-(methylamino)-N-(9H-pyrrolo[2,3-b:4,5-c']dipyridin-2-yl)pyridine-3-carboxamide
2-(6-fluoropyridin-3-yl)-7-methoxy-9H-pyrrolo[2,3-b:4,5-c']dipyridine
5-(7-methoxy-9H-pyrrolo[2,3-b:4,5-c']dipyridin-2-yl)-N-methylpyridine-2-carboxamide
7-methoxy-2-(1-methyl-1H-pyrazol-4-yl)-9H-pyrrolo[2,3-b:4,5-c']dipyridine
7-methoxy-2-[2-(morpholin-4-yl)pyrimidin-5-yl]-9H-pyrrolo[2,3-b:4,5-c']dipyridine
6-(7-methoxy-9H-pyrrolo[2,3-b:4,5-c']dipyridin-2-yl)-N-methylpyridine-3-carboxamide
5-(7-methoxy-9H-pyrrolo[2,3-b:4,5-c']dipyridin-2-yl)pyrimidine-2-carbonitrile
2-(6-fluoropyridin-3-yl)-N,N-dimethyl-9H-pyrrolo[2,3-b:4,5-c']dipyridin-7-amine
5-[7-(dimethylamino)-9H-pyrrolo[2,3-b:4,5-c']dipyridin-2-yl]-N-methylpyridine-2-carboxamide
N,N-dimethyl-2-(1-methyl-1H-pyrazol-4-yl)-9H-pyrrolo[2,3-b:4,5-c']dipyridin-7-amine
2-(6-fluoropyridin-3-yl)-7-methyl-9H-pyrrolo[2,3-b:4,5-c']dipyridine
N-methyl-5-(7-methyl-9H-pyrrolo[2,3-b:4,5-c']dipyridin-2-yl)pyridine-2-carboxamide
7-methyl-2-(1-methyl-1H-pyrazol-4-yl)-9H-pyrrolo[2,3-b:4,5-c']dipyridine
2-(6-fluoropyridin-3-yl)-7-(methoxymethyl)-9H-pyrrolo[2,3-b:4,5-c']dipyridine
5-[7-(methoxymethyl)-9H-pyrrolo[2,3-b:4,5-c']dipyridin-2-yl]-N-methylpyridine-2-carboxamide
7-(methoxymethyl)-2-(1-methyl-1H-pyrazol-4-yl)-9H-pyrrolo[2,3-b:4,5-c']dipyridine
2-[6-fluoro(2-$^3$H)pyridin-3-yl](5,7-$^3$H$_2$)-9H-pyrrolo[2,3-b:4,5-c']dipyridine 2-[6-fluoro(2-²H)pyridin-3-yl](5,7-²H₂)-9H-pyrrolo[2,3-b:4,5-c']dipyridine 2-(6-fluoropyridin-3-yl)(3-²H)-9H-pyrrolo[2,3-b:4,5-c']dipyridine 2-(6-fluoropyridin-3-yl)(8-²H)-9H-pyrrolo[2,3-b:4,5-c']dipyridine 2-[6-fluoro(5-²H)pyridin-3-yl]-9H-pyrrolo[2,3-b:4,5-c']dipyridine N-methyl-5-[(5,7-³H₂)-9H-pyrrolo[2,3-b:4,5-c']dipyridin-2-yl](6-³H)pyridine-2-carboxamide 2-[1-methyl(3-³H)-1H-pyrazol-4-yl](5,7-³H₂)-9H-pyrrolo[2,3-b:4,5-c']dipyridine.

In another embodiment, specific compounds of the present invention are those selected from the group consisting of:

2-(pyridin-4-yl)-9H-pyrrolo[2,3-b:4,5-c']dipyridine
2-(2-methoxypyridin-4-yl)-9H-pyrrolo[2,3-b:4,5-c']dipyridine
2-(pyridin-3-yl)-9H-pyrrolo[2,3-b:4,5-c']dipyridine
2-(1-methyl-1H-pyrazol-4-yl)-9H-pyrrolo[2,3-b:4,5-c']dipyridine
2-(6-methoxypyridin-3-yl)-9H-pyrrolo[2,3-b:4,5-c']dipyridine
5-(9H-pyrrolo[2,3-b:4,5-c']dipyridin-2-yl)pyridin-2(1H)-one
2-(5-fluoro-6-methoxpyridin-3-yl)-9H-pyrrolo[2,3-b:4,5-c']dipyridine
2-(furan-3-yl)-9H-pyrrolo[2,3-b:4,5-c']dipyridine
2-(1H-pyrazol-4-yl)-9H-pyrrolo[2,3-b:4,5-c']dipyridine
2-[2-(morpholin-4-yl)pyrimidin-5-yl]-9H-pyrrolo[2,3-b:4,5-c']dipyridine
N-methyl-5-(9H-pyrrolo[2,3-b:4,5-c']dipyridin-2-yl)pyridine-2-carboxamide
3-fluoro-5-(9H-pyrrolo[2,3-b:4,5-c']dipyridin-2-yl)pyridin-2-amine
2-[4-(pyrimidin-2-yl)piperazin-1-yl]-9H-pyrrolo[2,3-b:4,5-c']dipyridine
2-[4-(pyridin-4-yl)piperazin-1-yl]-9H-pyrrolo[2,3-b:4,5-c']dipyridine
2-(1H-pyrazol-3-yl)-9H-pyrrolo[2,3-b:4,5-c']dipyridine
4-(9H-pyrrolo[2,3-b:4,5-c']dipyridin-2-yl)pyridin-2-amine
4-(9H-pyrrolo[2,3-b:4,5-c']dipyridin-2-yl)pyridin-2(1H)-one
2-(5-fluoropyridin-2-yl)-9H-pyrrolo[2,3-b:4,5-c']dipyridine
2-fluoro-5-(9H-pyrrolo[2,3-b:4,5-c']dipyridin-2-yl)pyridin-3-amine
N-methyl-5-(9H-pyrrolo[2,3-b:4,5-c']dipyridin-2-yl)pyrimidin-2-amine
2-[6-(morpholin-4-yl)pyridin-3-yl]-9H-pyrrolo[2,3-b:4,5-c']dipyridine
N-(2-methoxyethyl)-5-(9H-pyrrolo[2,3-b:4,5-c']dipyridin-2-yl)pyrimidin-2-amine
2-[2-(piperazin-1-yl)pyrimidin-5-yl]-9H-pyrrolo[2,3-b:4,5-c']dipyridine
2-(5-methyl-1H-pyrazol-3-yl)-9H-pyrrolo[2,3-b:4,5-c']dipyridine
2-[1-(2-fluoroethyl)-1H-pyrazol-4-yl]-9H-pyrrolo[2,3-b:4,5-c']dipyridine
N-methyl-2-[4-(9H-pyrrolo[2,3-b:4,5-c']dipyridin-2-yl)-1H-pyrazol-1-yl]acetamide
N-methyl-6-(9H-pyrrolo[2,3-b:4,5-c']dipyridin-2-yl)pyridine-3-carboxamide
N,N-dimethyl-5-(9H-pyrrolo[2,3-b:4,5-c']dipyridin-2-yl)pyridine-2-carboxamide
N-(2-fluoroethyl)-5-(9H-pyrrolo[2,3-b:4,5-c']dipyridin-2-yl)pyridine-2-carboxamide
N-(2-methoxyethyl)-5-(9H-pyrrolo[2,3-b:4,5-c']dipyridin-2-yl)pyridine-2-carboxamide
2-(4-methoxy-1H-pyrazol-1-yl)-9H-pyrrolo[2,3-b:4,5-c']dipyridine
2-[2-(morpholin-4-yl)-1,3-thiazol-5-yl]-9H-pyrrolo[2,3-b:4,5-c']dipyridine
1-{4-[5-(9H-pyrrolo[2,3-b:4,5-c']dipyridin-2-yl)pyrimidin-2-yl]piperazin-1-yl}ethanone
6-fluoro-N-(9H-pyrrolo[2,3-b:4,5-c']dipyridin-2-yl)pyridine-3-carboxamide
6-(methylamino)-N-(9H-pyrrolo[2,3-b:4,5-c']dipyridin-2-yl)pyridine-3-carboxamide
2-(6-fluoropyridin-3-yl)-7-methoxy-9H-pyrrolo[2,3-b:4,5-c']dipyridine
5-(7-methoxy-9H-pyrrolo[2,3-b:4,5-c']dipyridin-2-yl)-N-methylpyridine-2-carboxamide
7-methoxy-2-(1-methyl-1H-pyrazol-4-yl)-9H-pyrrolo[2,3-b:4,5-c']dipyridine
7-methoxy-2-[2-(morpholin-4-yl)pyrimidin-5-yl]-9H-pyrrolo[2,3-b:4,5-c']dipyridine
6-(7-methoxy-9H-pyrrolo[2,3-b:4,5-c']dipyridin-2-yl)-N-methylpyridine-3-carboxamide
5-(7-methoxy-9H-pyrrolo[2,3-b:4,5-c']dipyridin-2-yl)pyrimidine-2-carbonitrile
2-(6-fluoropyridin-3-yl)-N,N-dimethyl-9H-pyrrolo[2,3-b:4,5-c']dipyridin-7-amine
5-[7-(dimethylamino)-9H-pyrrolo[2,3-b:4,5-c']dipyridin-2-yl]-N-methylpyridine-2-carboxamide
N,N-dimethyl-2-(1-methyl-1H-pyrazol-4-yl)-9H-pyrrolo[2,3-b:4,5-c']dipyridin-7-amine
2-(6-fluoropyridin-3-yl)-7-methyl-9H-pyrrolo[2,3-b:4,5-c']dipyridine
N-methyl-5-(7-methyl-9H-pyrrolo[2,3-b:4,5-c']dipyridin-2-yl)pyridine-2-carboxamide
7-methyl-2-(1-methyl-1H-pyrazol-4-yl)-9H-pyrrolo[2,3-b:4,5-c']dipyridine
2-(6-fluoropyridin-3-yl)-7-(methoxymethyl)-9H-pyrrolo[2,3-b:4,5-c']dipyridine
5-[7-(methoxymethyl)-9H-pyrrolo[2,3-b:4,5-c']dipyridin-2-yl]-N-methylpyridine-2-carboxamide
7-(methoxymethyl)-2-(1-methyl-1H-pyrazol-4-yl)-9H-pyrrolo[2,3-b:4,5-c']dipyridine.

In another embodiment, specific compounds of the present invention are those selected from the group consisting of:

2-[6-fluoro(2-³H)pyridin-3-yl](5,7-³H₂)-9H-pyrrolo[2,3-b:4,5-c']dipyridine
N-methyl-5-[(5,7-³H₂)-9H-pyrrolo[2,3-b:4,5-c']dipyridin-2-yl](6-³H)pyridine-2-carboxamide
2-[1-methyl(3-³H)-1H-pyrazol-4-yl](5,7-³H₂)-9H-pyrrolo[2,3-b:4,5-c']dipyridine.

In another embodiment, specific compounds of the present invention are those selected from the group consisting of:

2-[6-fluoro(2-²H)pyridin-3-yl](5,7-²H₂)-9H-pyrrolo[2,3-b:4,5-c']dipyridine
2-(6-fluoropyridin-3-yl)(3-²H)-9H-pyrrolo[2,3-b:4,5-c']dipyridine
2-(6-fluoropyridin-3-yl)(8-²H)-9H-pyrrolo[2,3-b:4,5-c']dipyridine
2-[6-fluoro(5-²H)pyridin-3-yl]-9H-pyrrolo[2,3-b:4,5-c']dipyridine.

Preferred compounds are 2-(6-fluoropyridin-3-yl)(3-²H)-9H-pyrrolo[2,3-b:4,5-c']dipyridine; and 2-(6-fluoropyridin-3-yl)(8-²H)-9H-pyrrolo[2,3-b:4,5-c']dipyridine.

A further embodiment of the present invention consists in compounds of formula I-B, or a pharmaceutically acceptable acid addition salt, a racemic mixture or its corresponding enantiomer and/or optical isomers thereof,

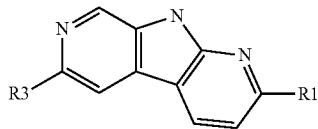

I-B wherein
R1 is heterocyclyl selected from the group consisting of azetidine, pyrrolidine, piperidine and piperazine, optionally substituted by R2; or
heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxy or C1-C6 alkoxy, cyano, amino optionally substituted by C1-C6 alkyl optionally substituted by halogens, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group optionally substituted by halogens or C1-C6 alkyls optionally substituted by halogens; or —NH—C(O)—R2;
R2 is heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxyl or C1-C6 alkoxy, cyano, amino, mono- or di-methyl-amino, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group;
R3 is H; halogen; C1-C6 alkyls optionally substituted by halogens, hydroxy or C1-C6 alkoxy; C1-C6 alkoxy optionally substituted by halogens, hydroxy or C1-C6 alkoxy; di-methyl-amino; NH—C1-C6 alkyls optionally substituted by halogens, hydroxy or C1-C6 alkoxy;
and wherein any H of the formula is H or its $^2$H or $^3$H isotope; any C of the general formula is C or its radioactive isotope 14C, or 11C; any F of the formula is F or its radioactive isotope 18F; any 1 of the formula is 1 or its radioactive isotope 123I, or 124I.

Preferably R1 is
piperidine and piperazine, optionally substituted by R2; or
heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino optionally substituted by methyl or fluoro-ethyl, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group optionally substituted by fluorine or fluoromethyl.

More preferred R1 is pyrazole, thiazole, pyridine, pyrimidine optionally substituted by one or two substituents selected from fluorine, methyl or ethyl or propyl optionally substituted by fluorine or methoxy, cyano, amino optionally substituted by methyl or fluoro-ethyl, nitro, C(O)N-methyl or ethyl or propyl optionally substituted by fluorine or methoxy, methoxy or ethoxy or propoxy optionally substituted by fluorine or methoxy; a morpholine or piperazine or piperidine, optionally substituted by fluorine or fluoromethyl.

Preferably R2 is heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino, mono- or di-methyl-amino, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group.

More preferred R2 is pyrazole, thiazole, pyridine, pyrimidine optionally substituted by one or two substituents selected from fluorine, methyl or ethyl or propyl optionally substituted by fluorine or methoxy, cyano, amino, mono- or di-methyl-amino, nitro, C(O)N-methyl or ethyl or propyl optionally substituted by fluorine or methoxy, methoxy or ethoxy or propoxy optionally substituted by fluorine or methoxy; a morpholine or piperazine.

Preferably R3 is H; fluorine; methyl or ethyl or propyl optionally substituted by fluorine, hydroxy or methoxy; methoxy or ethoxy or propoxy optionally substituted by fluorine or hydroxyl or methoxy; di-methyl-amino; NH-methyl or ethyl or propyl optionally substituted by fluorine, hydroxy or methoxy.

Usually any H of the general formula I-B is H or is its $^2$H or $^3$H isotope.

Usually C of the general formula I-B on a benzylic methyl or a methoxy is C or is its radioactive isotope $^{14}$C or $^{11}$C.

Usually any F of the general formula I-B is F or is its radioactive isotope $^{18}$F.

Usually I of the general formula I-B on an alkyl or aromatic or heteroaromatic position is I or its radioactive isotope $^{123}$I, or $^{124}$I.

Specific compounds of the present invention are those selected from the group consisting of:

2-(1-methyl-1H-pyrazol-4-yl)-9H-pyrrolo[2,3-b:5,4-c]dipyridine 2-(1H-pyrazol-4-yl)-9H-pyrrolo[2,3-b:5,4-c]dipyridine N-methyl-5-(9H-pyrrolo[2,3-b:5,4-c]dipyridin-2-yl)pyridine-2-carboxamide 2-(6-fluoropyridin-3-yl)-9H-pyrrolo[2,3-b:5,4-c']dipyridine N-methyl-5-(9H-pyrrolo[2,3-b:5,4-c']dipyridin-2-yl)pyridin-2-amine 2-(4-methoxy-1H-pyrazol-1-yl)-9H-pyrrolo[2,3-b:5,4-c]dipyridine 2-[6-fluoro(2-$^3$H)pyridin-3-yl](6,8-$^3$H$_2$)-9H-pyrrolo[2,3-b:5,4-c]dipyridine.

A further embodiment of the present invention consists in compounds of formula I-C, or a pharmaceutically acceptable acid addition salt, a racemic mixture or its corresponding enantiomer and/or optical isomers thereof,

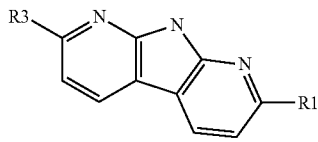

I-C wherein
R1 is heterocyclyl selected from the group consisting of azetidine, pyrrolidine, piperidine and piperazine, optionally substituted by R2; or
heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxy or C1-C6 alkoxy, cyano, amino optionally substituted by C1-C6 alkyl optionally substituted by halogens, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group optionally substituted by halogens or C1-C6 alkyls optionally substituted by halogens; or —NH—C(O)—R2;

R2 is heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxyl or C1-C6 alkoxy, cyano, amino, mono- or di-methyl-amino, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group;

R3 is H; halogen; C1-C6 alkyls optionally substituted by halogens, hydroxy or C1-C6 alkoxy; C1-C6 alkoxy optionally substituted by halogens, hydroxy or C1-C6 alkoxy; di-methyl-amino; NH—C1-C6 alkyls optionally substituted by halogens, hydroxy or C1-C6 alkoxy;

and wherein any H of the formula is H or its $^2$H or $^3$H isotope; any C of the general formula is C or its radioactive isotope $^{14}$C, or $^{11}$C; any F of the formula is F or its radioactive isotope $^{18}$F; any I of the formula is I or its radioactive isotope $^{123}$I, or $^{124}$I.

Preferably R1 is
piperidine and piperazine, optionally substituted by R2; or
heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino optionally substituted by methyl or fluoro-ethyl, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group optionally substituted by fluorine or fluoromethyl.

More preferred R1 is pyrazole, thiazole, pyridine, pyrimidine optionally substituted by one or two substituents selected from fluorine, methyl or ethyl or propyl optionally substituted by fluorine or methoxy, cyano, amino optionally substituted by methyl or fluoro-ethyl, nitro, C(O)N-methyl or ethyl or propyl optionally substituted by fluorine or methoxy, methoxy or ethoxy or propoxy optionally substituted by fluorine or methoxy; a morpholine or piperazine or piperidine, optionally substituted by fluorine or fluoromethyl.

Preferably R2 is heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino, mono- or di-methyl-amino, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group.

More preferred R2 is pyrazole, thiazole, pyridine, pyrimidine optionally substituted by one or two substituents selected from fluorine, methyl or ethyl or propyl optionally substituted by fluorine or methoxy, cyano, amino, mono- or di-methyl-amino, nitro, C(O)N-methyl or ethyl or propyl optionally substituted by fluorine or methoxy, methoxy or ethoxy or propoxy optionally substituted by fluorine or methoxy; a morpholine or piperazine.

Preferably R3 is H; fluorine; methyl or ethyl or propyl optionally substituted by fluorine, hydroxy or methoxy; methoxy or ethoxy or propoxy optionally substituted by fluorine or hydroxyl or methoxy; di-methyl-amino; NH-methyl or ethyl or propyl optionally substituted by fluorine, hydroxy or methoxy.

Usually any H of the general formula I-C is H or is its $^2$H or $^3$H isotope.

Usually C of the general formula I-C on a benzylic methyl or a methoxy is C or is its radioactive isotope $^{14}$C or $^{11}$C.

Usually any F of the general formula I-C is F or is its radioactive isotope $^{18}$F.

Usually I of the general formula I-C on an alkyl or aromatic or heteroaromatic position is I or its radioactive isotope $^{123}$I, or $^{124}$I.

Specific compounds of the present invention are those selected from the group consisting of
2-(6-fluoropyridin-3-yl)-9H-pyrrolo[2,3-b:5,4-b]dipyridine
2-[4-(3-fluoropropyl)piperidin-1-yl]-9H-pyrrolo[2,3-b:5,4-b]dipyridine.

A further embodiment of the present invention consists in compounds of formula I-D, or a pharmaceutically acceptable acid addition salt, a racemic mixture or its corresponding enantiomer and/or optical isomers thereof,

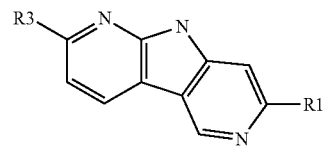

I-D wherein
R1 is heterocyclyl selected from the group consisting of azetidine, pyrrolidine, piperidine and piperazine, optionally substituted by R2; or
heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxy or C1-C6 alkoxy, cyano, amino optionally substituted by C1-C6 alkyl optionally substituted by halogens, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group optionally substituted by halogens or C1-C6 alkyls optionally substituted by halogens; or —NH—C(O)—R2;

R2 is heteroaromatics selected from the group consisting of pyrazole, furan, isoxazole, thiazole, pyridine, pyridine-2-one, pyrimidine, pyrazine, pyridazine optionally substituted by one or two substituents selected from halogen, C1-C6 alkyls optionally substituted by halogens or hydroxyl or C1-C6 alkoxy, cyano, amino, mono- or di-methyl-amino, nitro, NHC(O)—C1-C6 alkyl, C(O)N—C1-C6 alkyl optionally substituted by halogens or hydroxy or C1-C6 alkoxy, C1-C6 alkoxy optionally substituted by halogens or hydroxy or C1-C6 alkoxy, a heterocyclyl group;

R3 is H; halogen; C1-C6 alkyls optionally substituted by halogens, hydroxy or C1-C6 alkoxy; C1-C6 alkoxy optionally substituted by halogens, hydroxy or C1-C6 alkoxy; di-methyl-amino; NH—C1-C6 alkyls optionally substituted by halogens, hydroxy or C1-C6 alkoxy;

And wherein any H of the formula is H or its $^2$H or $^3$H isotope; any C of the general formula is C or its radioactive isotope $^{14}$C, or $^{11}$C; any F of the formula is F or its radioactive isotope $^{18}$F; any I of the formula is I or its radioactive isotope $^{123}$I or $^{124}$I.

Preferably R1 is piperidine and piperazine, optionally substituted by R2; or heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino optionally substituted by methyl or fluoro-ethyl, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group optionally substituted by fluorine or fluoromethyl.

More preferred R1 is pyrazole, thiazole, pyridine, pyrimidine optionally substituted by one or two substituents selected from fluorine, methyl or ethyl or propyl optionally substituted by fluorine or methoxy, cyano, amino optionally substituted by methyl or fluoro-ethyl, nitro, C(O)N-methyl or ethyl or propyl optionally substituted by fluorine or methoxy, methoxy or ethoxy or propoxy optionally substituted by fluorine or methoxy; a morpholine or piperazine or piperidine, optionally substituted by fluorine or fluoromethyl.

Preferably R2 is heteroaromatics selected from the group consisting of pyrazole, thiazole, pyridine, pyridine-2-one, pyrimidine, pyrazine, pyridazine optionally substituted by one or two substituents selected from fluorine, methyl or ethyl or propyl optionally substituted by fluorine or methoxy, cyano, amino, mono- or di-methyl-amino, nitro, NHC(O)-methyl or ethyl or propyl optionally substituted by fluorine or methoxy, C(O)N-methyl or ethyl or propyl optionally substituted by fluorine or methoxy, methoxy or ethoxy or propoxy optionally substituted by fluorine or methoxy, a heterocyclyl group.

More preferred R2 is pyrazole, thiazole, pyridine, pyrimidine optionally substituted by one or two substituents selected from fluorine, methyl or ethyl or propyl optionally substituted by fluorine or methoxy, cyano, amino, mono- or di-methyl-amino, nitro, C(O)N-methyl or ethyl or propyl optionally substituted by fluorine or methoxy, methoxy or ethoxy or propoxy optionally substituted by fluorine or methoxy; a morpholine or piperazine.

Preferably R3 is H; fluorine; methyl or ethyl or propyl optionally substituted by fluorine, hydroxy or methoxy; methoxy or ethoxy or propoxy optionally substituted by fluorine or hydroxyl or methoxy; di-methyl-amino; NH-methyl or ethyl or propyl optionally substituted by fluorine, hydroxy or methoxy.

Usually any H of the general formula I-D is H or is its $^2$H or $^3$H isotope.

Usually C of the general formula I-D on a benzylic methyl or a methoxy is C or is its radioactive isotope $^{14}$C or $^{11}$C.

Usually any F of the general formula I-D is F or is its radioactive isotope $^{18}$F.

Usually I of the general formula I-D on an alkyl or aromatic or heteroaromatic position is I or its radioactive isotope $^{123}$I, or $^{124}$I.

Specific compounds of the present invention are those selected from the group consisting of 7-(1-methyl-1H-pyrazol-4-yl)-9H-pyrrolo[2,3-b:4,5-c'] dipyridine 7-(6-fluoropyridin-3-yl)-9H-pyrrolo[2,3-b:4,5-c']dipyridine N-methyl-5-(9H-pyrrolo[2,3-b:4,5-c']dipyridin-7-yl)pyridine-2-carboxamide.

The following paragraphs provide definitions of the various chemical moieties that make up the compounds according to the invention and are intended to apply uniformly throughout the specification and claims unless an otherwise expressly set out definition provides a broader definition.

As used herein, the term "C1-C6 alkyl" refers to a saturated, aliphatic hydrocarbon group including a straight or branched carbon chain with 1-6 carbon atoms. Examples for "alkyl" are methyl, ethyl, n-propyl, and isopropyl.

The term "C1-C6 alkoxy" refers to a group —O—R' wherein R' is C1-C6 alkyl as defined above.

The term "halogen" refers to fluorine, chlorine, bromine or iodine.

The term "C1-C6 alkyl substituted by halogens or hydroxy or C1-C6 alkoxy" refers to an alkyl group as defined above, wherein at least one hydrogen atom is replaced by a halogen atom, a hydroxyl or a C1-C6 alkoxy.

The term "C1-C6 alkoxy substituted by halogens or hydroxy or C1-C6 alkoxy" refers to an alkoxy group as defined above, wherein at least one hydrogen atom is replaced by a halogen atom, a hydroxyl or a C1-C6 alkoxy.

The term "heterocyclyl" refers to a saturated ring, containing 1-3 heteroatoms, selected from N, O or S, for example morpholinyl, piperazinyl, piperidinyl or pyrrolidinyl or azetidinyl.

The term "pharmaceutically acceptable salt" or "pharmaceutically acceptable acid addition salt" according to the invention embraces therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, oxalic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The invention also relates to all stereoisomeric forms such as enantiomeric and diastereoisomeric forms of the compounds of formula I or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

Some of the compounds of formula I may also exist in tautomeric forms. Such forms although not explicitly indicated in the above formula are intended to be included within the scope of the present invention.

For imaging studies, compounds of formula I or their pharmaceutically acceptable salts may be administered in the form of a pharmaceutical composition.

II-C and II-D which is strictly similar respectfully to general formula I, I-A, I-B, I-C and I-D except that R1 is halogen.

Synthetic Methods

The compounds of formula I according to the invention can be prepared analogously to conventional methods as understood by the person skilled in the art of synthetic organic chemistry.

According to one embodiment, some compounds of general formula I-A to I-D may be prepared by a Suzuki coupling reaction of a chloropyridine intermediate II-A to II-D and a boronic acid (or its corresponding boronic ester or trifluoroborate salt) III:

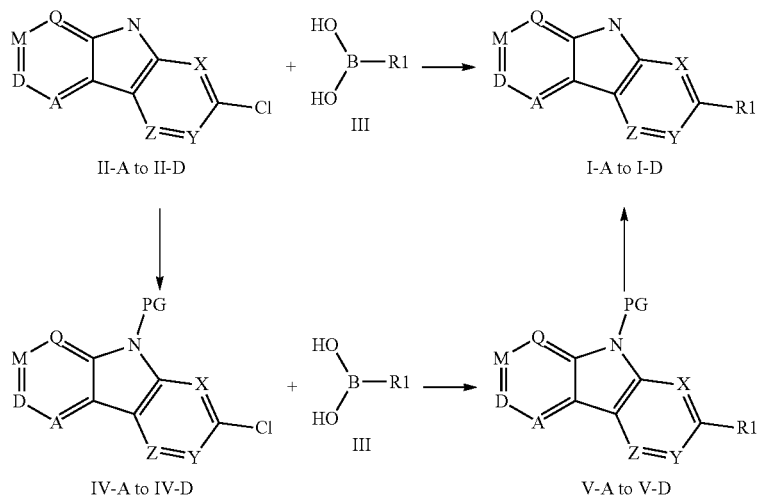

Therefore, another embodiment of the present invention concerns a pharmaceutical composition comprising a detectable amount of a compound of formula I or a pharmaceutically acceptable salt thereof in combination with a pharmaceutically acceptable diluent or carrier.

The compounds of formula I may be used for diagnostic imaging of Tau-aggregate deposits in the brain of a mammal.

Therefore, another embodiment of the present invention is a method of imaging Tau aggregates, including introducing into a mammal a detectable quantity of a pharmaceutical composition of a compound of formula I; allowing sufficient time for the compound of formula I to be associated with Tau aggregates in the mammal brain; and detecting the compound of formula I associated with Tau aggregates.

Preferably, the compounds of formula I can be used for diagnostic and monitoring imaging of Tau aggregates in the brain of human patients suffering from a tauophathy as listed above.

In another embodiment, the present invention concerns a compound as listed above for use as diagnostic and monitoring imaging tool of Tau aggregates in the brain.

In another embodiment, the present invention concerns a compound as listed above for use as a medicament.

In a specific embodiment, the present invention concerns a compound as listed above for use as a medicament in the treatment of neurodegenerative diseases.

In another embodiment, the present invention concerns a pharmaceutical composition containing a compound as listed above as well as pharmaceutically acceptable excipients.

In another embodiment, the present invention concerns synthesis intermediates of general formula II, II-A, II-B, This reaction may be performed in the presence of classical palladium catalytic systems such as [1,1'-Bis(diphenylphosphino)ferrocene]dichloropalladium(II) or $Pd_2(dba_3)_2$/Xantphos or other catalytic system known by the person skilled in the art, in the presence of a base such as $Na_2CO_3$ or $K_3PO_4$ in a solvent such as dioxane or n-butanol at a temperature ranging from 80 to 120° C.

Alternatively, some compounds of general formula I-A to I-D may be prepared by a Suzuki coupling reaction of a chloropyridine intermediate IV-A to IV-D protected by a suitable group (PG) known from the person skilled in the art and a boronic acid (or its corresponding boronic ester or trifluoroborate salt) Ill, followed by protecting group removal.

Protection of intermediates II may for example be performed in the presence of SEM-Cl with a suitable base such as NaH in a solvent such as DMF at a temperature ranging from 0° C. to 25° C. The Suzuki reaction may then be performed as described above while the SEM protecting group may typically be removed in a 1 to 1 TFA/DCM mixture at room temperature or in any other conditions known by the person skilled in the art.

Compounds of formula III are commercially available or may be prepared according to any procedure known to the person skilled in the art.

Alternatively, some compounds of general formula I-A to I-D may be prepared by a Stille coupling reaction of a chloropyridine intermediate II-A to II-D or its protected version IV-A to IV-D and a trialkylstannyl derivative VI, such as a trimethylstannyl:

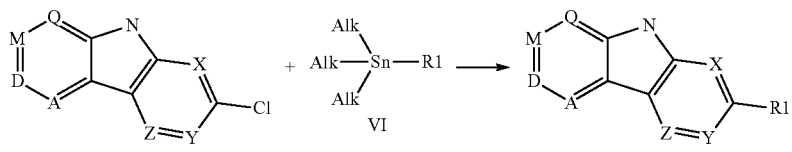

II-A to II-D                    I-A to I-D

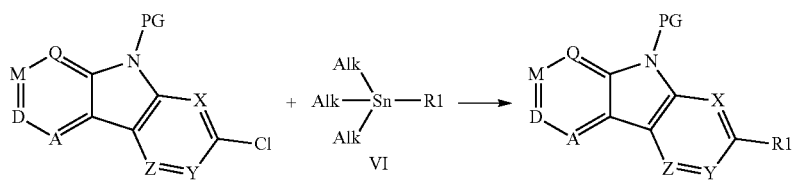

IV-A to IV-D                    V-A to V-D

This reaction may be performed in the presence of classical palladium catalytic systems such as Pd(PPh$_3$)$_4$ or other catalytic system known by the person skilled in the art, in a solvent such as DME at a temperature of about 100° C. The protecting group may be any suitable group know from the person skilled in the art, such as a SEM, and may be added or removed as described above.

Compounds of formula VI are commercially available or may be prepared according to any procedure known to the person skilled in the art.

According to one embodiment, some compounds of general formula I-A to I-D may be prepared by a nucleophilic substitution of a chloropyridine intermediate II-A to II-D or its protected version IV-A to IV-D by ammonia or a primary or secondary amine VII:

This reaction may be performed by heating a neat mixture of the chloro intermediate II or IV and the amine VII in a sealed tube at 220° C. for 30 min or by using any other conditions known by the person skilled in the art.

Amines of formula VII are commercially available or may be prepared according to any procedure known to the person skilled in the art.

Tricyclic chloro-intermediates of formula II-A to II-C may be prepared by Suzuki coupling of a suitable amino-iodo-pyridine VIII with the boronic acid IX, followed by intramolecular cyclization of intermediate X according to the equation:

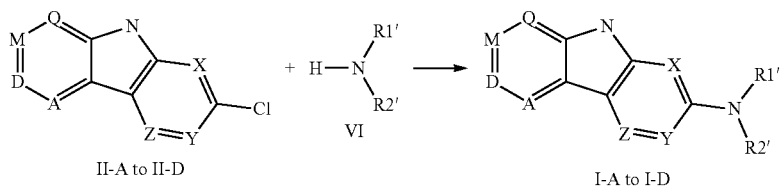

II-A to II-D                    I-A to I-D

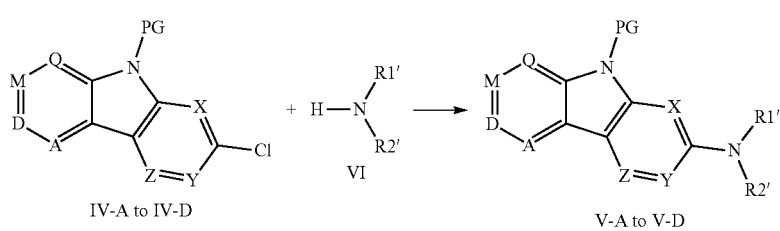

IV-A to IV-D                    V-A to V-D

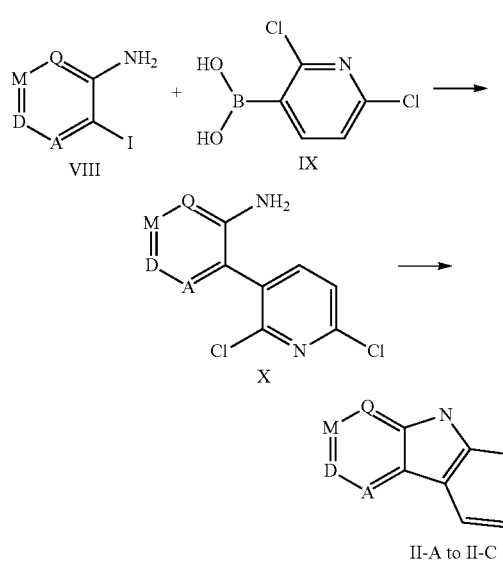

II-A to II-C

This Suzuki coupling reaction may be performed in the presence of classical palladium catalytic systems such as Bis(triphenylphosphine)palladium(II) dichloride or other catalytic system known by the person skilled in the art, in the presence of a base such as $Na_2CO_3$ or $K_3PO_4$ in a solvent such as dioxane or n-butanol at a temperature ranging from 80 to 120° C.

Iodopyridine of formula VIII are commercially available or may be prepared according to any procedure known to the person skilled in the art.

Boronic acid of formula IX is commercially available.

Intermediates of formula X may then be cyclized into compounds of formula II-A to II-C in the presence of a base such as LiHMDS or any similar base known from the person skilled in the art, in a solvent such as THF at a temperature of 90° C.

Alternatively, tricyclic chloro-intermediate of formula II-D may be prepared by Suzuki coupling of a suitable amino-iodo-pyridine VIII with the boronic acid XI, followed by intramolecular cyclization of intermediate XII according to the equation:

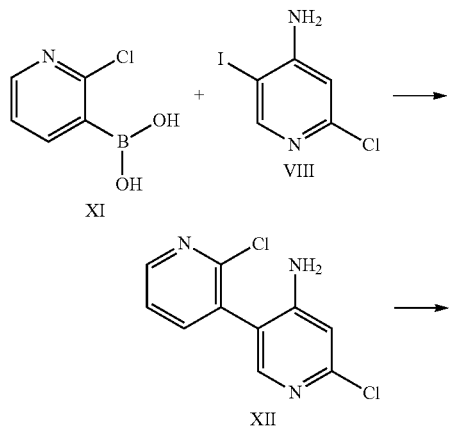

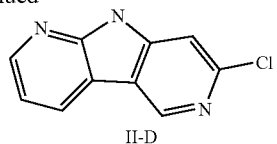

II-D

This Suzuki coupling reaction may be performed in the presence of classical palladium catalytic systems such as Bis(triphenylphosphine)palladium(II) dichloride or other catalytic system known by the person skilled in the art, in the presence of a base such as $Na_2CO_3$ or $K_3PO_4$ in a solvent such as dioxane or n-butanol at a temperature ranging from 80 to 120° C.

Iodopyridine of formula VIII are commercially available or may be prepared according to any procedure known to the person skilled in the art.

Boronic acid of formula XI is commercially available.

Intermediate of formula XII may then be cyclized into compounds of formula II-D in the presence of a base such as LiHMDS or any similar base known from the person skilled in the art, in a solvent such as THF at a temperature of 90° C.

The deuterated or tritiated compounds of formula I may be prepared by direct Hydrogen isotopic Exchange (HIE) using methods know from the people skilled in the art:

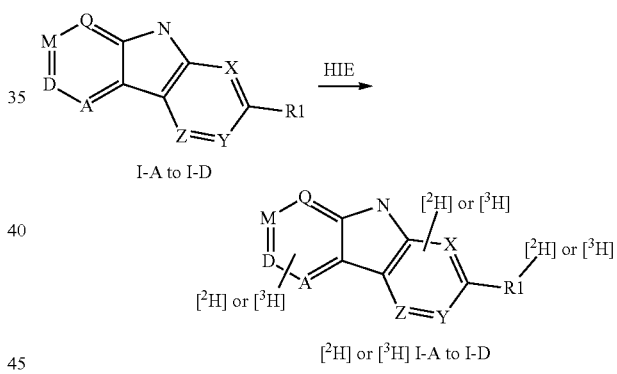

This HIE reaction may be performed in the presence of the well known Crabtree's iridium catalyst, [(COD)Ir(py)PCy$_3$]PF$_6$, Kerr's iridium-carbene catalysts or any similar catalyst known from the person skilled in the art, in a solvent such as THF or DMF in the presence of deuterium or tritium gas.

Alternatively, the deuterated or tritiated compounds of formula I may be prepared by reduction of the corresponding mono-, di- or tri-iodide or bromide using methods know from the people skilled in the art:

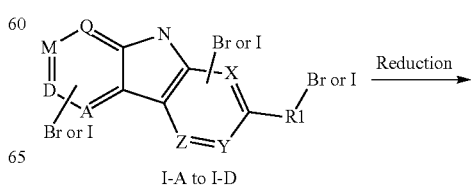

-continued

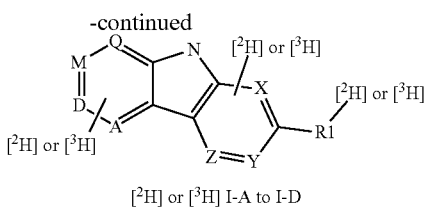

[²H] or [³H] I-A to I-D

This reduction reaction may be performed in the presence of various palladium catalysts or any similar catalyst known from the person skilled in the art, in a solvent such as THF or DMF in the presence of deuterium or tritium gas.

Alternatively, the deuterated or tritiated compounds of formula I may be prepared by a Suzuki coupling reaction of a deuterated or tritiated chloropyridine intermediate II-A to II-D and a boronic acid (or its corresponding boronic ester or trifluoroborate salt) III:

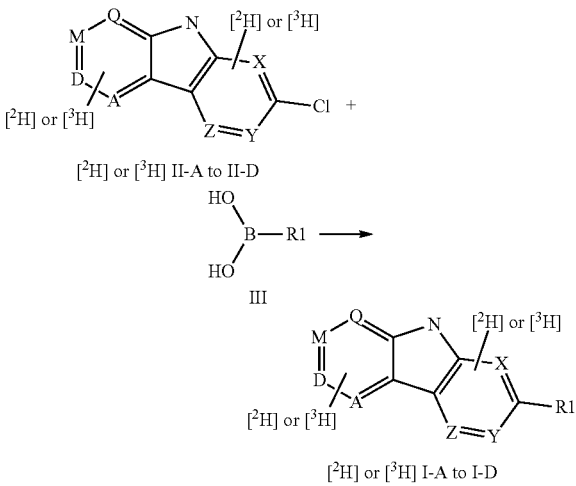

The deuterated or tritiated chloropyridine intermediates II-A to II-D may be prepared by any of the aforementioned methods.

Preparation of Compounds

Materials and Methods

Starting materials are either commercially available or can be prepared by methods analogous to the methods given below or by methods known in the art.

Compounds were named with the aid of ACD/Name Batch (Network) ver. 11.01

All reactions involving air- or moisture-sensitive reagents were performed under a nitrogen or argon atmosphere using dried solvents and glassware. Commercial solvents and reagents were generally used without further purification, including anhydrous solvents when appropriate (usually Sure-Seal™ products from Aldrich Chemical Company or AcroSeal™ from ACROS Organics). In general reactions were followed by thin layer chromatography, HPLC or mass spectrometry analyses.

Crude materials could be purified by normal phase chromatography, (acidic or basic) reverse phase chromatography, chiral separation or recrystallization.

Products were generally dried under vacuum before final analyses and submission to biological testing.

Tritium labeling of the compounds has been performed by Asclepia MedChem Solutions through direct hydrogen-tritium exchange according to the general method described hereafter.

HPLC Analysis

HPLC chromatograms are recorded as follows,
Method A: Acidic
HPLC analysis is performed with Shimadzu HPLC system equipped with LC-2010 CHT module, SPD-M20A photodiode array detector (210-400 nm), by using column YMC Triart C-18 (150×4.6) mm 3µ. Gradient elution is done with 5 mM ammonium formate in water+0.1% formic acid (Phase A), and Acetonitrile+5% solvent A+0.1% formic acid (Phase B), with gradient 5-95% B in 8.0 min hold till 13.0 min, 5% B at 15.0 min hold till 18.0 min. HPLC flow rate: 1.0 ml/min, injection volume: 10 µL.

Method B: Basic
HPLC analysis is performed with Shimadzu HPLC system equipped with LC-2010 CHT module, SPD-M20A photodiode array detector (210-400 nm), by using column YMC Triart C-18 (150×4.6) mm 3p. Gradient elution is done with 5 mM ammonium formate in water+0.1% Ammonia (Phase A), and Acetonitrile+5% solvent A+0.1% Ammonia (Phase B), with gradient 5-95% in 8.0 min hold till 13.0 min, 5% B at 15.0 min hold till 18.0 min. HPLC flow rate.

LCMS Analysis

LCMS analyses are performed as follows,
Method A: Acidic
Shimadzu 2010EV single quadrupole mass spectrometer is used for LC-MS analysis. This spectrometer is equipped with an ESI source and LC-20AD binary gradient pump, SPD-M20A photodiode array detector (210-400 nm). Data is acquired in a full MS scan from m/z 70 to 1200 in positive and negative mode. The reverse phase analysis is carried out by using Waters XBridge C 18 (30×2.1) mm 2.5µ column. Gradient elution is done with 5 mM ammonium formate in water+0.1% formic acid (Phase A) and Acetonitrile+5% solvent A+0.1% formic acid (Phase B), with gradient 5-95% B in 4.0 min hold till 5.0 min, 5% B at 5.1 min hold till 6.5 min. HPLC flow rate: 1.0 ml/min, injection volume: 5 µL.

MS parameters: Detector voltage 1.5 kV. Source block temperature 200° C. Desolvation temperature 240° C. nebulizing gas flow 1.2 L/min (Nitrogen). Data is acquired in a full MS scan from m/z 70 to 1200 in positive and negative mode.

Method B: Basic
Shimadzu 2010EV single quadrupole mass spectrometer is used for LC-MS analysis. This spectrometer is equipped with an ESI source and LC-20AD binary gradient pump, SPD-M20A photodiode array detector (210-400 nm). Data is acquired in a full MS scan from m/z 70 to 1200 in positive and negative mode. The reverse phase analysis is carried out by using Waters XBridge C 18 (30×2.1) mm 2.5µ column Gradient elution is done with 5 mM ammonium formate in water+0.1% Ammonia (solvent A), or Acetonitrile+5% solvent A+0.1% Ammonia (solvent B), with gradient 5-95% B in 4.0 min hold till 5.0 min, 5% B at 5.1 min hold till 6.5 min. HPLC flow rate: 1.0 ml/min, injection volume: 5 µL.

MS parameters: Detector voltage 1.5 kV. Source block temperature 200° C. Desolvation temperature 240° C. Nebulising gas flow 1.2 L/min (Nitrogen). Data is acquired in a full MS scan from m/z 70 to 1200 in positive and negative mode.

NMR

NMR spectra are recorded on a Varian MR 400 MHz NMR Spectrometer fitted with a Linux 3.2 software with operating system Redhat enterprise Linux 5.1. and 5 mm inverse $^1H/^{13}C$ probe head, or Varian VNMR 400 MHz NMR fitted with Linux 3.2 software with operating system Redhat enterprise Linux 6.3 and 5 mm inverse $^1H/^{13}C/^{19}F$ triple probe head. The compounds are studied in deuterated solvents such as DMSO-$d_6$, CDCl$_3$, MeOD or D$_2$O at a probe temperature of 300 K and at a concentration around 4-5 mg/mL. The instrument is locked on the deuterium signal of the deuterated solvent used. Chemical shifts are given in ppm downfield from TMS (tetramethylsilane) taken as internal standard.

Preparative Purification

Preparative purification is performed by using following systems in acidic basic and neutral condition.

A. Waters Prep HPLC System:
  Waters preparative HPLC equipped with binary pump 2545 module with 2998 PDA detector and comprising of 2767 sample manager. Waters 3100 single quadruple detector is used for detection and collection trigger.

B. Shimadzu Prep HPLC System:
  Shimadzu prep HPLC consists of binary LC8A pump and SPD M20A PDA detector with manual injection and manual fraction collection.

Purification is carried out by using following columns for above two systems:
  Phenomenex, Synergy Fusion C18, (100×30) mm, 4µ
  YMC ODS (500×30) mm 10µ.
  YMC Triart (250×30) mm 10µ.

C. Purification on SFC
  Thar SFC 100 preparative system comprised of 2545 co-solvent pump and Co2 pump, Column oven, 2767 autosampler and fraction collector, ABPR to maintain the pressure of system, 2998 PDA detector. System is controlled by Masslynx V4.1 software. Columns for SFC are selected among the ones listed below:
  Virdis, 2-Ethyl pyridine (250×30) mm, 5µ
  Virdis, CSH Fluro Phenyl (250×30) mm, 5µ
  Phenomenex Luna Hilic (250×30) mm, 5µ
  YMC, Cyano (250×19) mm, 5µ
  YMC, Diol (250×30) mm, 10µ
  Chiralpak IA (250×30) mm, 5µ

Abbreviations

ACN: Acetonitrile
AcOH: Acetic acid
BINAP: (2,2'-bis(diphenylphosphino)-1,1'-binaphthyl
Brine: Saturated aqueous sodium chloride solution
COD: 1,5-cyclooctadiene
DCM: Dichloromethane
DIPEA: Diisopropylethylamine
DMAP: 4-(Dimethylamino)pyridine
DMF: N,N-Dimethylformamide
DMSO: Dimethylsulfoxide
ES$^+$: Electrospray Positive Ionisation
EtOH: Ethanol
Et$_2$O: Diethyl ether
EtOAc: Ethyl acetate
ESI: Electrospray Ionization
h: Hour
HCl: Hydrochloric acid
HIE: Hydrogen Isotope Exchange
K$_2$CO$_3$: Potassium carbonate
LC: Liquid Chromatography
LCMS: Liquid Chromatography Mass Spectrometry
MeOH: Methanol
MgSO$_4$: Magnesium sulfate
min.: minutes
Na$_2$CO$_3$: Sodium carbonate
NaOH: Sodium hydroxide
Na$_2$SO$_4$: Sodium sulfate
NMR: Nuclear magnetic resonance
PdCl$_2$(dppf): [1,1'-Bis(diphenylphosphino)ferrocene]dichloropalladium(II)
Pd$_2$(dba)$_3$: Tris(dibenzylideneacetone)dipalladium(0)
PG: protecting group
iPrOH: isopropanol
PTSA: ptoluenesulfonic acid
py: pyridine
RCP: radiochemical Purity
RT: room temperature
SA: specific activity
SEM: [2-(Trimethylsilyl)ethoxy]methyl
SEM-Cl: [2-(Trimethylsilyl)ethoxy]methyl Chloride
TEA: Triethyl amine
TFA: Trifluoroacetic acid
THF: Tetrahydrofuran
TLC: Thin Layer Chromatography
Xantphos: 4,5-Bis(diphenylphosphino)-9,9-dimethylxanthene
Xphos: 2-Dicyclohexylphosphino-2',4',6'-triisopropylbiphenyl

EXAMPLES

The following examples illustrate how the compounds covered by formulas I and II may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Generic Synthetic Procedures

Procedure A: Suzuki Coupling
  To a solution of iodopyridine (1 eq) in dioxane (5 mL/mmol), the boronic acid (1.5 eq), and 1M Na$_2$CO$_3$ aqueous solution (3 eq) were added and the reaction mixture was degassed with argon for 20 min. Then Bis(triphenylphosphine)palladium(II) dichloride (0.2 eq) was added and the reaction mixture was heated at 100° C. for 16 h. After completion of reaction, the reaction mixture was filtered through a celite pad and the filtrate was concentrated under reduced pressure to afford a residue that was dissolved in water and extracted with ethyl acetate. The organic layer was separated, dried over sodium sulphate and concentrated under reduced pressure to afford the crude product, which was further purified by silica gel (100:200 mesh) column chromatography to afford the Suzuki coupling product.

Procedure B: Cyclization of Tricyclic Scaffolds
  To a solution of 2',6'-dichloro-[bipyridin]-amine (1 eq) in THF (10 mL/mmol), LiHMDS (12 eq) was added drop wise at 0° C. and the reaction mixture was heated at 90° C. for 2 h in a sealed tube. The reaction mixture was quenched with water and extracted with ethyl acetate. The organic layer was separated dried over sodium sulphate and concentrated under reduced pressure, which was purified by repeated washing with pentane to afford 2-chloro-9H-pyrrolo-dipyridine.

Procedure C: Suzuki Coupling

To a solution of 2-chloro-9H-pyrrolodipyridine (1 eq) in dioxane (5 mL/mmol), the corresponding boronic acid or boronic acid pinacol ester (1.3 eq) and 2M $Na_2CO_3$ solution (3.5 eq) were added and the reaction mixture was degassed with argon for 20 min. Then $PdCl_2(dppf)$ (0.2 eq) was added and the reaction mixture was heated until full conversion of starting material. After completion of the reaction, the reaction mixture was filtered through a celite pad and the filtrate was concentrated under reduced pressure. The residue was dissolved in water and extracted with 10% methanol in DCM. The organic layer was separated dried over sodium sulphate and concentrated under reduced pressure. The crude product was further purified by silica gel (100:200 mesh) column chromatography to afford the Suzuki coupling product.

Procedure D: Suzuki Coupling

To a solution of 2-chloro-9H-pyrrolodipyridine (1 eq) in dioxane:water (6 mL/mmol), the corresponding boronic acid or pinacol ester (1.3 eq), $K_3PO_4$ (3.0 eq) and X-phos (0.3 eq) were added and the reaction mixture was degassed with argon for 20 min. $Pd_2(dba)_3$ (0.1 eq) was added and the reaction mixture was heated at 110° C. for 12 h. The reaction mixture was filtered through a celite pad and the filtrate was concentrated under reduced pressure. The obtained residue was purified by silica gel column chromatography using 4% methanolic ammonia in DCM to afford the Suzuki coupling product.

Procedure E: SEM Protection

To a solution of 2-chloro-9H-pyrrolo-dipyridine (1 eq) in DMF (4 mL/mmol), NaH (1.2 eq) was added at 0° C. and the reaction mixture was stirred at the same temperature for 30 min. SEM-Cl (1.2 eq) was then added drop wise at 0° C. The reaction was stirred at room temperature for 3 h. The progress of the reaction was monitored by TLC. After completion, the mixture was quenched with water and extracted with ethyl acetate. The organic layer was separated, dried over sodium sulphate and concentrated under reduced pressure. The crude product was purified by silica gel (100-200 mesh) column chromatography using 2% methanol in dichloromethane as eluent to afford 2-chloro-9-((2-(trimethylsilyl)ethoxy)methyl)-9H-pyrrolo-dipyridine.

Procedure F: SEM Deprotection

To a solution of SEM protected 9H-pyrrolodipyridine (1 eq) in DCM (10 mL/mmol), TFA (10 mL/mmol) was added drop wise at 0° C. and the reaction was stirred at room temperature for 4 h. The progress of the reaction was monitored by TLC. After full conversion of the starting material, the reaction mixture was diluted with ammonium hydroxide, stirred at room temperature for 2 h. The precipitate was filtered, washed with water and dried under vacuum. The crude product was triturated with n-pentane to afford the desired unprotected product.

Procedure G: Suzuki Coupling

To a stirred solution of SEM protected 2-chloro-9H-pyrrolodipyridine (1 eq) in 1,4-dioxane:water (8:1, 15 mL/mmol), N-(2-methoxyethyl)-5-(4,4,5,5-tetramethyl-1,3,2-dioxaborolan-2-yl)pyrimidin-2-amine (1.2 eq) and $K_3PO_4$ (3 eq) were added and the reaction was degassed with argon for 20 min. $Pd_2(dba_3)_2$ (0.1 eq) and xantphos (0.2 eq) were added and the reaction was heated at 100° C. for 6 h. The progress of the reaction was monitored by TLC. After completion of the reaction, the solvent was removed under reduced pressure. The crude product was purified by silica gel (230:400 mesh) column chromatography using 2% methanol in dichloromethane as eluent to afford the Suzuki coupling product.

Procedure H: Synthesis of Boronic Esters

To a stirred solution of 5-bromo-N,N-dimethylpicolinamide (1 eq) in dioxane (4 mL/mmol), Bis(pinacolato)diboron (1.1 eq) and $K_2CO_3$ (3 eq) were added and the reaction was degassed with argon for 20 min. $PdCl_2(dppf)$ (0.025 eq) and dppf (0.05 eq) were added and the reaction was heated at 100° C. for about 16 h. The progress of the reaction was monitored by TLC. After completion, the reaction mixture was evaporated under reduced pressure. The crude product was purified by silica gel (basic) column chromatography using 2% methanol in dichloromethane as eluent to afford the desired pinacol boronic ester.

Procedure I: Nucleophilic Substitution with Amines 2-chloro-9H-pyrrolo[2,3-b:4,5-c']dipyridine (1.0 eq) and the appropriate amine amine (1.7 eq) were weighed in a sealed tube and the reaction mixture was heated at 220° C. for 30 min. Reaction mixture was allowed to cool to room temperature, then added methanol and heated to 80° C. for 10 min. The reaction mixture was quenched with water and extracted with ethyl acetate. The organic layer was separated dried over sodium sulphate and concentrated under reduced pressure, which was purified by repeated washing with acetonitrile, DCM and pentane to afford the desired product.

Procedure J: Synthesis of N-Linked Pyrazoles

To a stirred solution of 2-chloro-9-((2-(trimethylsilyl)ethoxy)methyl)-9H-pyrrolodipyridine (1 eq) and pyrazole (1.2 eq) and in DMSO (7.5 mL/mmol), CuI (1 eq) and $Cs_2CO_3$ (3 eq) were added and the reaction was heated at 90° C. for 8 h. The progress of the reaction was monitored by TLC. After completion of the reaction, water was added to the mixture which was then extracted with DCM. The organic layer was separated, dried and concentrated under reduced pressure to obtain crude product, which was purified by column chromatography using 6% methanolic ammonia in dichloromethane as eluent to afford the desired compound.

Procedure K: Tritium Labeling Procedure

This procedure exemplarily describes the preparation of [$^3$H]-labeled compounds by direct Hydrogen Isotope Exchange.

5 mg of the unlabeled compound and 6 mg of rhodium black were suspended in 0.9 ml of a mixture of THF and DMF (1/8). The suspension was degassed three times at the high vacuum manifold and stirred under an atmosphere of tritium gas (9 Ci) for 3 h at room temperature. The solvent was removed under vacuum, and labile tritium was exchanged by adding 1 ml of methanol, stirring the solution, and removing the solvent again under vacuum. This process was repeated three times. Finally, the well-dried solid was extracted with 5 ml of ethanol containing 0.1% of trifluoracetic acid. The suspension was filtered through a 0.2 μm nylon membrane, obtaining a clear solution.

Purification of 100 mCi (3.70 GBq) of the crude compound was performed on a Macherey+Nagel Nucleodur Gravity C18, 5 μm, 8×150 mm; solvents A: 10 mM NH4OAc; B: acetonitrile; 35% B; 254 nm and 220 nm; 3.1 ml/min; 20° C. to afford the radiolabeled product with a radiochemical purity >98%. The specific activity was determined for each synthesis.

Compounds of Formula I-A

Compounds of Formula I-A-1

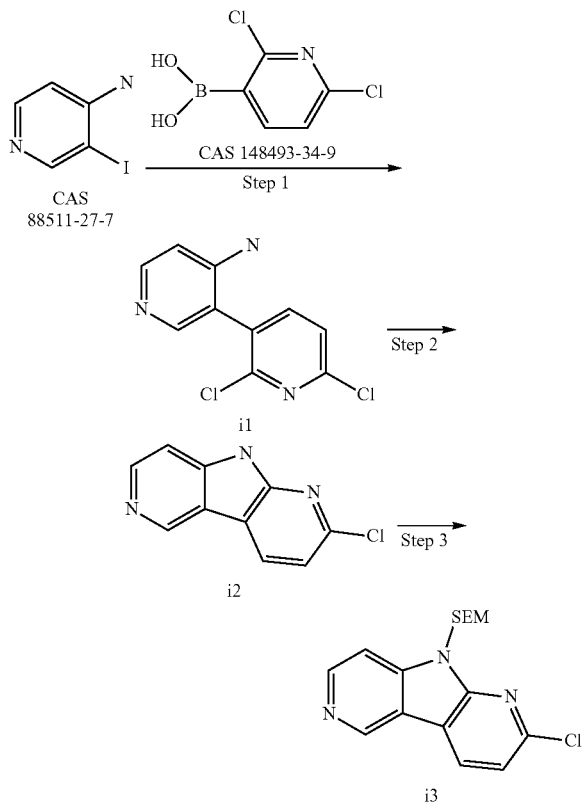

2',6'-dichloro-[3,3'-bipyridin]-4-amine (i1)

3-iodopyridin-4-amine (6 g, 27.2 mmol) was reacted with (2,6-dichloropyridin-3-yl)boronic acid (7.29 g, 38.1 mmol) according to procedure A to afford 2',6'-dichloro-[3,3'-bipyridin]-4-amine (i1) (2.9 g, Yield 44%).

$^1$H NMR (400 MHz, DMSO-$d_6$) δ 6.04 (s, 2H), 6.62 (d, J=5.8 Hz, 1H), 7.71-7.55 (m, 1H), 7.94-7.75 (m, 2H), 8.03 (d, J=5.7 Hz, 1H).

MS (ESI) m/e (M+1)$^+$: 240.05

2-chloro-9H-pyrrolo[2,3-b:4,5-c']dipyridine (i2)

Cyclization of 2',6'-dichloro-[3,3'-bipyridin]-4-amine (i1) (1 g, 8.0 mmol) in THF (100 mL) was performed according to procedure B to afford 2-chloro-9H-pyrrolo[2,3-b:4,5-c']dipyridine (i2) (1.5 g, Yield 89%).

$^1$H NMR (400 MHz, DMSO-$d_6$) δ 7.37 (d, J=8.1 Hz, 1H), 7.50 (d, J=5.6, 1.1 Hz, 1H), 8.49 (d, J=5.6 Hz, 1H), 8.66 (d, J=8.1 Hz, 1H), 9.37 (S, 1H), 12.45 (S, 1H).

MS (ESI) m/e (M+1)$^+$: 204.05

2-chloro-9-((2-(trimethylsilyl)ethoxy)methyl)-9H-pyrrolo[2,3-b:4,5-c']dipyridine (i3)

SEM protection of 2-chloro-9H-pyrrolo[2,3-b:4,5-c']dipyridine (i2) (0.5 g, 2.46 mmol) was performed according to generic procedure E to afford 2-chloro-9-((2-(trimethylsilyl)ethoxy)methyl)-9H-pyrrolo[2,3-b:4,5-c']dipyridine (i3) (0.26 g, Yield 31%).

$^1$H NMR (400 MHz, DMSO-$d_6$) δ −0.15 (s, 9H), 0.89-0.79 (m, 2H), 3.60-3.49 (m, 2H), 5.85 (s, 2H), 7.50 (d, J=8.1 Hz, 1H), 7.80 (d, J=5.7 Hz, 1H), 8.62 (d, J=5.7 Hz, 1H), 8.74 (d, J=8.1 Hz, 1H), 9.45 (s, 1H).

MS (ESI) m/e (M+1)$^+$: 334.35

Generic Reaction Scheme for Examples 1-12:

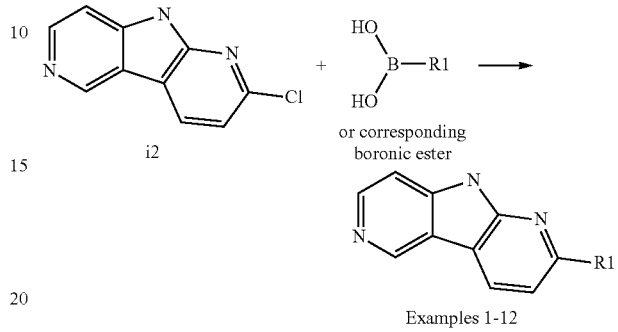

Example 1. 2-(pyridin-4-yl)-9H-pyrrolo[2,3-b:4,5-c']dipyridine 2-chloro-9H-pyrrolo[2,3-b:4,5-c']dipyridine (i2) (0.1 g, 0.49 mmol) was reacted with pyridin-4-ylboronic acid (0.078 g, 0.6 mmol) according to procedure C to afford 2-(pyridin-4-yl)-9H-pyrrolo[2,3-b:4,5-c']dipyridine (0.04 g, Yield 33%).

$^1$H NMR (400 MHz, DMSO-$d_6$) δ 7.51 (d, J=5.58 Hz, 1H) 8.09 (d, J=8.37 Hz, 1H) 8.16 (d, J=5.58 Hz, 2H) 8.52 (d, J=5.58 Hz, 1H) 8.73 (d, J=5.58 Hz, 2H) 8.79 (d, J=7.91 Hz, 1H) 9.43 (s, 1H) 12.45 (brs, 1H)

MS (ESI) m/e (M+1)$^+$: 247.09.

Example 2. 2-(2-methoxypyridin-4-yl)-9H-pyrrolo[2,3-b:4,5-c']dipyridine 2-chloro-9H-pyrrolo[2,3-b:4,5-c']dipyridine (i2) (0.1 g, 0.49 mmol) was reacted with (2-methoxypyridin-4-yl)boronic acid (0.097 g, 0.6 mmol) according to procedure C to afford 2-(2-methoxypyridin-4-yl)-9H-pyrrolo[2,3-b:4,5-c']dipyridine (0.018 g, Yield 14%).

$^1$H NMR (400 MHz, DMSO-$d_6$) δ 3.94 (s, 3H) 7.51 (d, J=5.29 Hz, 1H) 7.57 (s, 1H) 7.77 (d, J=5.29 Hz, 1H) 8.07 (d, J=8.38 Hz, 1H) 8.32 (d, J=4.85 Hz, 1H) 8.52 (d, J=5.29 Hz, 1H) 8.77 (d, J=7.94 Hz, 1H) 9.42 (s, 1H) 12.43 (brs, 1H)

MS (ESI) m/e (M+1)$^+$: 276.9.

Example 3. 2-(pyridin-3-yl)-9H-pyrrolo[2,3-b:4,5-c']dipyridine 2-chloro-9H-pyrrolo[2,3-b:4,5-c']dipyridine (i2) (0.1 g, 0.49 mmol) was reacted with pyridin-3-ylboronic acid (0.078 g, 0.6 mmol) according to procedure C to afford 2-(pyridin-3-yl)-9H-pyrrolo[2,3-b:4,5-c']dipyridine (0.04 g, Yield 33%).

$^1$H NMR (400 MHz, DMSO-$d_6$) δ 7.46-7.60 (m, 2H), 8.02 (d, J=8.1 Hz, 1H), 8.47-8.57 (m, 2H), 8.65 (dd, J=4.8, 1.6 Hz, 1H), 8.75 (d, J=8.1 Hz, 1H), 9.43-9.35 (m, 2H), 12.40 (s, 1H).

MS (ESI) m/e (M+1)$^+$: 247.0

Example 4. 2-(1-methyl-1H-pyrazol-4-yl)-9H-pyrrolo[2,3-b:4,5-c']dipyridine 2-chloro-9H-pyrrolo[2,3-b:4,5-c']dipyridine (i2) (0.1 g, 0.49 mmol) was reacted with 1-methyl-4-(4,4,5,5-tetramethyl-1,3,2-dioxaborolan-2-yl)-1H-pyrazole (0.133 g, 0.6 mmol) according to procedure C to afford 2-(pyridin-3-yl)-9H-pyrrolo[2,3-b:4,5-c']dipyridine (0.03 g, Yield 25%).

$^1$H NMR (400 MHz, DMSO-d$_6$) δ 3.92 (s, 3H), 7.43 (d, J=5.6 Hz, 1H), 7.61 (d, J=8.0 Hz, 1H), 8.07 (s, 1H), 8.34 (s, 1H), 8.44 (d, J=5.6 Hz, 1H), 8.56 (d, J=8.0 Hz, 1H), 9.29 (s, 1H), 12.17 (s, 1H),

MS (ESI) m/e (M+1)$^+$: 250.0

Example 5. 2-(6-methoxypyridin-3-yl)-9H-pyrrolo[2,3-b:4,5-c']dipyridine 2-chloro-9H-pyrrolo[2,3-b:4,5-c']dipyridine (i2) (0.1 g, 0.49 mmol) was reacted with 2-methoxy-5-(4,4,5,5-tetramethyl-1,3,2-dioxaborolan-2-yl)pyridine (0.15 g, 0.64 mmol) according to procedure C to afford 2-(6-methoxypyridin-3-yl)-9H-pyrrolo[2,3-b:4,5-c']dipyridine (0.035 g, Yield 26%).

$^1$H NMR (400 MHz, DMSO-d$_6$) δ 3.94 (s, 3H) 6.98 (d, J=8.84 Hz, 1H) 7.47 (d, J=5.58 Hz, 1H) 7.91 (d, J=8.37 Hz, 1H) 8.44-8.53 (m, 2H) 8.69 (d, J=7.91 Hz, 1H) 8.99 (d, J=2.33 Hz, 1H) 9.37 (s, 1H) 12.33 (s, 1H)

MS (ESI) m/e (M+1)$^+$: 276.9

Example 6. 5-(9H-pyrrolo[2,3-b:4,5-c']dipyridin-2-yl)pyridin-2-ol 2-chloro-9H-pyrrolo[2,3-b:4,5-c']dipyridine (i2) (0.1 g, 0.49 mmol) was reacted with 5-(4,4,5,5-tetramethyl-1,3,2-dioxaborolan-2-yl)pyridin-2-ol (0.141 g, 0.6 mmol) according to procedure C to afford 5-(9H-pyrrolo[2,3-b:4,5-c']dipyridin-2-yl)pyridin-2-ol (0.024 g, Yield 18%).

$^1$H NMR (400 MHz, DMSO-d$_6$) δ 6.50 (d, J=9.65 Hz, 1H) 7.55 (d, J=5.83 Hz, 1H) 7.82 (d, J=8.30 Hz, 1H) 8.26 (m, 1H) 8.30 (dd, J=9.65, 2.47 Hz, 1H) 8.50 (d, J=5.83 Hz, 1H) 8.65 (d, J=8.30 Hz, 1H) 9.40 (s, 1H) 11.95 (brs, 1H) 12.47 (brs, 1H)

MS (ESI) m/e (M+1)$^+$: 262.9

Example 7. 2-(5-fluoro-6-methoxypyridin-3-yl)-9H-pyrrolo[2,3-b:4,5-c']dipyridine To a solution of 2-chloro-9H-pyrrolo[2,3-b:4,5-c']dipyridine (i2) (0.1 g, 0.49 mmol) was reacted with (5-fluoro-6-methoxypyridin-3-yl)boronic acid (0.109 g, 0.6 mmol) according to procedure C to afford 2-(5-fluoro-6-methoxypyridin-3-yl)-9H-pyrrolo[2,3-b:4,5-c']dipyridine (0.03 g, Yield 21%).

$^1$H NMR (400 MHz, DMSO-d$_6$) δ 4.03 (s, 3H) 7.48 (d, J=5.58 Hz, 1H) 7.97 (d, J=7.91 Hz, 1H) 8.39 (d, J=12.10 Hz, 1H) 8.49 (d, J=5.58 Hz, 1H) 8.71 (d, J=8.37 Hz, 1H) 8.83 (s, 1H) 9.38 (s, 1H) 12.36 (brs, 1H)

MS (ESI) m/e (M+1)$^+$:294.9

Example 8. 2-(furan-3-yl)-9H-pyrrolo[2,3-b:4,5-c']dipyridine 2-chloro-9H-pyrrolo[2,3-b:4,5-c']dipyridine (i2) (0.1 g, 0.49 mmol) was reacted with furan-3-ylboronic acid (0.071 g, 0.6 mmol) according to procedure C to afford 2-(furan-3-yl)-9H-pyrrolo[2,3-b:4,5-c']dipyridine (0.051 g, Yield 55%).

$^1$H NMR (400 MHz, DMSO-d$_6$) δ 7.14 (s, 1H), 7.40-7.44 (m, 1H), 7.64-7.68 (m, 1H), 7.79-7.81 (m, 1H), 8.40-8.49 (m, 2H), 8.60-8.62 (m, 1H), 9.33 (s, 1H), 12.26 (s, 1H).

MS (ESI) m/e (M+1)$^+$: 236

Example 9. 2-(1H-pyrazol-4-yl)-9H-pyrrolo[2,3-b:4,5-c']dipyridine

To a solution of 2-chloro-9H-pyrrolo[2,3-b:4,5-c']dipyridine (i2) (0.1 g, 0.49 mmol) in n-butanol (5 mL), 4-(4,4,5,5-tetramethyl-1,3,2-dioxaborolan-2-yl)-1H-pyrazole (0.141 g, 0.64 mmol), K$_3$PO$_4$ (0.313 mL, 1.4 mmol) and X-phos (0.07 g, 0.14 mmol) were added and the reaction mixture was degassed with argon for 20 min. Pd$_2$(dba)$_3$ (0.045 g, 0.049 mmol) was added and the reaction mixture was heated at 110° C. for 12 h. The reaction mixture was filtered through celite and the filtrate was concentrated under reduced pressure to obtain a residue which was dissolved in water and extracted with 10% methanol in DCM. The organic layer was separated dried over sodium sulphate and concentrated under reduced pressure. The residue obtained was purified by silica gel column chromatography using 2% methanolic ammonia in DCM to afford 2-(1H-pyrazol-4-yl)-9H-pyrrolo[2,3-b:4,5-c']dipyridine (10 mg, Yield 8.6%).

$^1$H NMR (400 MHz, DMSO-d$_6$) δ 7.42 (d, J=5.58 Hz, 1H) 7.67 (d, J=7.91 Hz, 1H) 8.14 (brs, 1H) 8.40 (brs, 1H) 8.43 (d, J=5.58 Hz, 1H) 8.56 (d, J=7.91 Hz, 1H) 9.30 (s, 1H) 12.19 (s, 1H) 13.10 (brs, 1H).

MS (ESI) m/e (M+1)$^+$: 236.0.

Example 10. 4-(5-(9H-pyrrolo[2,3-b:4,5-c']dipyridin-2-yl)pyrimidin-2-yl)morpholine 2-chloro-9H-pyrrolo[2,3-b:4,5-c']dipyridine (i2) (0.1 g, 0.49 mmol) was reacted with (2-morpholinopyrimidin-5-yl)boronic acid (0.186 g, 0.64 mmol) according to procedure D to afford 4-(5-(9H-pyrrolo[2,3-b:4,5-c']dipyridin-2-yl)pyrimidin-2-yl)morpholine (0.055 g, Yield 48%).

$^1$H NMR (400 MHz, DMSO-d$_6$) δ 3.70 (brs, 4H) 3.81 (brs, 4H) 7.45 (d, J=4.49 Hz, 1H) 7.86 (d, J=7.85 Hz, 1H) 8.47 (d, J=4.26 Hz, 1H) 8.66 (d, J=7.63 Hz, 1H) 9.16 (brs, 2H) 9.35 (brs, 1H) 12.32 (brs, 1H).

MS (ESI) m/e (M+1)$^+$: 332.9

Example 11. N-methyl-5-(9H-pyrrolo[2,3-b:4,5-c']dipyridin-2-yl)pyridine-2-carboxamide 2-chloro-9H-pyrrolo[2,3-b:4,5-l]dipyridine (i2) (0.1 g, 0.49 mmol) was reacted with N-methyl-5-(4,4,5,5-tetramethyl-1,3,2-dioxaborolan-2-yl)picolinamide (0.167 g, 0.64 mmol) according to procedure D to afford N-methyl-5-(9H-pyrrolo[2,3-b:4,5-c']dipyridin-2-yl)pyridine-2-carboxamide (0.04 g, Yield 27%).

$^1$H NMR (400 MHz, DMSO-d$_6$) δ 2.86 (d, J=4.49 Hz, 3H) 7.50 (d, J=5.83 Hz, 1H) 8.12 (d, J=8.08 Hz, 1H) 8.18 (d, J=8.08 Hz, 1H) 8.52 (d, J=5.39 Hz, 1H) 8.72 (dd, J=8.08, 1.35 Hz, 1H) 8.79 (d, J=8.08 Hz, 1H) 8.86 (d, J=4.94 Hz, 1H) 9.36-9.50 (m, 2H) 12.46 (s, 1H)

MS (ESI) m/e (M+1)$^+$: 303.9

Example 12. 3-fluoro-5-(9H-pyrrolo[2,3-b:4,5-c']dipyridin-2-yl)pyridin-2-amine 2-chloro-9H-pyrrolo[2,3-b:4,5-l]dipyridine (i2) (0.1 g, 0.49 mmol) was reacted with 3-fluoro-5-(4,4,5,5-tetramethyl-1,3,2-dioxaborolan-2-yl)pyridin-2-amine (0.152 g, 0.64 mmol) according to procedure D to afford 3-fluoro-5-(9H-pyrrolo[2,3-b:4,5-c']dipyridin-2-yl)pyridin-2-amine (0.013 g, Yield 10%).

$^1$H NMR (400 MHz, DMSO-d$_6$) δ 6.61 (s, 2H) 7.52 (d, J=5.61 Hz, 1H) 7.88 (d, J=8.08 Hz, 1H) 8.09-8.12 (m, 1H) 8.49 (d, J=5.61 Hz, 1H) 8.61-8.72 (m, 2H) 9.39 (s, 1H) 12.41 (brs, 1H) MS (ESI) m/e (M+1)$^+$: 279.9

Generic Reaction Scheme for Examples 13-14:

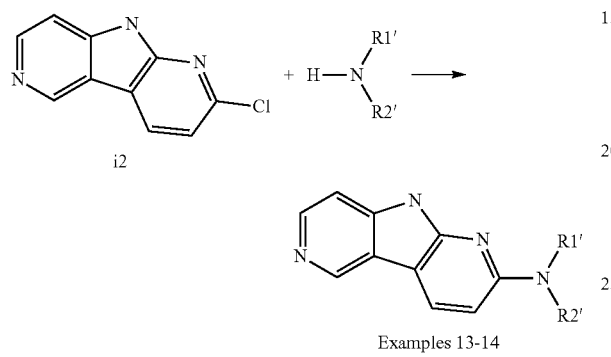

Examples 13-14

Example 13. 2-(4-(pyrimidin-2-yl)piperazin-1-yl)-9H-pyrrolo[2,3-b:4,5-c']dipyridine 2-chloro-9H-pyrrolo[2,3-b:4,5-c']dipyridine (i2) (0.07 g, 0.3 mmol) and 2-(piperazin-1-yl)pyrimidine (0.084 g, 0.51 mmol) were reacted according to procedure I to afford 2-(4-(pyrimidin-2-yl)piperazin-1-yl)-9H-pyrrolo[2,3-b:4,5-c']dipyridine (0.023 g, Yield 20%).

$^1$H NMR (400 MHz, DMSO-d$_6$) δ 3.66-3.80 (m, 4H) 3.83-4.00 (m, 4H) 6.67 (t, J=4.71 Hz, 1H) 6.86 (d, J=8.98 Hz, 1H) 7.31 (d, J=5.39 Hz, 1H) 8.28-8.36 (m, 2H) 8.41 (d, J=4.94 Hz, 2H) 9.10 (s, 1H) 11.82 (s, 1H)

MS (ESI) m/e (M+1)$^+$: 332.1

Example 14. 2-(4-(pyridin-4-yl)piperazin-1-yl)-9H-pyrrolo[2,3-b:4,5-c']dipyridine 2-chloro-9H-pyrrolo[2,3-b:4,5-c']dipyridine (i2) (0.07 g, 0.3 mmol) and 1-(pyridin-4-yl)piperazine (0.084 g, 0.51 mmol) were reacted according to procedure I to afford 2-(4-(pyridin-4-yl)piperazin-1-yl)-9H-pyrrolo[2,3-b:4,5-c']dipyridine (0.010 g, Yield 9%)

$^1$H NMR (400 MHz, DMSO-d$_6$) δ 3.16 (s, 4H), 3.77 (s, 4H), 6.80-6.87 (m, 3H), 7.32 (d, J=5.5 Hz, 1H), 8.16-32 (m, 4H), 9.10 (s, 1H), 11.80 (s, 1H),

MS (ESI) m/e (M+1)$^+$: 331.2

Example 15. 2-(1H-pyrazol-3-yl)-9H-pyrrolo[2,3-b:4,5-c']dipyridine

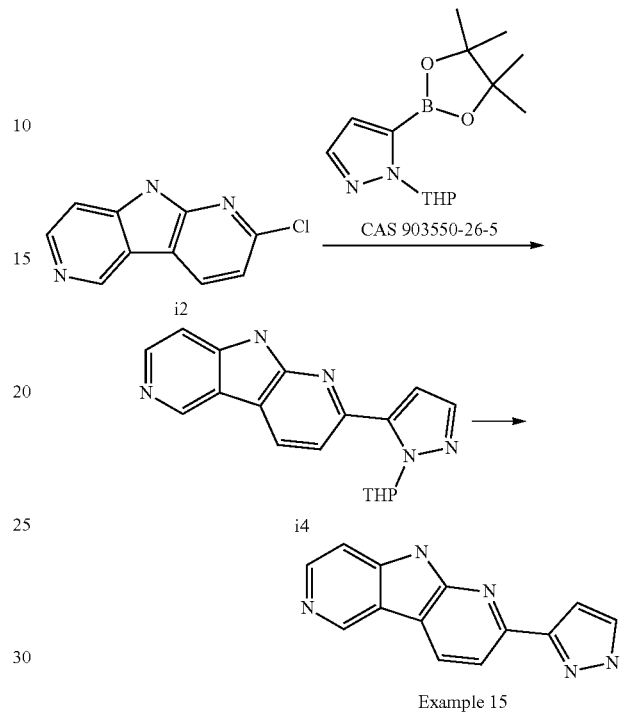

Example 15

2-(1-(tetrahydro-2H-pyran-2-yl)-1H-pyrazol-5-yl)-9H-pyrrolo[2,3-b:4,5-c']dipyridine (i4)

To a stirred suspension of 1-(tetrahydro-2H-pyran-2-yl)-5-(4,4,5,5-tetramethyl-1,3,2-dioxaborolan-2-yl)-1H-pyrazole (0.306 g, 1.1 mmol), 2-chloro-9H-pyrrolo[2,3-b:4,5-c']dipyridine (i2) (0.15 g, 0.7 mmol), KF (0.17 g, 2.9 mmol) and X-phos (0.069, 0.14 mmol) in n-butanol (10 mL), argon was purged for 15 min and Pd$_2$(dba)$_3$ (0.067 g, 0.07 mmol) was added. The reaction was heated at 100° C. for 16 h in a sealed tube. The progress of the reaction was monitored by TLC. After completion of the reaction, the solvent was evaporated under reduced pressure to obtain a crude product which was further purified by column chromatography on silica gel (100-200 mesh) using 4% methanol in dichloromethane to afford 2-(1-(tetrahydro-2H-pyran-2-yl)-1H-pyrazol-5-yl)-9H-pyrrolo[2,3-b:4,5-c']dipyridine (i4) (0.08 g, Yield 34%).

MS (ESI) m/e (M+1)$^+$: 320

2-(1H-pyrazol-3-yl)-9H-pyrrolo[2,3-b:4,5-c']dipyridine (Example 15)

2-(1-(tetrahydro-2H-pyran-2-yl)-1H-pyrazol-5-yl)-9H-pyrrolo[2,3-b:4,5-c']dipyridine (i4) (0.08 g, 0.25 mmol) was cooled to 0° C. and dioxane/HCl (2 mL; 4M HCl in dioxane) was added. The reaction was stirred at room temperature for 2 h. After completion of the reaction, the solvent was removed under reduced pressure to obtain an HCl salt of the desired product, which was further passed through strata column to obtain desired compound as a free amine, which was then purified by trituration with acetonitrile and methanol to afford 2-(1H-pyrazol-3-yl)-9H-pyrrolo[2,3-b:4,5-c']dipyridine (0.016 g, Yield 28%).

$^1$H NMR (400 MHz, DMSO-d$_6$) δ 6.91 (d, J=2.21 Hz, 1H) 7.46 (d, J=5.29 Hz, 1H) 7.79 (brs, 1H) 7.93 (d, J=7.94 Hz, 1H) 8.46 (d, J=5.6 Hz, 1H), 8.64 (d, J=7.94 Hz, 1H) 9.34 (s, 1H) 12.26 (brs, 1H) 13.18 (brs, 1H)

MS (ESI) m/e (M+1)$^+$: 236.0

Example 16. 4-(9H-pyrrolo[2,3-b:4,5-c']dipyridin-2-yl)pyridin-2-amine

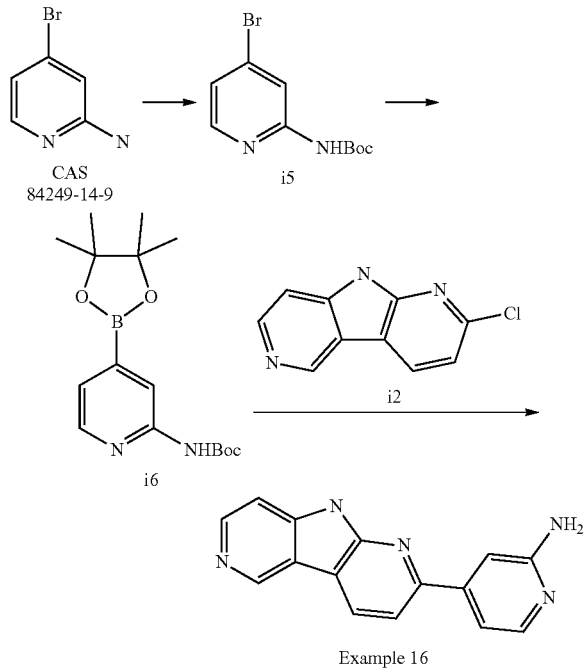

Example 16 tert-butyl (4-bromopyridin-2-yl)carbamate (i5)

To a stirred solution of 4-bromopyridin-2-amine (1 g, 5.7 mmol) in n-butanol (15 mL), boc-anhydride (1.7 mL, 6.9 mmol) was added and the reaction was heated at 50° C. for 16 h. The progress of the reaction was monitored by TLC. After completion of the reaction, the solvent was removed under reduced pressure to obtain a residue. The residue was dissolved in ethyl acetate and washed with water. The organic layer was dried over sodium sulphate and concentrated under reduced pressure to afford tert-butyl (4-bromopyridin-2-yl)carbamate (i5) (1.4 g, Yield 89%).

MS (ESI) m/e (M+1)$^+$: 273 tert-butyl (4-(4,4,5,5-tetramethyl-1,3,2-dioxaborolan-2-yl)pyridin-2-yl)carbamate (i6)

To a stirred suspension of tert-butyl (4-bromopyridin-2-yl)carbamate (i5) (0.5 g, 1.8 mmol), 4,4,4',4',5,5,5',5'-octamethyl-2,2'-bi(1,3,2-dioxaborolane) (1.4 g, 5.5 mmol), potassium acetate (0.541 g, 5.5 mmol) in DMSO (8 mL), argon was purged for 15 min and PdCl$_2$ (dppf) (0.15 g, 0.18 mmol) was added. The reaction was heated at 85° C. for 1 h in a sealed tube. The progress of the reaction was monitored by TLC. After completion, the reaction mixture was diluted with ethyl acetate washed with 0.2 M HCl solution. The organic layer was dried over sodium sulphate and concentrated under reduced pressure to afford tert-butyl (4-(4,4,5,5-tetramethyl-1,3,2-dioxaborolan-2-yl)pyridin-2-yl)carbamate (i6) (1.5 g, crude), compound was used as such in the next reaction.

4-(9H-pyrrolo[2,3-b:4,5-c']dipyridin-2-yl)pyridin-2-amine (Example 16)

To a stirred suspension of 2-chloro-9H-pyrrolo[2,3-b:4,5-c']dipyridine (i2) (0.15 g, 0.73 mmol) in THF (13.5 mL) and water (1.5 mL), tert-butyl (4-(4,4,5,5-tetramethyl-1,3,2-dioxaborolan-2-yl)pyridin-2-yl)carbamate (i6) (0.945 g, 2.9 mmol), and Cs$_2$CO$_3$ (0.72 g, 2.2 mmol) were added and argon was purged through the reaction mixture for 15 min. PdCl$_2$(dppf) (0.06 g, 0.07 mmol) was then added and argon was purged through the reaction mixture for further 15 min. The reaction was heated at 100° C. for 16 h in a sealed tube. The progress of the reaction was monitored by TLC and LCMS. After 16 h of heating, LCMS showed mass corresponding to Boc deprotected compound. At this point, the reaction was diluted with 10% methanol in dichloromethane and washed with water. The organic layer was dried over sodium sulphate and concentrated under reduced pressure. The crude product was purified by preparative HPLC to afford 4-(9H-pyrrolo[2,3-b:4,5-c']dipyridin-2-yl)pyridin-2-amine as a bisformate salt (0.013 g, Yield 7%).

$^1$H NMR (400 MHz, DMSO-d$_6$) δ 6.06 (brs, 2H) 7.19-7.26 (m, 2H) 7.50 (d, J=5.73 Hz, 1H) 7.86 (d, J=7.94 Hz, 1H) 8.04 (d, J=5.29 Hz, 1H), 8.38 (s, 2H bisformate), 8.50 (d, J=5.7 Hz, 1H) 8.72 (d, J=7.94 Hz, 1H) 9.39 (s, 1H), 12.4 (brs, 1H).

MS (ESI) m/e (M+1)$^+$: 262

Example 17. 4-(9H-pyrrolo[2,3-b:4,5-c']dipyridin-2-yl)pyridin-2-ol

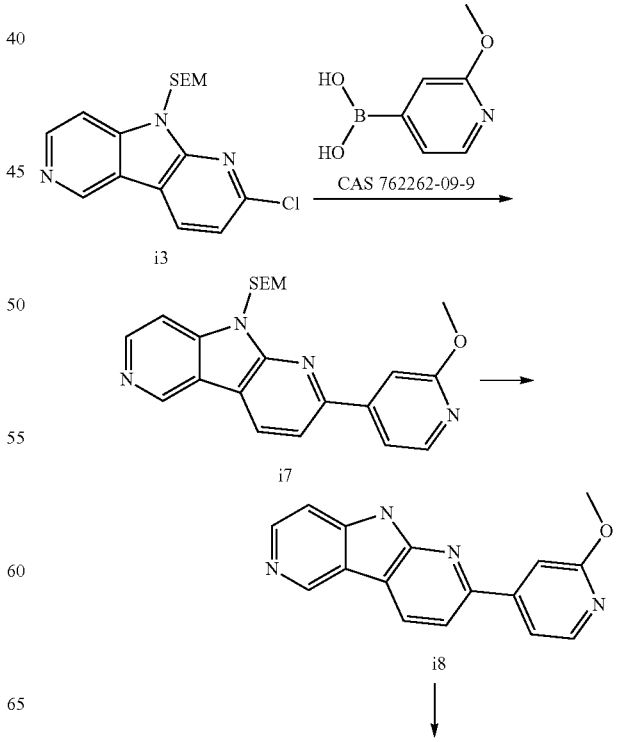

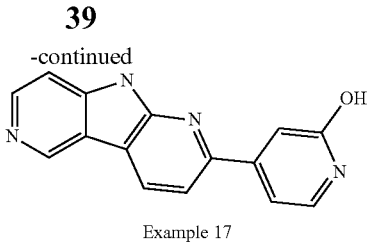

Example 17

2-(2-methoxypyridin-4-yl)-9-((2-(trimethylsilyl)ethoxy)methyl)-9H-pyrrolo[2,3-b:4,5-c']dipyridine (i7)

2-chloro-9-((2-(trimethylsilyl)ethoxy)methyl)-9H-pyrrolo[2,3-b:4,5-c']dipyridine (i3) (0.15 g, 0.45 mmol) was reacted with (2-methoxypyridin-4-yl)boronic acid (0.108 g, 0.66 mmol) according to procedure D to afford 2-(2-methoxypyridin-4-yl)-9-((2-(trimethylsilyl)ethoxy)methyl)-9H-pyrrolo[2,3-b:4,5-c']dipyridine (i7) (0.085 g, Yield 47%).

$^1$H NMR (400 MHz, DMSO-$d_6$) δ −0.20 (s, 9H), 0.90 (t, J=8.0 Hz, 2H), 3.60 (t, J=8.1 Hz, 2H), 3.94 (s, 3H), 7.67 (s, 1H), 6.00 (s, 2H), 7.78 (d, J=5.7 Hz, 1H), 7.85 (d, J=5.4 Hz, 1H), 8.17 (d, J=8.1 Hz, 1H), 8.33 (d, J=5.4 Hz, 1H), 8.62 (d, J=5.7 Hz, 1H), 8.82 (d, J=8.1 Hz, 1H), 9.47 (s, 1H).

MS (ESI) m/e (M+1)$^+$: 407.00

2-(2-methoxypyridin-4-yl)-9H-pyrrolo[2,3-b:4,5-c']dipyridine

SEM deprotection of 2-(2-methoxypyridin-4-yl)-9-((2-(trimethylsilyl)ethoxy)methyl)-9H-pyrrolo[2,3-b:4,5-c']dipyridine (i7) (0.07 g, 0.17 mmol) was performed according to procedure F to afford 2-(2-methoxypyridin-4-yl)-9H-pyrrolo[2,3-b:4,5-c']dipyridine (i8) (0.035 g, Yield 76%).

$^1$H NMR (400 MHz, DMSO-$d_6$) δ 3.94 (s, 3H), 7.50 (d, J=5.8 Hz, 1H), 7.57 (s, 1H), 7.77 (d, J=5.4 Hz, 1H), 8.07 (d, J=8.1 Hz, 1H), 8.32 (d, J=5.4 Hz, 1H), 8.52 (d, J=5.7 Hz, 1H), 8.76 (d, J=8.1 Hz, 1H), 9.42 (s, 1H), 12.42 (s, 1H).

MS (ESI) m/e (M+1)$^+$: 277.00

4-(9H-pyrrolo[2,3-b:4,5-c']dipyridin-2-yl)pyridin-2-ol (Example 17)

A stirred solution of 2-(2-methoxypyridin-4-yl)-9H-pyrrolo[2,3-b:4,5-c']dipyridine (i8) (0.03 g, 0.1 mmol) in HBr (4 mL) was heated at 120° C. for 30 min. The progress of the reaction was monitored by TLC. After completion, the mixture was basified to pH 9 using a saturated sodium bicarbonate solution. The precipitated solid was filtered, washed with water, dried under vacuum and washed with acetonitrile and n-pentane. The crude product was purified with strata column to afford 4-(9H-pyrrolo[2,3-b:4,5-c']dipyridin-2-yl)pyridin-2-ol (0.014 g, Yield 54%).

$^1$H NMR (400 MHz, DMSO-$d_6$) δ 6.98 (d, J=6.8 Hz, 1H), 7.12 (s, 1H), 7.48-7.56 (m, 2H), 7.99 (d, J=7.9 Hz, 1H), 8.53 (d, J=5.7 Hz, 1H), 8.75 (d, J=7.8 Hz, 1H), 9.44 (s, 1H), 11.67 (s, 1H), 12.50 (s, 1H)

MS (ESI) m/e (M+1)$^+$: 263.15

Example 18. 2-(5-fluoropyridin-2-yl)-9H-pyrrolo[2,3-b:4,5-c']dipyridine

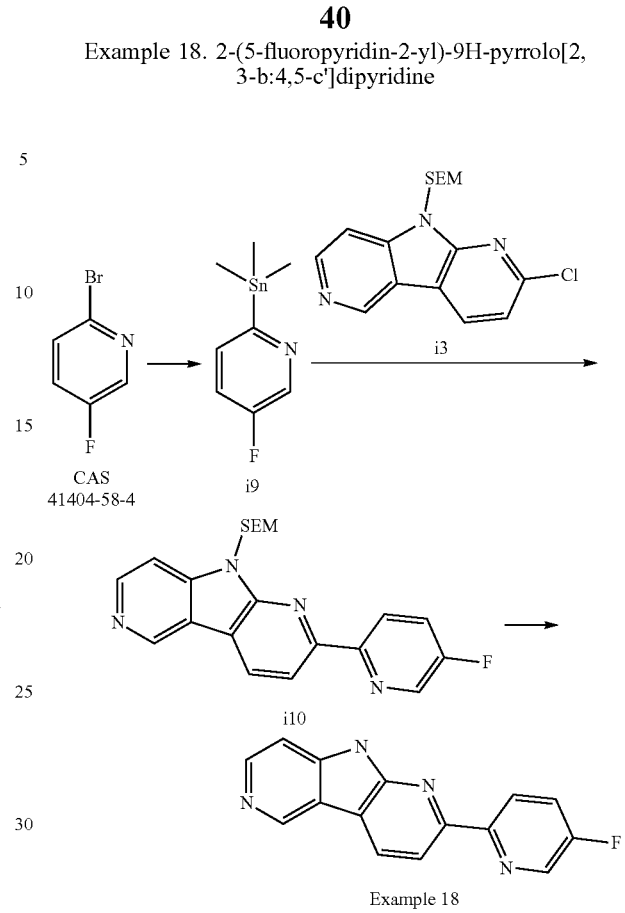

Example 18

5-fluoro-2-(trimethylstannyl)pyridine (i9)

To a stirred solution of 2-bromo-5-fluoropyridine (0.6 g, 3.40 mmol) in DME (60 mL), Pd(PPh$_3$)$_4$ (0.196 g, 0.17 mmol) and hexamethylditin (1.11 g, 3.40 mmol) were added and the mixture was heated at 100° C. for 3 h. The progress of the reaction was monitored by TLC. After completion, the reaction mixture was used as such for next step without any further purification and characterization.

2-(5-fluoropyridin-2-yl)-9-((2-(trimethylsilyl)ethoxy)methyl)-9H-pyrrolo[2,3-b:4,5-c']dipyridine (i10)

To a stirred solution of 5-fluoro-2-(trimethylstannyl)pyridine (i9) (0.6 g, 3.60 mmol) in DME (60 mL), 2-chloro-9-((2-(trimethylsilyl)ethoxy)methyl)-9H-pyrrolo[2,3-b:4,5-c']dipyridine (i3) (0.4 g, 1.2 mmol) and Pd(PPh$_3$)$_4$ (0.069 g, 0.06 mmol) were added and the reaction was purged with argon for 15 min then heated at 100° C. for 16 h. The progress of the reaction was monitored by TLC. After completion, the mixture was concentrated under reduced pressure. The crude product was purified by silica gel (230-400 mesh) column chromatography using 2% methanol in dichloromethane as eluent to afford 2-(5-fluoropyridin-2-yl)-9-((2-(trimethylsilyl)ethoxy)methyl)-9H-pyrrolo[2,3-b:4,5-c']dipyridine (i10) (0.32 g, Yield 68%).

$^1$H NMR (400 MHz, DMSO-$d_6$) δ −0.24 (m, 9H), 0.88 (t, J=8.0 Hz, 2H), 3.61 (t, J=8.0 Hz, 2H), 6.01 (s, 2H), 7.79 (d, J=5.7 Hz, 1H), 7.92-7.98 (m, 1H), 8.42 (dd, J=8.1, 1.7 Hz, 1H), 8.56-8.78 (m, 3H), 8.81 (dd, J=8.0, 1.9 Hz, 1H), 9.46 (s, 1H).

MS (ESI) m/e (M+1)$^+$: 395.36

2-(5-fluoropyridin-2-yl)-9H-pyrrolo[2,3-b:4,5-c'] dipyridine (Example 18)

SEM deprotection of 2-(5-fluoropyridin-2-yl)-9-((2-(trimethylsilyl)ethoxy)methyl)-9H-pyrrolo[2,3-b:4,5-c'] dipyridine (i10) (0.15 g, 0.38 mmol) was performed according to procedure F to afford 2-(5-fluoropyridin-2-yl)-9H-pyrrolo[2,3-b:4,5-c']dipyridine (0.045 g, Yield 45%).

$^1$H NMR (400 MHz, DMSO-d$_6$) δ 7.50 (d, J=5.29 Hz, 1H) 7.92 (t, J=8.16 Hz, 1H) 8.34 (d, J=8.38 Hz, 1H) 8.48-8.57 (m, 2H) 8.69-8.80 (m, 2H) 9.40 (s, 1H) 12.38 (brs, 1H)

MS (ESI) m/e (M+1)$^+$: 265.15

Example 19. 2-fluoro-5-(9H-pyrrolo[2,3-b:4,5-c'] dipyridin-2-yl)pyridin-3-amine

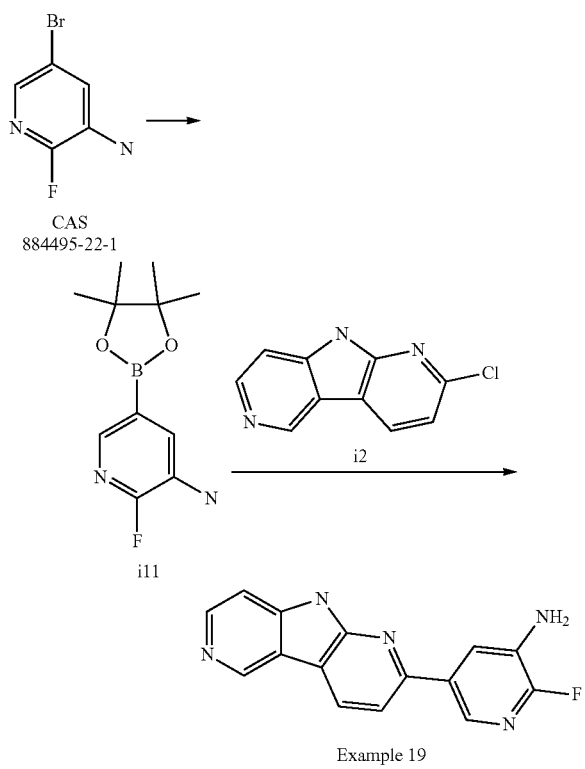

Example 19

2-fluoro-5-(4,4,5,5-tetramethyl-1,3,2-dioxaborolan-2-yl)pyridin-3-amine (i11)

To a stirred suspension of 5-bromo-2-fluoropyridin-3-amine (0.5 g, 2.6 mmol) in 1,4-dioxane (20 mL), 4,4,4',4',5,5,5',5'-octamethyl-2,2'-bi(1,3,2-dioxaborolane) (1.66 g, 6.5 mmol) and Cs$_2$CO$_3$ (2.12 g, 6.5 mmol) were added and the reaction mixture was degassed with argon for 15 min. Then Pd(PPh$_3$)$_4$ (0.155 g, 0.13 mmol) was added and the reaction mixture was further purged with argon for 15 min and heated at 100° C. for 4 h. The progress of the reaction was monitored by TLC. After completion, the reaction mixture was filtered through celite and the filtrate was concentrated under reduced pressure to afford 2-fluoro-5-(4,4,5,5-tetramethyl-1,3,2-dioxaborolan-2-yl)pyridin-3-amine (i11) which was used as such without any purification and characterization (0.62 g crude).

2-fluoro-5-(9H-pyrrolo[2,3-b:4,5-c']dipyridin-2-yl) pyridin-3-amine (Example 19)

To a stirred suspension of 2-chloro-9H-pyrrolo[2,3-b:4,5-c']dipyridine (i2) (0.150 g, 0.73 mmol), in 1,4-dioxane:water (6 mL) 2-fluoro-5-(4,4,5,5-tetramethyl-1,3,2-dioxaborolan-2-yl)pyridin-3-amine (i11) (1.05 mmol), K$_3$PO$_4$ (0.234 g, 1.1 mmol) and Pd$_2$(dba)$_3$ (0.033 g, 0.036 mmol) were added and the reaction mixture was degassed with argon for 20 min. The reaction was heated at 120° C. for 10 h. The progress of the reaction was monitored by TLC. After completion of reaction, the reaction mixture was absorbed on silica gel (230-400 mesh) and purified by combi flash column chromatography (4 g column) using 8% methanol in dichloromethane as eluent to afford 2-fluoro-5-(9H-pyrrolo [2,3-b:4,5-c']dipyridin-2-yl)pyridin-3-amine (0.007 g, Yield 3%).

$^1$H NMR (400 MHz, CD$_3$OD δ 7.61 (d, J=6.0 Hz, 1H), 7.81 (d, J=8.0 Hz, 1H), 7.98-8.00 (m, 1H), 8.14 (t, J=1.6, 2.0 Hz, 1H), 8.47 (d, J=6.0 Hz, 1H), 8.64 (d, J=8.0 Hz, 1H), 9.31 (s, 1H).

MS (ESI) m/e (M+1)$^+$: 280.00

Example 20. N-methyl-5-(9H-pyrrolo[2,3-b:4,5-c'] dipyridin-2-yl)pyrimidin-2-amine

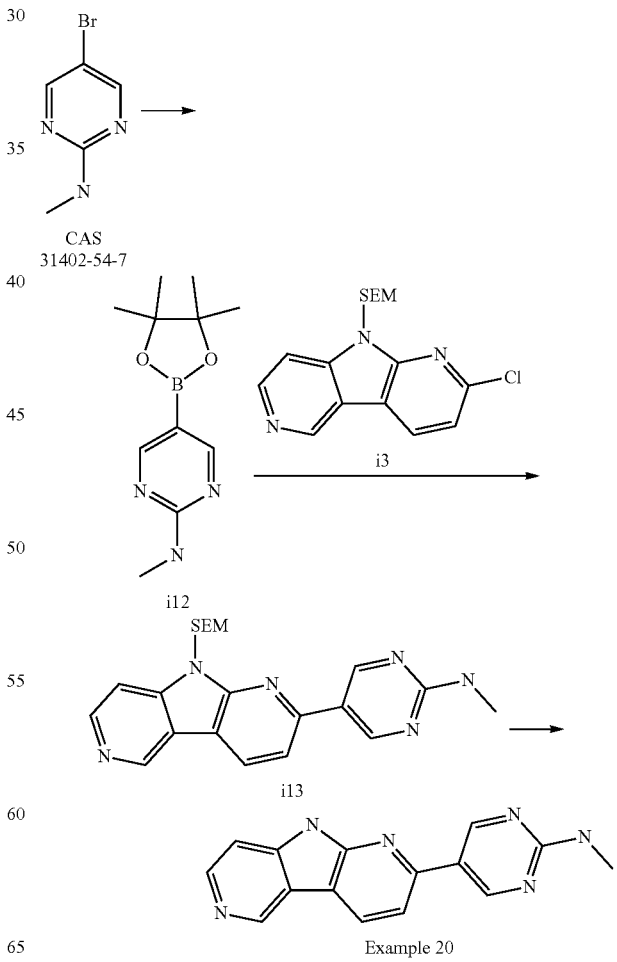

Example 20

N-methyl-5-(4,4,5,5-tetramethyl-1,3,2-dioxaborolan-2-yl)pyrimidin-2-amine (i12)

To a stirred solution of 5-bromo-N-methylpyrimidin-2-amine (0.5 g, 2.65 mmol) in dioxane (10 mL), bispinacolatodiboron (0.81 g, 3.19 mmol) and KOAc (0.39 g, 3.97 mmol) were added and the reaction was degassed with argon for 20 min. PdCl$_2$(dppf) (0.19 g, 0.26 mmol) was then added and the reaction mixture was purged with argon for another 10 min. The reaction was heated at 115° C. for 5 h. The progress of the reaction was monitored by TLC. After completion, the reaction mixture was diluted with ethyl acetate, filtered and filtrate was concentrated under reduced pressure to afford N-methyl-5-(4,4,5,5-tetramethyl-1,3,2-dioxaborolan-2-yl)pyrimidin-2-amine (i12) (0.5 g, 82%).

MS (ESI) m/e (M+1)$^+$: 236

N-methyl-5-(9-((2-(trimethylsilyl)ethoxy)methyl)-9H-pyrrolo[2,3-b:4,5-c']dipyridin-2-yl)pyrimidin-2-amine (i13)

2-chloro-9-((2-(trimethylsilyl)ethoxy)methyl)-9H-pyrrolo[2,3-b:4,5-c']dipyridine (i3) (0.3 g, 0.89 mmol) was reacted with N-methyl-5-(4,4,5,5-tetramethyl-1,3,2-dioxaborolan-2-yl)pyrimidin-2-amine (i12) (0.274 g, 1.16 mmol) according to procedure D to afford N-methyl-5-(9-((2-(trimethylsilyl)ethoxy)methyl)-9H-pyrrolo[2,3-b:4,5-c']dipyridin-2-yl)pyrimidin-2-amine (i13) (0.204 g, Yield 55%).

MS (ESI) m/e (M+1)$^+$: 407.0

N-methyl-5-(9H-pyrrolo[2,3-b:4,5-c']dipyridin-2-yl)pyrimidin-2-amine (Example 20)

SEM deprotection of N-methyl-5-(9-((2-(trimethylsilyl)ethoxy)methyl)-9H-pyrrolo[2,3-b:4,5-c']dipyridin-2-yl)pyrimidin-2-amine (i13) (0.2 g, 0.492 mmol) was performed according to procedure F to afford N-methyl-5-(9H-pyrrolo[2,3-b:4,5-c']dipyridin-2-yl)pyrimidin-2-amine. (0.06 g, Yield 44%).

$^1$H NMR (400 MHz, DMSO-d$_6$) δ 2.89 (d, J=4.77 Hz, 3H) 7.37-7.55 (m, 2H) 7.83 (d, J=8.24 Hz, 1H) 8.46 (d, J=5.64 Hz, 1H) 8.64 (d, J=8.24 Hz, 1H) 9.08 (brs, 2H) 9.34 (s, 1H) 12.29 (s, 1H).

MS (ESI) m/e (M+1)$^+$: 277.00.

Example 21. 4-(5-(9H-pyrrolo[2,3-b:4,5-c']dipyridin-2-yl)pyridin-2-yl)morpholine

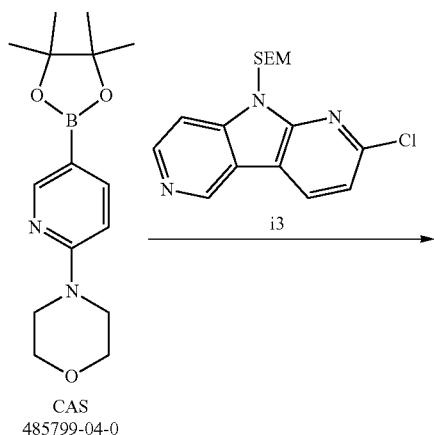

CAS 485799-04-0

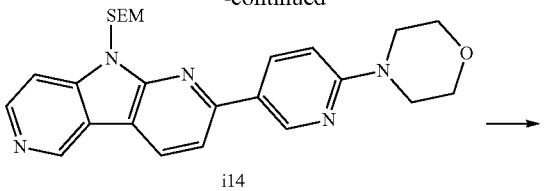

i14

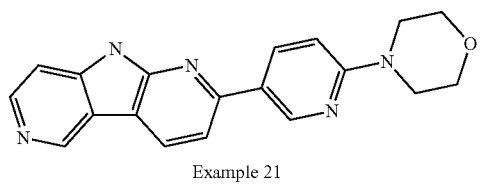

Example 21

4-(5-(9-((2-(trimethylsilyl)ethoxy)methyl)-9H-pyrrolo[2,3-b:4,5-c']dipyridin-2-yl)pyridin-2-yl)morpholine (i14)

To a stirred solution of 2-chloro-9-((2-(trimethylsilyl)ethoxy)methyl)-9H-pyrrolo[2,3-b:4,5-c]dipyridine (i3) (0.2 g, 0.6 mmol) in n-butanol (6 mL), 4-(5-(4,4,5,5-tetramethyl-1,3,2-dioxaborolan-2-yl)pyridin-2-yl)morpholine (0.226 g, 0.78 mmol) and KF (0.139 g, 2.4 mmol) were added and the reaction was purged with argon for 20 min. Pd$_2$(dba$_3$)$_2$ (0.055 g, 0.06 mmol) and xantphos (0.057 g, 0.12 mmol) were added and the reaction was heated at 100° C. for 6 h. The progress of the reaction was monitored by TLC. After completion of the reaction, the solvent was evaporated under reduced pressure to obtain crude product which was purified by silica gel (230:400 mesh) column chromatography using 2% methanol in dichloromethane as eluent to afford 4-(5-(9-((2-(trimethylsilyl)ethoxy)methyl)-9H-pyrrolo[2,3-b:4,5-c']dipyridin-2-yl)pyridin-2-yl)morpholine (i14) (0.16 g, 57%).

$^1$H NMR (400 MHz, DMSO-d$_6$) δ −0.19 (s, 9H), 0.88 (t, J=8.0 Hz, 2H), 3.52-3.62 (m, 6H), 3.72-3.77 (m, 4H), 5.96 (s, 2H), 6.98 (d, J=8.8 Hz, 1H), 7.72 (d, J=5.7 Hz, 1H), 7.95 (d, J=8.0 Hz, 1H), 8.42 (dd, J=9.0, 1.9 Hz, 1H), 8.56 (d, J=5.6 Hz, 1H), 8.67 (d, J=8.4 Hz, 1H), 9.07 (s, 1H), 9.39 (s, 1H).

MS (ESI) m/e (M+1)$^+$: 462.00

4-(5-(9H-pyrrolo[2,3-b:4,5-c']dipyridin-2-yl)pyridin-2-yl)morpholine (Example 21)

SEM deprotection of 4-(5-(9-((2-(trimethylsilyl)ethoxy)methyl)-9H-pyrrolo[2,3-b:4,5-c']dipyridin-2-yl)pyridin-2-yl)morpholine (i14) (0.16 g, 0.334 mmol) was performed according to procedure F to afford 4-(5-(9H-pyrrolo[2,3-b:4,5-c']dipyridin-2-yl)pyridin-2-yl)morpholine (0.04 g, Yield 35%).

$^1$H NMR (400 MHz, DMSO-d$_6$) δ 3.57 (brs, 4H) 3.73 (brs, 4H) 6.98 (d, J=8.38 Hz, 1H) 7.45 (d, J=5.73 Hz, 1H) 7.85 (d, J=8.38 Hz, 1H) 8.35 (d, J=8.82 Hz, 1H) 8.46 (d, J=4.85 Hz, 1H), 8.60-8.64 (m, 1H), 8.97 (brs, 1H) 9.33 (s, 1H) 12.24 (brs, 1H).

MS (ESI) m/e (M+1)$^+$: 332

Example 22. N-(2-methoxyethyl)-5-(9H-pyrrolo[2,3-b:4,5-c']dipyridin-2-yl)pyrimidin-2-amine

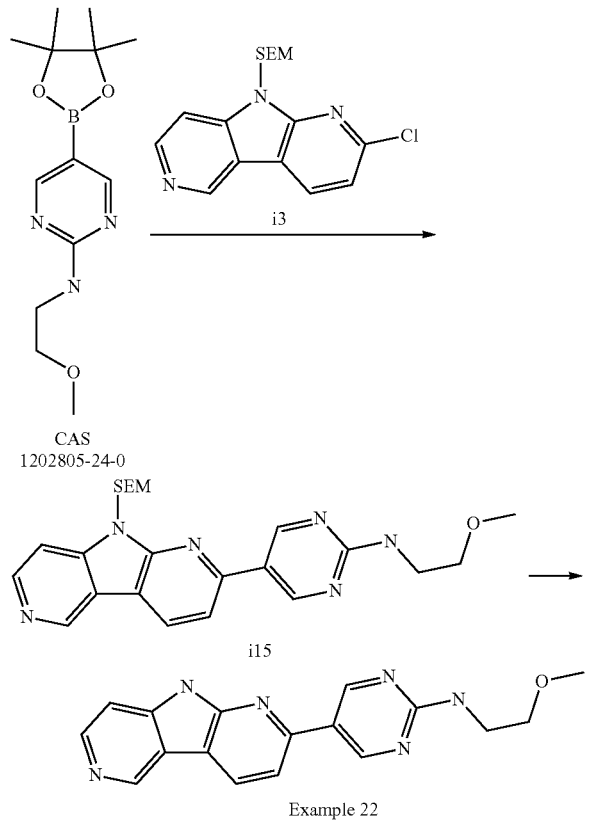

N-(2-methoxyethyl)-5-(9-((2-(trimethylsilyl)ethoxy)methyl)-9H-pyrrolo[2,3-b:4,5-c']dipyridin-2-yl)pyrimidin-2-amine (i15)

2-chloro-9-((2-(trimethylsilyl)ethoxy)methyl)-9H-pyrrolo[2,3-b:4,5-c']dipyridine (i3) (0.2 g, 0.6 mmol) was reacted with N-(2-methoxyethyl)-5-(4,4,5,5-tetramethyl-1,3,2-dioxaborolan-2-yl)pyrimidin-2-amine (0.218 g, 0.78 mmol) according to procedure G to afford N-(2-methoxyethyl)-5-(9-((2-(trimethylsilyl)ethoxy)methyl)-9H-pyrrolo[2,3-b:4,5-c']dipyridin-2-yl)pyrimidin-2-amine (i15) (0.1 g, Yield 37%).

$^1$H NMR (400 MHz, DMSO-d$_6$) δ −0.19 (s, 9H), 0.80-0.93 (m, 2H), 3.34 (s, 3H), 3.44-3.64 (m, 6H), 5.96 (s, 2H), 7.59 (d, J=6.1 Hz, 1H), 7.73 (d, J=5.7 Hz, 1H), 7.93 (d, J=8.2 Hz, 1H), 8.51-8.60 (m, 1H), 8.69 (d, J=8.1 Hz, 1H), 9.17 (s, 2H), 9.39 (s, 1H).

N-(2-methoxyethyl)-5-(9H-pyrrolo[2,3-b:4,5-c']dipyridin-2-yl)pyrimidin-2-amine (Example 22)

SEM deprotection of N-(2-methoxyethyl)-5-(9-((2-(trimethylsilyl)ethoxy)methyl)-9H-pyrrolo[2,3-b:4,5-c']dipyridin-2-yl)pyrimidin-2-amine (i15) (0.1 g, 0.22 mmol) was performed according to procedure F to afford N-(2-methoxyethyl)-5-(9H-pyrrolo[2,3-b:4,5-c']dipyridin-2-yl)pyrimidin-2-amine. (0.04 g, Yield 57%).

$^1$H NMR (400 MHz, DMSO-d$_6$) δ ppm 3.28 (s, 3H) 3.51 (brs, 4H) 7.45 (d, J=5.26 Hz, 1H) 7.52 (brs, 1H) 7.83 (d, J=7.89 Hz, 1H) 8.46 (d, J=5.26 Hz, 1H) 8.64 (d, J=7.89 Hz, 1H) 9.07 (brs, 2H) 9.34 (brs, 1H) 12.26 (brs, 1H).

MS (ESI) m/e (M+1)$^+$: 321.20

Example 23. 2-(2-(piperazin-1-yl)pyrimidin-5-yl)-9H-pyrrolo[2,3-b:4,5-c']dipyridine

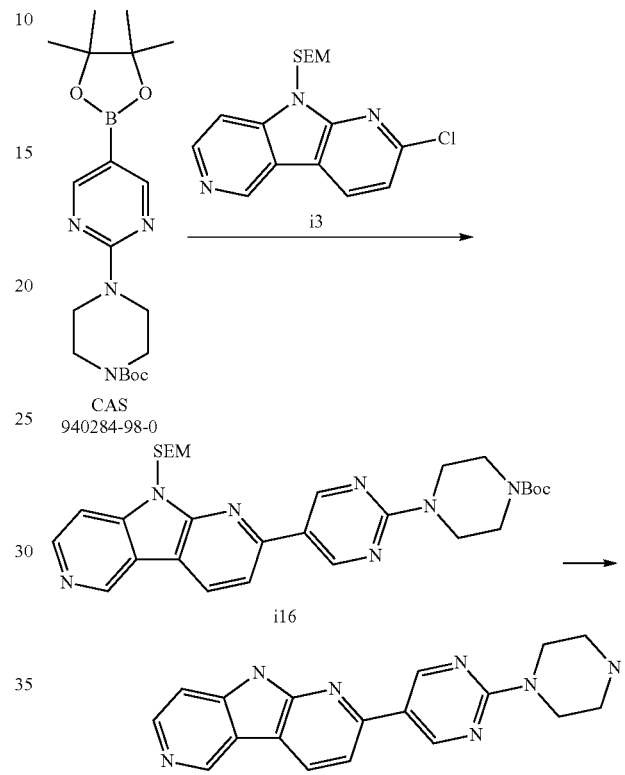

tert-butyl 4-(5-(9-((2-(trimethylsilyl)ethoxy)methyl)-9H-pyrrolo[2,3-b:4,5-c']dipyridin-2-yl)pyrimidin-2-yl)piperazine-1-carboxylate (i16)

2-chloro-9-((2-(trimethylsilyl)ethoxy)methyl)-9H-pyrrolo[2,3-b:4,5-c']dipyridine (i3) (0.2 g, 0.6 mmol) was reacted with tert-butyl 4-(5-(4,4,5,5-tetramethyl-1,3,2-dioxaborolan-2-yl)pyrimidin-2-yl)piperazine-1-carboxylate (0.24 g, 0.78 mmol) according to procedure G to afford tert-butyl 4-(5-(9-((2-(trimethylsilyl)ethoxy)methyl)-9H-pyrrolo[2,3-b:4,5-c']dipyridin-2-yl)pyrimidin-2-yl)piperazine-1-carboxylate (i16) (0.16 g, Yield 47%).

$^1$H NMR (400 MHz, DMSO-d$_6$) δ −0.18 (s, 9H), 0.84 (t, J=8.0 Hz, 2H), 1.07 (s, 9H), 3.46 (d, J=5.5 Hz, 4H), 3.63 (t, J=8.0 Hz, 2H), 3.85 (d, J=5.5 Hz, 4H), 6.02 (s, 2H), 7.95 (d, J=6.0 Hz, 1H), 8.05 (d, J=8.3 Hz, 1H), 8.68 (d, J=6.1 Hz, 1H), 8.78 (d, J=8.0 Hz, 1H), 9.28 (s, 2H), 9.55 (s, 1H),

MS (ESI) m/e (M+1)$^+$: 562.50

2-(2-(piperazin-1-yl)pyrimidin-5-yl)-9H-pyrrolo[2,3-b:4,5-c']dipyridine (Example 23)

SEM deprotection of tert-butyl 4-(5-(9-((2-(trimethylsilyl)ethoxy)methyl)-9H-pyrrolo[2,3-b:4,5-c]dipyridin-2-yl)pyrimidin-2-yl)piperazine-1-carboxylate (i16) (0.16 g, 0.284 mmol) was performed according to procedure F to afford 2-(2-(piperazin-1-yl)pyrimidin-5-yl)-9H-pyrrolo[2,3-b:4,5-c]dipyridine (0.06 g, Yield 63%).

¹H NMR (400 MHz, DMSO-d₆) δ 1.18-1.37 (m, 1H) 2.85 (brs, 4H) 3.82 (brs, 4H) 7.45 (d, J=5.73 Hz, 1H) 7.86 (d, J=7.94 Hz, 1H) 8.47 (d, J=5.73 Hz, 1H) 8.66 (d, J=7.94 Hz, 1H) 9.14 (s, 2H) 9.35 (s, 1H) 12.31 (brs, 1H).

MS (ESI) m/e (M+1)⁺: 332.10

Example 24. 2-(5-methyl-1H-pyrazol-3-yl)-9H-pyrrolo[2,3-b:4,5-c']dipyridine

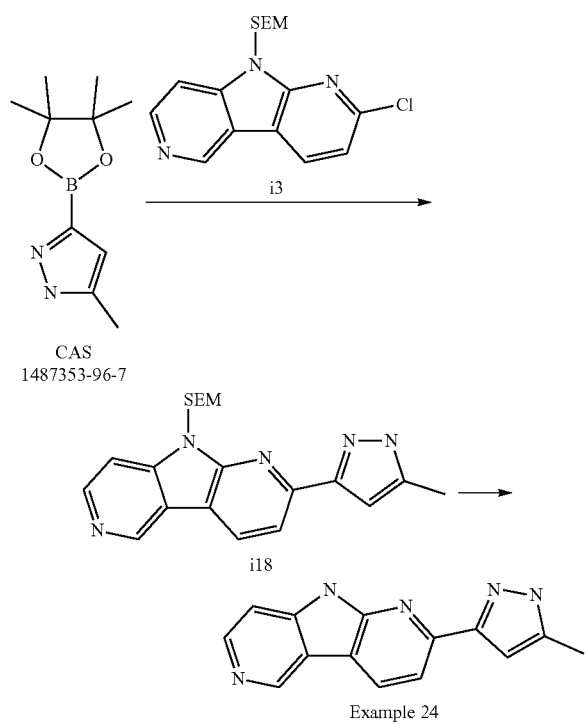

2-(5-methyl-1H-pyrazol-3-yl)-9-((2-(trimethylsilyl)ethoxy)methyl)-9H-pyrrolo[2,3-b:4,5-c]dipyridine (i18)

2-chloro-9-((2-(trimethylsilyl)ethoxy)methyl)-9H-pyrrolo[2,3-b:4,5-c']dipyridine (i3) (0.2 g, 0.6 mmol) was reacted with 5-methyl-3-(4,4,5,5-tetramethyl-1,3,2-dioxaborolan-2-yl)-1H-pyrazole (0.162 g, 0.78 mmol) according to procedure G to afford 2-(5-methyl-1H-pyrazol-3-yl)-9-((2-(trimethylsilyl)ethoxy)methyl)-9H-pyrrolo[2,3-b:4,5-c']dipyridine (i18) (0.1 g, Yield 44%).

¹H NMR (400 MHz, DMSO-d₆) δ −0.18 (s, 9H), 0.81-0.96 (m, 2H), 2.32 (s, 3H), 3.59 (t, J=8.0 Hz, 2H), 5.94 (s, 2H), 6.76 (d, J=7.2 Hz, 1H), 7.72 (d, J=5.7 Hz, 1H), 7.98 (d, J=8.1 Hz, 1H), 8.56 (d, J=5.6 Hz, 1H), 8.64 (d, J=8.2 Hz, 1H), 9.38 (s, 1H), 12.77 (s, 1H), MS (ESI) m/e (M+1)⁺: 380.05

2-(5-methyl-1H-pyrazol-3-yl)-9H-pyrrolo[2,3-b:4,5-c']dipyridine (Example 24)

SEM deprotection of 2-(5-methyl-1H-pyrazol-3-yl)-9-((2-(trimethylsilyl)ethoxy)methyl)-9H-pyrrolo[2,3-b:4,5-c'] dipyridine (i18) (0.1 g, 0.26 mmol) was performed according to procedure F to afford 2-(5-methyl-1H-pyrazol-3-yl)-9H-pyrrolo[2,3-b:4,5-c']dipyridine (0.04 g, Yield 63%).

¹H NMR (400 MHz, DMSO-d₆) δ 2.29 (brs, 3H) 6.65 (s, 1H) 7.50 (d, J=5.6 Hz, 1H), 7.90 (brs, 1H) 8.44 (d, J=5.26 Hz, 1H) 8.60 (d, J=7.02 Hz, 1H) 9.29 (s, 1H), 12.80 (brs, 1H), 13.00 (brs).

MS (ESI) m/e (M+1)⁺: 250.10

Example 25. 1-(2-fluoroethyl)-1H-pyrazol-4-yl)-9H-pyrrolo[2,3-b:4,5-c']dipyridine

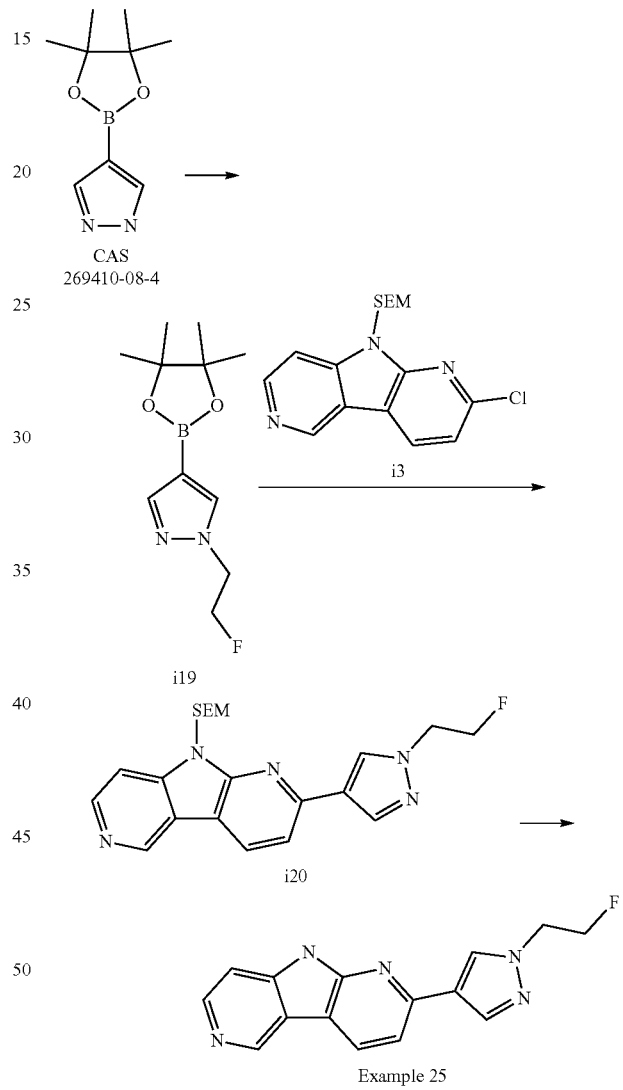

1-(2-fluoroethyl)-4-(4,4,5,5-tetramethyl-1,3,2-dioxaborolan-2-yl)-1H-pyrazole (i19)

To a stirred solution of 4-(4,4,5,5-tetramethyl-1,3,2-dioxaborolan-2-yl)-1H-pyrazole (0.2 g, 1.03 mmol) in DMF (6 mL), NaH (0.037 g, 1.54 mmol) was added at 0° C. and the reaction mixture was stirred at room temperature for 30 min. 1-fluoro-2-iodoethane (0.197 g, 1.13 mmol) was then added and the reaction mixture was allowed to warm at room temperature and stirred for 4 h. The progress of the reaction was monitored by TLC. After completion, the mixture was diluted with water and extracted with diethyl ether. The organic layer was separated, dried over anhydrous sodium sulphate and concentrated under reduced pressure to afford 1-(2-fluoroethyl)-4-(4,4,5,5-tetramethyl-1,3,2-dioxaborolan-2-yl)-1H-pyrazole (i19) (0.21 g, 85%), which was used as such for next reaction without any purification.

MS (ESI) m/e (M+1)$^+$: 241.00

2-(1-(2-fluoroethyl)-1H-pyrazol-4-yl)-9-((2-(trimethylsilyl)ethoxy)methyl)-9H-pyrrolo[2,3-b:4,5-c] dipyridine (i20)

2-chloro-9-((2-(trimethylsilyl)ethoxy)methyl)-9H-pyrrolo[2,3-b:4,5-c']dipyridine (i3) (0.2 g, 0.60 mmol) was reacted with 1-(2-fluoroethyl)-4-(4,4,5,5-tetramethyl-1,3,2-dioxaborolan-2-yl)-1H-pyrazole (i19) (0.187 g, 0.78 mmol) according to procedure C to afford 2-(1-(2-fluoroethyl)-1H-pyrazol-4-yl)-9-((2-(trimethylsilyl)ethoxy)methyl)-9H-pyrrolo[2,3-b:4,5-c']dipyridine (i20) (0.1 g, Yield 41%).

$^1$H NMR (400 MHz, DMSO-d$_6$) δ −0.18 (s, 9H), 0.81-0.92 (t, J=8.0 Hz, 2H), 3.58 (t, J=8.0 Hz, 2H), 4.52 (m, 2H), 4.77 (t, J=4.7 Hz, 1H), 4.89 (t, J=4.7 Hz, 1H), 5.93 (s, 2H), 7.65-7.75 (m, 2H), 8.22 (s, 1H), 8.49 (s, 1H), 8.55 (d, J=5.7 Hz, 1H), 8.62 (d, J=8.0 Hz, 1H), 9.36 (s, 1H), MS (ESI) m/e (M+1)$^+$: 412.00

1-(2-fluoroethyl)-1H-pyrazol-4-yl)-9H-pyrrolo[2,3-b:4,5-c']dipyridine (Example 25)

SEM deprotection of (1-(2-fluoroethyl)-1H-pyrazol-4-yl)-9-((2-(trimethylsilyl)ethoxy)methyl)-9H-pyrrolo[2,3-b:4,5-c']dipyridine (i20) (0.1 g, 0.243 mmol) was performed according to procedure F to afford 1-(2-fluoroethyl)-1H-pyrazol-4-yl)-9H-pyrrolo[2,3-b:4,5-c']dipyridine (0.04 g, Yield 58%).

$^1$H NMR (400 MHz, DMSO-d$_6$) δ 4.44-4.61 (m, 2H) 4.71-4.95 (m, 2H) 7.43 (d, J=4.34 Hz, 1H) 7.64 (d, J=7.80 Hz, 1H) 8.15 (brs, 1H) 8.38-8.48 (m, 2H) 8.58 (d, J=7.80 Hz, 1H) 9.30 (brs, 1H) 12.17 (brs, 1H).

MS (ESI) m/e (M+1)$^+$: 282.00

Example 26. 2-(4-(9H-pyrrolo[2,3-b:4,5-c']dipyridin-2-yl)-1H-pyrazol-1-yl)-N-methylacetamide

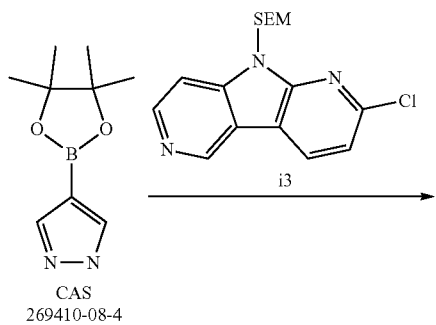

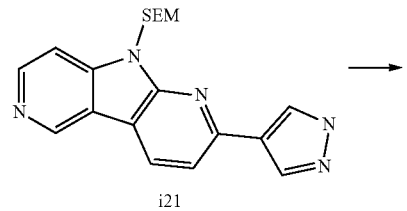

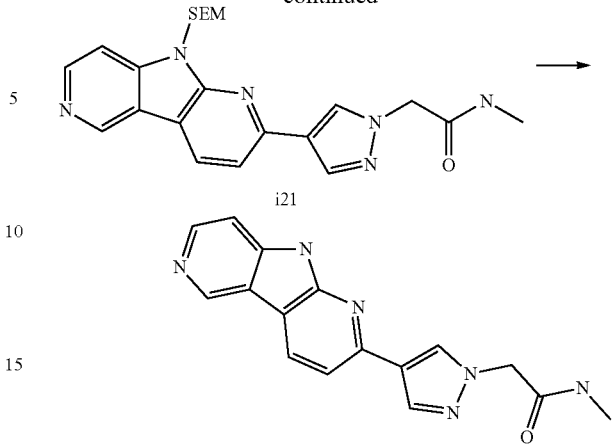

Example 26

2-(1H-pyrazol-4-yl)-9-((2-(trimethylsilyl)ethoxy) methyl)-9H-pyrrolo[2,3-b:4,5-c']dipyridine (i21)

2-chloro-9-((2-(trimethylsilyl)ethoxy)methyl)-9H-pyrrolo[2,3-b:4,5-c']dipyridine (i3) (0.2 g, 0.60 mmol) was reacted with 4-(4,4,5,5-tetramethyl-1,3,2-dioxaborolan-2-yl)-1H-pyrazole (0.153 g, 0.78 mmol) according to procedure C to afford 2-(1H-pyrazol-4-yl)-9-((2-(trimethylsilyl)ethoxy)methyl)-9H-pyrrolo[2,3-b:4,5-c']dipyridine (i21) (0.5 g, Yield 91%) which was used as such for next step without purification.

MS (ESI) m/e (M+1)$^+$: 366.00

N-methyl-2-(4-(9-((2-(trimethylsilyl)ethoxy) methyl)-9H-pyrrolo[2,3-b:4,5-c']dipyridin-2-yl)-1H-pyrazol-1-yl)acetamide (i22)

To a stirred solution of 2-(1H-pyrazol-4-yl)-9-((2-(trimethylsilyl)ethoxy)methyl)-9H-pyrrolo[2,3-b:4,5-c']dipyridine (i21) (0.5 g, 1.36 mmol) and 2-bromo-N-methylacetamide (0.249 g, 1.64 mmol) in DMF (10 mL), K$_2$CO$_3$ (0.567 g, 4.19 mmol) was added and the reaction mixture was heated at 85° C. for 16 h. The progress of the reaction was monitored by TLC. After completion, the mixture was quenched with water and extracted with ethyl acetate. The organic layer was separated, dried over anhydrous sodium sulphate and evaporated under reduced pressure. The crude product was purified by silica gel (100-200 mesh) column chromatography using 3% methanol in dichloromethane as eluent to afford N-methyl-2-(4-(9-((2-(trimethylsilyl)ethoxy)methyl)-9H-pyrrolo[2,3-b:4,5-c']dipyridin-2-yl)-1H-pyrazol-1-yl)acetamide (i22) (0.12 g, Yield 20%).

MS (ESI) m/e (M+1)$^+$: 437.00

2-(4-(9H-pyrrolo[2,3-b:4,5-c']dipyridin-2-yl)-1H-pyrazol-1-yl)-N-methylacetamide (Example 26)

SEM deprotection of N-methyl-2-(4-(9-((2-(trimethylsilyl)ethoxy)methyl)-9H-pyrrolo[2,3-b:4,5-c]dipyridin-2-yl)-1H-pyrazol-1-yl)acetamide (i22) (0.1 g, 0.229 mmol) was performed according to procedure F to afford 2-(4-(9H-pyrrolo[2,3-b:4,5-c']dipyridin-2-yl)-1H-pyrazol-1-yl)-N-methylacetamide (0.02 g, Yield 28%).

$^1$H NMR (400 MHz, DMSO-d$_6$) δ 2.64 (d, J=4.62 Hz, 3H) 4.85 (s, 2H) 7.44 (d, J=5.09 Hz, 1H) 7.64 (d, J=8.32 Hz, 1H)

8.05 (d, J=3.70 Hz, 1H) 8.11 (s, 1H) 8.36 (s, 1H) 8.44 (brs, 1H) 8.58 (d, J=7.86 Hz, 1H) 9.31 (brs, 1H) 12.21 (brs, 1H)

MS (ESI) m/e (M+1)+: 307.00

Example 27. N-methyl-6-(9H-pyrrolo[2,3-b:4,5-c'] dipyridin-2-yl)nicotinamide

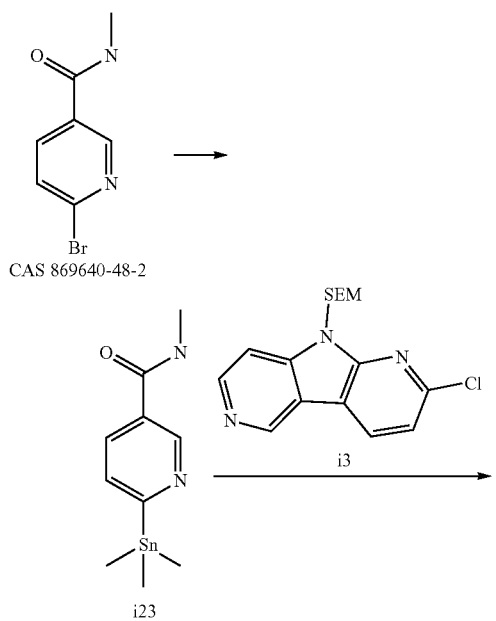

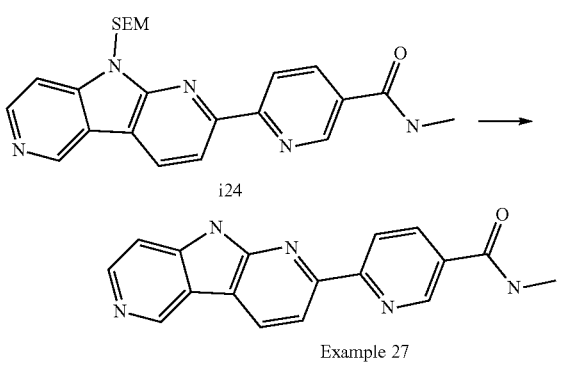

N-methyl-6-(trimethylstannyl)nicotinamide (i23)

To a stirred solution of 6-bromo-N-methylnicotinamide (0.35 g, 1.6 mmol) in DME (20 mL), hexamethylditin (0.586 g, 1.79 mmol) was added and the reaction was purged with argon for 20 min. Pd(PPh$_3$)$_4$ (0.095 g, 0.08 mmol) was added and the reaction was heated at 110° C. for 16 h. The progress of the reaction was monitored by TLC. After completion, reaction affords N-methyl-6-(trimethylstannyl)nicotinamide (i23) which was used as such for next step without work up and further purification.

LCMS (M+1): 301.00

N-methyl-6-(9-((2-(trimethylsilyl)ethoxy)methyl)-9H-pyrrolo[2,3-b:4,5-c']dipyridin-2-yl)nicotinamide (i24)

To a stirred solution of 2-chloro-9-((2-(trimethylsilyl) ethoxy)methyl)-9H-pyrrolo[2,3-b:4,5-c]dipyridine (i3) (0.3 g, 0.9 mmol) and N-methyl-6-(trimethylstannyl)nicotinamide (i23) (0.484 g, 1.62 mmol) in DME (20 mL), argon was purged for 20 min. Pd(PPh$_3$)$_4$ (0.058 g, 0.05 mmol) was added and the reaction was heated at 100° C. for 16 h. After completion of the reaction, the solvent was removed under reduced pressure to obtain a crude product, which was purified by silica gel (230-400 mesh) column chromatography using 2% methanol in dichloromethane as eluent to afford N-methyl-6-(9-((2-(trimethylsilyl)ethoxy)methyl)-9H-pyrrolo[2,3-b:4,5-c']dipyridin-2-yl)nicotinamide (i24) (0.17 g, Yield 44%).

$^1$H NMR (400 MHz, DMSO-d$_6$) δ −0.20 (s, 9H). 0.85-0.94 (m, 2H), 2.83 (d, J=4.5 Hz, 3H), 3.63 (t, J=8.1 Hz, 2H), 6.03 (s, 2H), 7.80 (d, J=5.7 Hz, 1H), 8.37 (dd, J=8.3, 2.3 Hz, 1H), 8.53 (d, J=8.1 Hz, 1H), 8.59-8.59 (m, 3H), 8.84 (d, J=8.1 Hz, 1H), 9.13 (d, J=2.1 Hz, 1H), 9.48 (s, 1H).

MS (ESI) m/e (M+1)+: 434.00

N-methyl-6-(9H-pyrrolo[2,3-b:4,5-c']dipyridin-2-yl) nicotinamide (Example 27)

SEM deprotection of N-methyl-6-(9-((2-(trimethylsilyl) ethoxy)methyl)-9H-pyrrolo[2,3-b:4,5-c']dipyridin-2-yl) nicotinamide (i24) (0.2 g, 0.46 mmol) was performed according to procedure F to afford N-methyl-6-(9H-pyrrolo [2,3-b:4,5-c']dipyridin-2-yl)nicotinamide (0.075 g, Yield 63%).

$^1$H NMR (400 MHz, Methanol-d$_4$) δ 3.01 (s, 3H), 7.55-7.61 (m, 1H), 8.33 (dd, J=8.3, 2.7 Hz, 1H), 8.43-8.51 (m, 2H), 8.63 (d, J=8.4 Hz, 1H), 8.72 (dd, J=8.2, 1.9 Hz, 1H), 9.09 (d, J=2.7 Hz, 1H), 9.32 (s, 1H).

MS (ESI) m/e (M+1)+: 304.15

Example 28. N,N-dimethyl-5-(9H-pyrrolo[2,3-b:4,5-c']dipyridin-2-yl)picolinamide

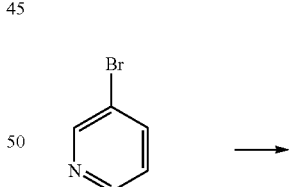

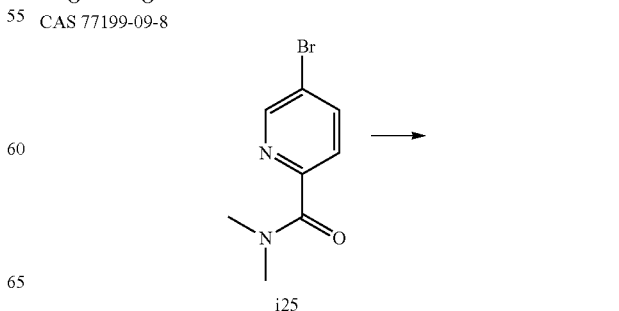

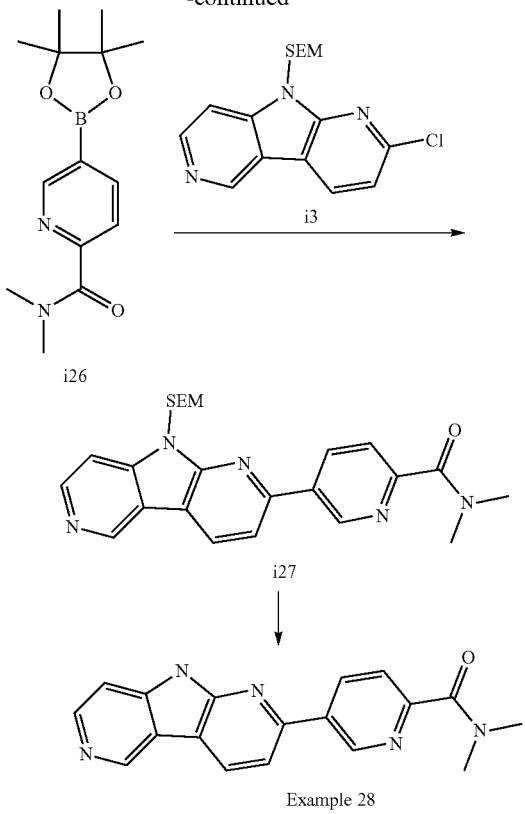

5-bromo-N,N-dimethylpicolinamide (i25)

To a stirred solution of 5-bromopicolinic acid (1 g, 4.95 mmol) in DCM (6 mL), DMF (0.1 mL), and oxalyl chloride (0.817 g, 6.43 mmol) were added and stirred at room temperature for 16 h. After completion of the reaction, the solvent was removed under reduced pressure to obtain a residue to which DCM and trimethyl amine was added. The reaction mixture was cooled to 0° C., dimethylamine (1.11 g, 24.75 mmol) was added and the reaction mixture was stirred at room temperature for 3 h. The progress of the reaction was monitored by TLC. After completion, the mixture was quenched with water and extracted with ethyl acetate. The organic layer was separated, dried over anhydrous sodium sulphate and concentrated under reduced pressure to afford 5-bromo-N,N-dimethylpicolinamide (i25) (1.2 g crude).

$^1$H NMR (400 MHz, DMSO-$d_6$) δ 2.86 (s, 3H), 3.03 (s, 3H), 7.54 (d, J=8.4 Hz, 1H), 8.17 (d, J=8.4 Hz, 1H), 8.78 (s, 1H),

N,N-dimethyl-5-(4,4,5,5-tetramethyl-1,3,2-dioxaborolan-2-yl)picolinamide (i26)

5-bromo-N,N-dimethylpicolinamide (i25) (0.6 g, 2.62 mmol) was reacted with Bis(pinacolato)diboron (0.731 g, 2.88 mmol) according to procedure H to afford N,N-dimethyl-5-(4,4,5,5-tetramethyl-1,3,2-dioxaborolan-2-yl)picolinamide (i26) (0.8 g, quantitative).

MS (ESI) m/e (M+1)$^+$: 277.05

N,N-dimethyl-5-(9-((2-(trimethylsilyl)ethoxy)methyl)-9H-pyrrolo[2,3-b:4,5-c']dipyridin-2-yl)picolinamide (i27)

2-chloro-9-((2-(trimethylsilyl)ethoxy)methyl)-9H-pyrrolo[2,3-b:4,5-c']dipyridine (i3) (0.23 g, 0.69 mmol) was reacted with N,N-dimethyl-5-(4,4,5,5-tetramethyl-1,3,2-dioxaborolan-2-yl)picolinamide (i26) (0.386 g, 1.38 mmol) according to procedure C to afford N,N-dimethyl-5-(9-((2-(trimethylsilyl)ethoxy)methyl)-9H-pyrrolo[2,3-b:4,5-c']dipyridin-2-yl)picolinamide (i27) (0.12 g, Yield 39%).

$^1$H NMR (400 MHz, DMSO-$d_6$) δ −0.21 (s, 9H). 0.81-0.94 (m, 2H), 3.03 (s, 3H), 3.06 (s, 3H), 3.57-3.67 (m, 2H), 6.01 (s, 2H), 7.69-7.82 (m, 2H), 8.19 (dd, J=8.1, 1.7 Hz, 1H), 8.58-8.65 (m, 1H), 8.74 (m, 1H), 8.83 (dd, J=8.2, 1.7 Hz, 1H), 9.44-9.51 (m, 2H),

MS (ESI) m/e (M+1)$^+$: 448.00

N,N-dimethyl-5-(9H-pyrrolo[2,3-b:4,5-c']dipyridin-2-yl)picolinamide (Example 28)

SEM deprotection of N,N-dimethyl-5-(9-((2-(trimethylsilyl)ethoxy)methyl)-9H-pyrrolo[2,3-b:4,5-c]dipyridin-2-yl)picolinamide (i27) (0.12 g, 0.27 mmol) was performed according to procedure F to afford N,N-dimethyl-5-(9H-pyrrolo[2,3-b:4,5-c']dipyridin-2-yl)picolinamide (0.03 g, Yield 36%).

$^1$H NMR (400 MHz, Methanol-$d_4$) δ 3.10 (s, 3H) 3.18 (s, 3H) 7.58 (d, J=5.70 Hz, 1H) 7.74 (d, J=7.89 Hz, 1H) 7.96-8.04 (m, 1H) 8.48 (d, J=5.70 Hz, 1H) 8.71 (d, J=7.89 Hz, 2H) 9.32 (s, 1H) 9.40 (d, J=1.75 Hz, 1H).

MS (ESI) m/e (M+1)$^+$: 318.15

Example 29. N-(2-fluoroethyl)-5-(9H-pyrrolo[2,3-b:4,5-c']dipyridin-2-yl)picolinamide

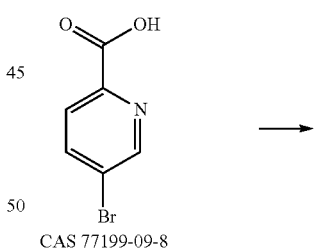

CAS 77199-09-8

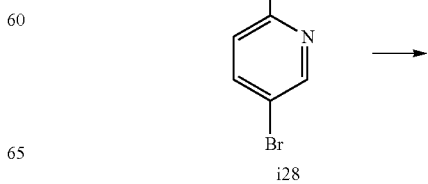

i28

-continued

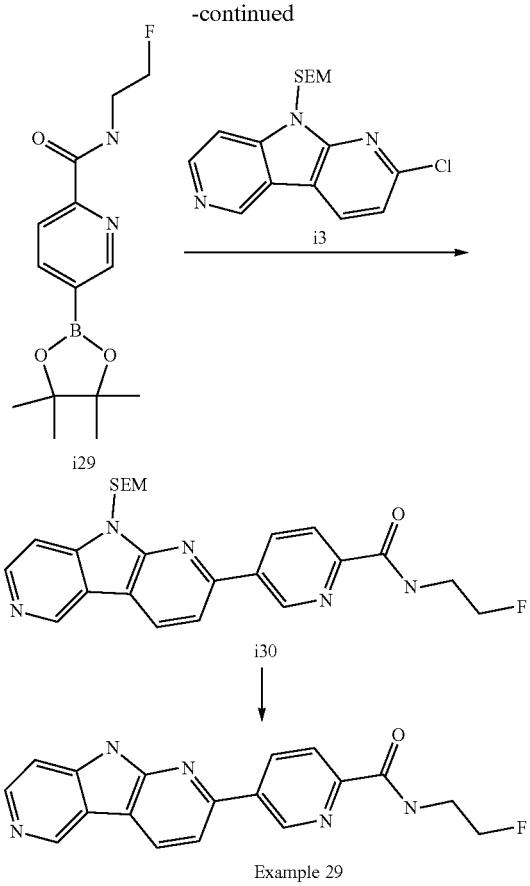

5-bromo-N-(2-fluoroethyl)picolinamide (i28)

To a stirred solution of 5-bromopicolinic acid (1 g, 4.9 mmol) in DCM (6 mL), DMF (0.1 mL) and oxalyl chloride (0.81 g, 7.3 mmol) were added at 0° C. and stirred at room temperature for 1 h. The reaction mixture was evaporated under reduced pressure. The residue was dissolved in DCM (6 mL) and TEA (1.48 g, 14.7 mmol) was added followed by a dropwise addition of 2-fluoroethanamine (0.37 g, 5.9 mmol) at 0° C. The reaction was then stirred at room temperature for 1 h. The progress of the reaction was monitored by TLC. After completion, the mixture was quenched with saturated sodium bicarbonate solution and extracted with ethyl acetate. The organic layer was separated, dried over anhydrous sodium sulphate and concentrated under reduced pressure. The crude product was purified by silica gel (100-200 mesh) column chromatography using 3% methanol in dichloromethane as eluent to afford 5-bromo-N-(2-fluoroethyl)picolinamide (i28) (1.1 g, Yield 87%).

MS (ESI) m/e (M+1)$^+$: 248.85

N-(2-fluoroethyl)-5-(4,4,5,5-tetramethyl-1,3,2-dioxaborolan-2-yl)picolinamide (i29)

5-bromo-N-(2-fluoroethyl)picolinamide (i28) was reacted with Bis(pinacolato)diboron (0.339 g, 1.33 mmol) according to procedure H to afford N-(2-fluoroethyl)-5-(4,4,5,5-tetramethyl-1,3,2-dioxaborolan-2-yl)picolinamide (i29) (0.6 g) which was used as such for next reaction.

N-(2-fluoroethyl)-5-(9-((2-(trimethylsilyl)ethoxy)methyl)-9H-pyrrolo[2,3-b:4,5-c']dipyridin-2-yl)picolinamide (i30)

2-chloro-9-((2-(trimethylsilyl)ethoxy)methyl)-9H-pyrrolo[2,3-b:4,5-c']dipyridine (i3) (0.2 g, 0.60 mmol) was reacted with N-(2-fluoroethyl)-5-(4,4,5,5-tetramethyl-1,3,2-dioxaborolan-2-yl)picolinamide (i29) (0.229 g, 0.78 mmol) according to procedure C to afford N-(2-fluoroethyl)-5-(94 (2-(trimethylsilyl)ethoxy)methyl)-9H-pyrrolo[2,3-b:4,5-c'] dipyridin-2-yl)picolinamide (i30) (0.07 g, Yield 25%).

MS (ESI) m/e (M+1)$^+$: 466

N-(2-fluoroethyl)-5-(9H-pyrrolo[2,3-b:4,5-c']dipyridin-2-yl)picolinamide (Example 29)

SEM deprotection of N-(2-fluoroethyl)-5-(9-((2-(trimethylsilyl)ethoxy)methyl)-9H-pyrrolo[2,3-b:4,5-c']dipyridin-2-yl)picolinamide (i30) (0.09 g, 0.193 mmol) was performed according to procedure F to afford N-(2-fluoroethyl)-5-(9H-pyrrolo[2,3-b:4,5-c']dipyridin-2-yl)picolinamide (0.027 g, Yield 42%).

$^1$H NMR (400 MHz, DMSO-$d_6$) δ 3.61 (t, J=5.06 Hz, 1H) 3.67 (t, J=5.06 Hz, 1H) 4.51 (t, J=5.06 Hz, 1H) 4.63 (t, J=5.25 Hz, 1H) 7.56 (d, J=5.06 Hz, 1H) 8.05 (d, J=7.78 Hz, 1H) 8.17 (d, J=8.56 Hz, 1H) 8.48 (d, J=5.45 Hz, 1H) 8.69 (dd, J=7.98, 2.14 Hz, 1H) 8.77 (d, J=7.79 Hz, 1H), 9.00 (m, 1H), 9.41 (s, 2H), 12.45 (brs, 1H).

MS (ESI) m/e (M+1)$^+$: 336

Example 30. N-(2-methoxyethyl)-5-(9H-pyrrolo[2,3-b:4,5-c']dipyridin-2-yl)picolinamide

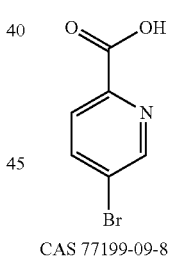
CAS 77199-09-8

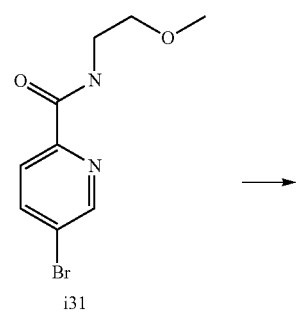
i31

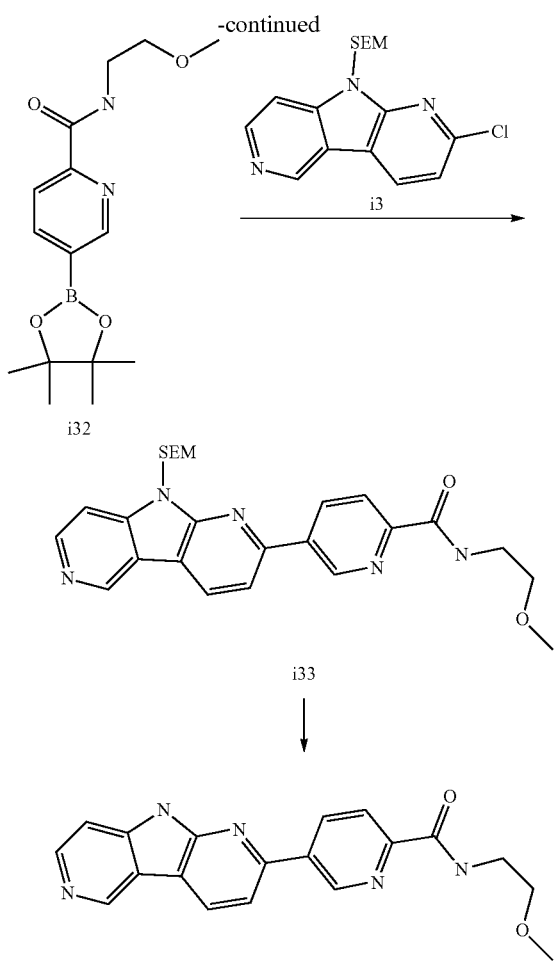

5-bromo-N-(2-methoxyethyl)picolinamide (i31)

To a stirred solution of 5-bromopicolinic acid (1 g, 4.95 mmol) in DCM (5 mL), 2-methoxyethanamine (0.446 g, 5.9 mmol), and pyridine (1.95 g, 24.75 mmol) were added and the reaction mixture was stirred at 0° C. for 10 min. POCl$_3$ (3.79 g, 24.75 mmol) was then added at the same temperature. The reaction was stirred at room temperature for 1 h. The progress of the reaction was monitored by TLC. After completion, the mixture was quenched with saturated sodium bi-carbonate solution and extracted with ethyl acetate. The organic layer was separated, dried over anhydrous sodium sulphate and concentrated under reduced pressure to afford 5-bromo-N-(2-methoxyethyl)picolinamide (i31) (1.2 g, Yield 93%).

$^1$H NMR (400 MHz, DMSO-d$_6$) δ 3.29 (s, 3H), 3.40-3.51 (m, 4H), 7.97 (d, J=8.5 Hz, 1H), 8.25 (dd, J=8.4, 2.3 Hz, 1H), 8.70 (s, 1H), 8.85 (s, 1H),

MS (ESI) m/e (M+2)+: 261.00

N-(2-methoxyethyl)-5-(4,4,5,5-tetramethyl-1,3,2-dioxaborolan-2-yl)picolinamide (i32)

5-bromo-N-(2-methoxyethyl)picolinamide (i31) (0.4 g, 1.54 mmol) was reacted with Bis(pinacolato)diboron (0.431 g, 1.69 mmol) according to procedure H to afford N-(2-methoxyethyl)-5-(4,4,5,5-tetramethyl-1,3,2-dioxaborolan-2-yl)picolinamide (i32) (0.5 g, quantitative), which was used as such for next reaction.

MS (ESI) m/e (M+1)$^+$: 306.95

N-(2-methoxyethyl)-5-(9-((2-(trimethylsilyl)ethoxy)methyl)-9H-pyrrolo[2,3-b:4,5-c']dipyridin-2-yl)picolinamide (i33)

N-(2-methoxyethyl)-5-(4,4,5,5-tetramethyl-1,3,2-dioxaborolan-2-yl)picolinamide (i32) (0.422 g, 1.337 mmol) was reacted with 2-chloro-9-((2-(trimethylsilyl)ethoxy)methyl)-9H-pyrrolo[2,3-b:4,5-c]dipyridine (i3) (0.23 g, 0.69 mmol) according to procedure C to afford N-(2-methoxyethyl)-5-(9-((2-(trimethylsilyl)ethoxy)methyl)-9H-pyrrolo[2,3-b:4,5-c']dipyridin-2-yl)picolinamide (i33) (0.24 g, Yield 73%).

$^1$H NMR (400 MHz, DMSO-d$_6$) δ −0.21 (s, 9H), 0.87 (t, J=7.8 Hz, 2H), 3.22-3.34 (m, 4H), 3.48-3.55 (m, 4H), 3.63 (t, J=7.8 Hz, 2H), 6.01 (s, 2H), 7.79 (d, J=5.7 Hz, 1H), 8.17-8.23 (m, 2H), 8.62 (d, J=5.7 Hz, 1H), 8.88-8.79 (m, 1H), 8.82-8.85 (m, 1H), 8.76 (s, 1H), 9.47 (s, 1H).

MS (ESI) m/e (M+1)$^+$: 478.00

N-(2-methoxyethyl)-5-(9H-pyrrolo[2,3-b:4,5-c']dipyridin-2-yl)picolinamide (Example 30)

SEM deprotection of N-(2-methoxyethyl)-5-(9-((2-(trimethylsilyl)ethoxy)methyl)-9H-pyrrolo[2,3-b:4,5-c']dipyridin-2-yl)picolinamide (i33) (0.24 g, 0.50 mmol) was performed according to procedure F to afford N-(2-methoxyethyl)-5-(9H-pyrrolo[2,3-b:4,5-c']dipyridin-2-yl)picolinamide (0.12 g, Yield 69%)

$^1$H NMR (400 MHz, DMSO-d$_6$) δ 3.29 (s, 3H) 3.44-3.60 (m, 4H) 7.52 (d, J=5.77 Hz, 1H) 8.12 (d, J=7.99 Hz, 1H) 8.19 (d, J=8.43 Hz, 1H) 8.52 (d, J=5.32 Hz, 1H) 8.69-8.85 (m, 3H) 9.43 (d, J=3.99 Hz, 2H) 12.50 (brs, 1H)

MS (ESI) m/e (M+1)$^+$: 348.00

Example 31. 2-(4-methoxy-1H-pyrazol-1-yl)-9H-pyrrolo[2,3-b:4,5-c']dipyridine

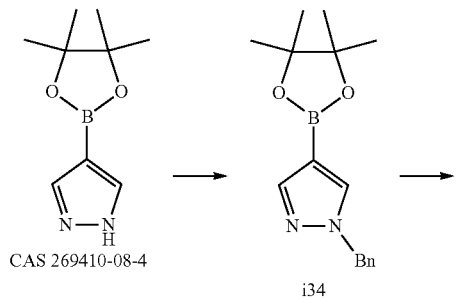

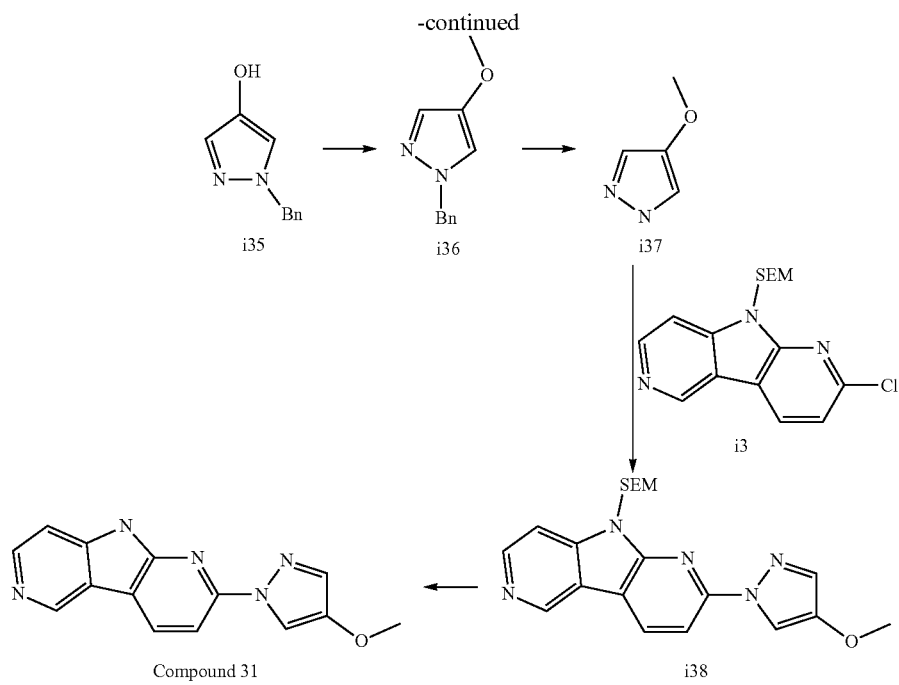

1-benzyl-4-(4,4,5,5-tetramethyl-1,3,2-dioxaborolan-2-yl)-1H-pyrazole (i34)

To a stirred solution of 4-(4,4,5,5-tetramethyl-1,3,2-dioxaborolan-2-yl)-1H-pyrazole (3.0 g, 15.46 mmol) in THF (50 mL), NaH (0.408 g, 17.01 mmol) was added at 0° C. and the reaction was stirred for 30 min. Benzyl bromide (2.9 g, 17.01 mmol) was then added at the same temperature and the reaction was stirred at room temperature for 16 h. The progress of the reaction was monitored by TLC. After completion, the mixture was diluted with water and the pH adjusted to 7 using 2 M HCl. The aqueous layer was extracted with ethyl acetate. The organic layer was separated, dried over anhydrous sodium sulphate and concentrated under reduced pressure. The crude product was purified by silica gel (100-200 mesh) column chromatography using 8% ethyl acetate in n-hexanes as eluent to afford 1-benzyl-4-(4,4,5,5-tetramethyl-1,3,2-dioxaborolan-2-yl)-1H-pyrazole (i34) (2.6 g, Yield 59%).

$^1$H NMR (400 MHz, DMSO-$d_6$) δ 1.24 (s, 12H), 5.33 (s, 2H), 7.38-7.20 (m, 5H), 7.60 (s, 1H), 8.03 (s, 1H),
MS (ESI) m/e (M+1)$^+$: 285.00

1-benzyl-1H-pyrazol-4-ol (i35)

To a stirred solution of 1-benzyl-4-(4,4,5,5-tetramethyl-1,3,2-dioxaborolan-2-yl)-1H-pyrazole (i34) (2.58 g, 9.08 mmol) in THF (25 mL), NaOH (0.726 g, 18.16 mmol) was added. The reaction was cooled at 0° C. and $H_2O_2$ (0.617 g, 18.16 mmol) was added drop wise. The reaction mixture was stirred at room temperature for 4 h. The progress of the reaction was monitored by TLC. After completion, the mixture was quenched with $Na_2S_2O_3$ solution and extracted with ethyl acetate. The organic layer was separated, dried over anhydrous sodium sulphate and concentrated under reduced pressure. The crude product was purified by silica gel (100-200 mesh) column chromatography using 10% ethyl acetate in n-hexanes as eluent to afford 1-benzyl-1H-pyrazol-4-ol (i35) (0.28 g, Yield 18%).

$^1$H NMR (400 MHz, DMSO-$d_6$) δ 5.13 (s, 2H), 7.01 (s, 1H), 7.13-7.21 (m, 2H), 7.22-7.37 (m, 3H), 8.39 (s, 1H),
MS (ESI) m/e (M+1)$^+$: 174.90

1-benzyl-4-methoxy-1H-pyrazole (i36)

To a stirred solution of 1-benzyl-1H-pyrazol-4-ol (i35) (0.26 g, 1.51 mmol) in DMF (7.5 mL), MeI (0.3 g, 2.11 mmol) and $Cs_2CO_3$ (0.685 g, 2.11 mmol) were added and the reaction was stirred at room temperature for 3 h. The progress of the reaction was monitored by TLC. After completion of the reaction, the solvent was removed under reduced pressure. The residue was diluted with ethyl acetate and washed with brine solution. The organic layer was separated, dried over anhydrous sodium sulphate and concentrated under reduced pressure to afford 1-benzyl-4-methoxy-1H-pyrazole (i36) (0.22 g, Yield—79%).

$^1$H NMR (400 MHz, DMSO-$d_6$) δ 3.64 (s, 3H), 5.19 (s, 2H), 7.38-7.54 (m, 7H).
MS (ESI) m/e (M+1)$^+$: 189.00

4-methoxy-1H-pyrazole (i37)

To a stirred solution of 1-benzyl-4-methoxy-1H-pyrazole (i36) ((0.22 g, 1.17 mmol) in methanol (70 mL), 1 M HCl (3 mL) and Pd(OH)$_2$/C (0.22 g) were added and the reaction was stirred at room temperature under hydrogen pressure in an autoclave for 8 h. The progress of the reaction was monitored by TLC. After completion, the mixture was filtered through celite and concentrated under reduced pressure. The crude product was purified by basic alumina column chromatography using 3% methanolic ammonia in dichloromethane as eluent to afford 4-methoxy-1H-pyrazole (i37) (0.09 g, Yield 78%).

MS (ESI) m/e (M+1)$^+$: 99.00

2-(4-methoxy-1H-pyrazol-1-yl)-9-((2-(trimethylsilyl)ethoxy)methyl)-9H-pyrrolo[2,3-b:4,5-c]dipyridine (i38)

2-chloro-9-((2-(trimethylsilyl)ethoxy)methyl)-9H-pyrrolo[2,3-b:4,5-c']dipyridine (i3) (0.25 g, 0.75 mmol) and 4-methoxy-1H-pyrazole (i37) (0.088 g, 0.9 mmol) were reacted according to procedure J to afford 2-(4-methoxy-1H-pyrazol-1-yl)-9-((2-(trimethylsilyl)ethoxy)methyl)-9H-pyrrolo[2,3-b:4,5-c']dipyridine (i38) (0.168 g, Yield 57%).

$^1$H NMR (400 MHz, DMSO-d$_6$) δ −0.21 (s, 9H), 0.86 (t, J=8.4 Hz, 2H), 3.58 (t, J=8.4 Hz, 2H), 3.84 (s, 3H), 5.96 (s, 2H), 7.71 (s, 1H), 7.90 (d, J=8.0 Hz, 2H), 8.10 (s, 1H), 8.50 (d, J=5.3 Hz, 1H), 8.79 (d, J=8.3 Hz, 2H).

MS (ESI) m/e (M+1)$^+$: 396.00

2-(4-methoxy-1H-pyrazol-1-yl)-9H-pyrrolo[2,3-b:4,5-c']dipyridine (Example 31)

SEM deprotection of 2-(4-methoxy-1H-pyrazol-1-yl)-9-((2-(trimethylsilyl)ethoxy)methyl)-9H-pyrrolo[2,3-b:4,5-c']dipyridine (i38) (0.16 g, 0.40 mmol) was performed according to procedure F to afford 2-(4-methoxy-1H-pyrazol-1-yl)-9H-pyrrolo[2,3-b:4,5-c']dipyridine (0.023 g, Yield 21%).

$^1$H NMR (400 MHz, DMSO-d$_6$) δ 3.83 (s, 3H), 7.49 (d, J=5.6 Hz, 1H), 7.69 (s, 1H), 7.84 (d, J=8.3 Hz, 1H), 8.29 (s, 1H), 8.44-8.51 (m, 1H), 8.73 (d, J=8.4 Hz, 1H), 9.34 (s, 1H), 12.39 (s, 1H).

MS (ESI) m/e (M+1)$^+$: 266.00

Example 32. 4-(5-(9H-pyrrolo[2,3-b:4,5-c']dipyridin-2-yl)thiazol-2-yl)morpholine

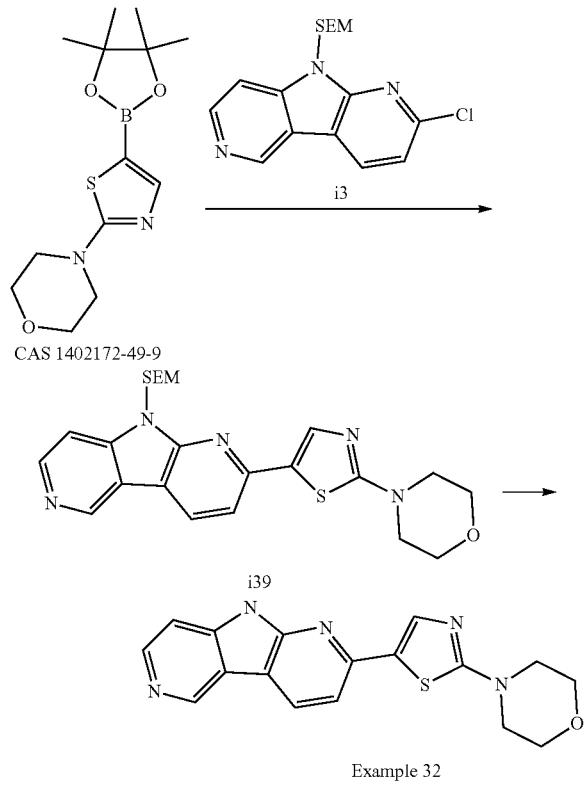

Example 32

4-(5-(9-((2-(trimethylsilyl)ethoxy)methyl)-9H-pyrrolo[2,3-b:4,5-c']dipyridin-2-yl)thiazol-2-yl)morpholine (i39)

2-chloro-9-((2-(trimethylsilyl)ethoxy)methyl)-9H-pyrrolo[2,3-b:4,5-c']dipyridine (i3) (0.2 g, 0.60 mmol) was reacted with 4-(5-(4,4,5,5-tetramethyl-1,3,2-dioxaborolan-2-yl)thiazol-2-yl)morpholine (0.23 g, 0.78 mmol) according to procedure D to afford 4-(5-(9-((2-(trimethylsilyl)ethoxy)methyl)-9H-pyrrolo[2,3-b:4,5-c']dipyridin-2-yl)thiazol-2-yl)morpholine (i39) (0.11 g, Yield 39%).

MS (ESI) m/e (M+1)$^+$: 467.65

4-(5-(9H-pyrrolo[2,3-b:4,5-c']dipyridin-2-yl)thiazol-2-yl)morpholine (Example 32)

SEM deprotection of 4-(5-(9-((2-(trimethylsilyl)ethoxy)methyl)-9H-pyrrolo[2,3-b:4,5-c']dipyridin-2-yl)thiazol-2-yl)morpholine (i39) (0.1 g, 0.21 mmol) was performed according to procedure F to afford 4-(5-(9H-pyrrolo[2,3-b:4,5-c']dipyridin-2-yl)thiazol-2-yl)morpholine (0.03 g, Yield 42%).

$^1$H NMR (400 MHz, DMSO-d$_6$) δ 3.49 (m, 4H), 3.75 (m, 4H), 7.42 (d, J=5.8 Hz, 1H), 7.77 (d, J=8.1 Hz, 1H), 8.03 (s, 1H), 8.44 (d, J=5.6 Hz, 1H), 8.55 (d, J=8.2 Hz, 1H), 9.30 (s, 1H), 12.25 (s, 1H)

MS (ESI) m/e (M+1)$^+$: 338.00

Example 33. 1-(4-(5-(9H-pyrrolo[2,3-b:4,5-c']dipyridin-2-yl)pyrimidin-2-yl)piperazin-1-yl)ethan-1-one

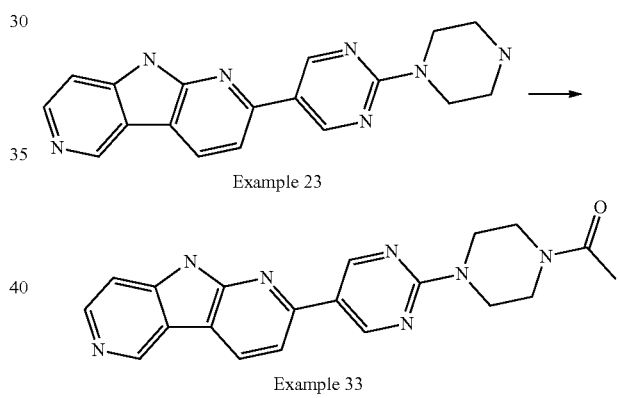

Example 33

To a stirred solution of 2-(2-(piperazin-1-yl)pyrimidin-5-yl)-9H-pyrrolo[2,3-b:4,5-c']dipyridine (Example 23) (0.07 g, 0.211 mmol) in DCM (6 mL), TEA (0.063 g, 0.633 mmol) was added followed by acetyl chloride (0.009 g, 0.169 mmol) at 0° C. and the solution was stirred at room temperature for 16 h. The progress of the reaction was monitored by TLC. After completion, the mixture was quenched with a saturated sodium bi-carbonate solution and extracted with 10% methanol in dichloromethane. The organic layer was separated, washed with water, dried over anhydrous sodium sulphate and concentrated under reduced pressure. The crude product was purified by neutral alumina column chromatography using 5% methanol in dichloromethane as eluent to 1-(4-(5-(9H-pyrrolo[2,3-b:4,5-c']dipyridin-2-yl)pyrimidin-2-yl)piperazin-1-yl)ethan-1-one (0.015 g, Yield 19%).

$^1$H NMR (400 MHz, DMSO-d$_6$) δ 2.07 (s, 3H), 3.62-3.44 (m, 4H), 3.89-3.82 (m, 4H), 7.45 (s, 1H), 7.87 (d, J=8.4 Hz, 1H), 8.47 (s, 1H), 8.70-8.62 (m, 1H), 9.17 (s, 2H), 9.35 (s, 1H), 12.32 (s, 1H)

MS (ESI) m/e (M+1)$^+$: 374.00

Example 34. 6-fluoro-N-(9H-pyrrolo[2,3-b:4,5-c']dipyridin-2-yl)nicotinamide

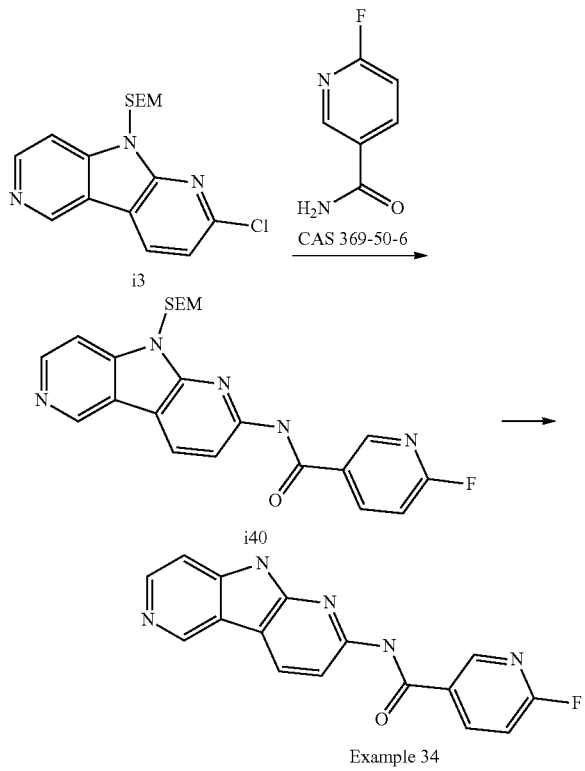

Example 34

6-fluoro-N-(9-((2-(trimethylsilyl)ethoxy)methyl)-9H-pyrrolo[2,3-b:4,5-c']dipyridin-2-yl)nicotinamide (i40)

To a stirred suspension of 2-chloro-9-((2-(trimethylsilyl)ethoxy)methyl)-9H-pyrrolo[2,3-b:4,5-c]dipyridine (i3) (0.1 g, 0.30 mmol), 6-fluoronicotinamide (0.05 g, 0.36 mmol), and $Cs_2CO_3$ (0.19 g, 0.60 mmol) in dioxane (5 mL), argon was purged for 15 min. BrettPhos precatalyst (0.035 g, 0.045 mmol) was then added and argon was purged for another 15 min. The reaction was heated at 100° C. for 16 h. The progress of the reaction was monitored by TLC. After completion, the mixture was diluted with water and extracted with ethyl acetate. The organic layer was separated, dried over anhydrous sodium sulphate and concentrated under reduced pressure. The crude product was purified by silica gel (230-400 mesh) column chromatography using 2% methanol in dichloromethane as eluent to afford 6-fluoro-N-(9-((2-(trimethylsilyl)ethoxy)methyl)-9H-pyrrolo[2,3-b:4,5-c']dipyridin-2-yl)nicotinamide (i40) (0.1 g, Yield 38%).

$^1$H NMR (400 MHz, DMSO-$d_6$) δ −0.15 (s, 9H), 0.83-0.86 (m, 2H), 3.52-3.69 (m, 2H), 5.87 (s, 2H), 7.35-7.38 (m, 1H), 7.75 (d, J=5.6 Hz, 1H), 8.21 (d, J=8.8 Hz, 1H), 8.53-8.58 (m, 2H), 8.71 (d, J=8.8 Hz, 1H), 8.87 (d, J=2.8 Hz, 1H), 9.36 (s, 1H), 11.27 (s, 1H),

MS (ESI) m/e (M+1)$^+$: 438.45

6-fluoro-N-(9H-pyrrolo[2,3-b:4,5-c']dipyridin-2-yl)nicotinamide (Example 34)

SEM deprotection of 6-fluoro-N-(9-((2-(trimethylsilyl)ethoxy)methyl)-9H-pyrrolo[2,3-b:4,5-c]dipyridin-2-yl)nicotinamide (i40) (0.1 g, 0.23 mmol) was performed according to procedure F to afford 6-fluoro-N-(9H-pyrrolo[2,3-b:4,5-c']dipyridin-2-yl)nicotinamide (0.04 g, Yield 57%).

$^1$H NMR (400 MHz, DMSO-$d_6$) δ 7.36 (dd, J=8.6, 2.7 Hz, 1H), 7.48 (d, J=5.6 Hz, 1H), 7.98-8.25 (m, 1H), 8.46 (d, J=5.8 Hz, 1H), 8.52-8.73 (m, 2H), 8.88 (d, J=2.5 Hz, 1H), 9.33 (s 1H), 11.20 (s, 1H), 12.03 (s, 1H).

MS (ESI) m/e (M+1)$^+$: 308.15

Example 35. 6-(methylamino)-N-(9H-pyrrolo[2,3-b:4,5-c']dipyridin-2-yl)nicotinamide

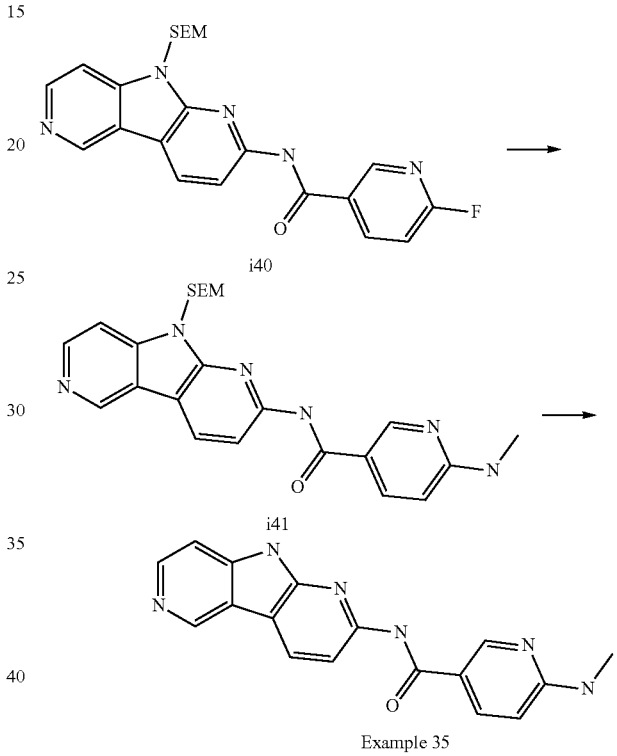

Example 35

6-(methylamino)-N-(9-((2-(trimethylsilyl)ethoxy)methyl)-9H-pyrrolo[2,3-b:4,5-c']dipyridin-2-yl)nicotinamide (i41)

A stirred solution of 6-fluoro-N-(9-((2-(trimethylsilyl)ethoxy)methyl)-9H-pyrrolo[2,3-b:4,5-c]dipyridin-2-yl)nicotinamide (i40) (0.1 g, 0.23 mmol) in 2 M methyl amine solution in THF (5 mL) was heated at 120° C. for 6 h. The progress of the reaction was monitored by TLC. After completion, the mixture was evaporated under reduced pressure. The crude product was purified by silica gel (230-400 mesh) column chromatography using 4% methanol in dichloromethane as eluent to afford 6-(methylamino)-N-(9-((2-(trimethylsilyl)ethoxy)methyl)-9H-pyrrolo[2,3-b:4,5-c]dipyridin-2-yl)nicotinamide (i41) (0.07 g, Yield 68%).

$^1$H NMR (400 MHz, DMSO-$d_6$) δ −0.15 (s, 9H), 0.79-0.89 (m, 2H), 2.85 (d, J=4.8 Hz, 3H), 3.57 (t, J=8.0 Hz, 2H), 5.87 (s, 2H), 6.50 (d, J=9.0 Hz, 1H), 7.23 (s, 1H), 7.72 (d, J=5.7 Hz, 1H), 8.03 (d, J=7.8 Hz, 1H), 8.19 (d, J=8.3 Hz, 1H), 8.53 (d, J=5.5 Hz, 1H), 8.64 (d, J=8.4 Hz, 1H), 8.76 (s, 1H), 9.33 (s, 1H), 10.60 (s, 1H).

MS (ESI) m/e (M+1)$^+$: 449.50

6-(methylamino)-N-(9H-pyrrolo[2,3-b:4,5-c']dipyridin-2-yl)nicotinamide (Example 35)

SEM deprotection of 6-(methylamino)-N-(9-((2-(trimethylsilyl)ethoxy)methyl)-9H-pyrrolo[2,3-b:4,5-c']dipyridin-2-yl)nicotinamide (i41) (0.07 g, 0.16 mmol) was performed according to procedure F to afford 6-(methylamino)-N-(9H-pyrrolo[2,3-b:4,5-c']dipyridin-2-yl)nicotinamide (0.019 g, Yield 37%).

$^1$H NMR (400 MHz, DMSO-$d_6$) δ 2.85 (d, J=4.7 Hz, 3H), 6.50 (d, J=8.8 Hz, 1H), 7.21 (d, J=5.6 Hz, 1H), 7.48 (d, J=4.8 Hz, 1H), 8.03 (d, J=8.6 Hz, 1H), 8.13 (d, J=8.5 Hz, 1H), 8.45 (s, 1H), 8.59 (d, J=8.5 Hz, 1H), 8.76 (d, J=2.4 Hz, 1H), 9.28 (s, 1H), 10.54 (s, 1H), 11.99 (s, 1H).

MS (ESI) m/e (M+1)$^+$: 319.00

Compounds of Formula I-A-2

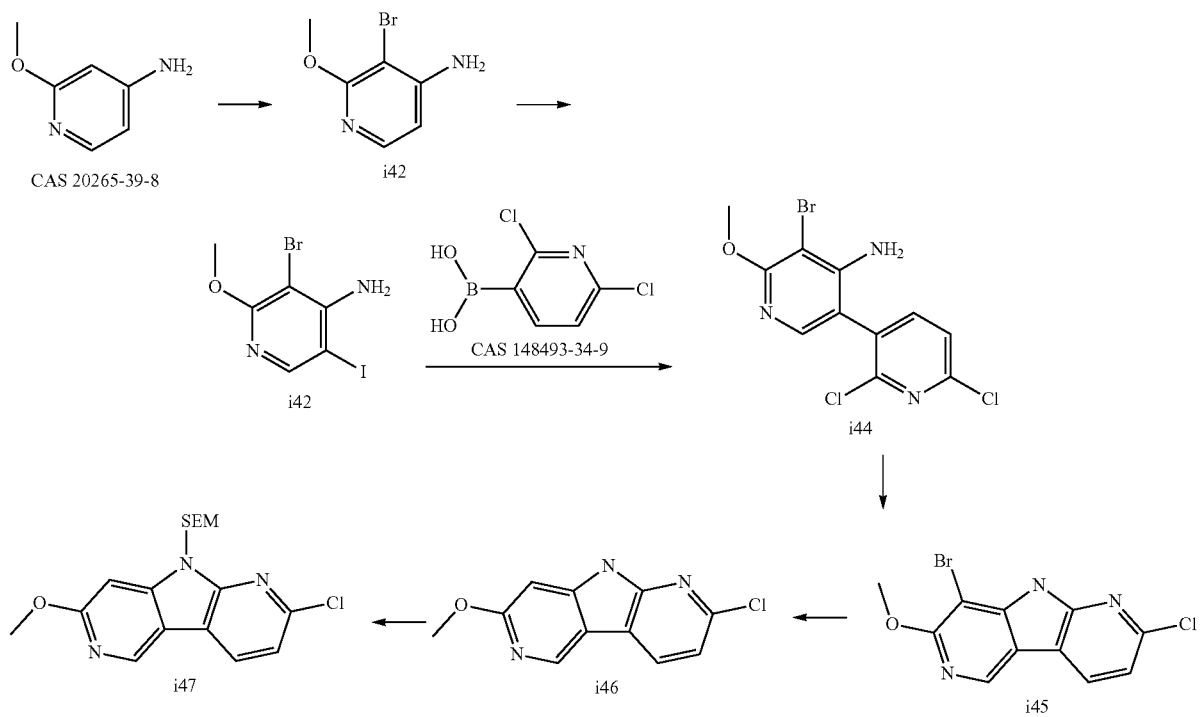

acetic acid (3 mL), NIS (3.55 g, 15.7 mmol) was added and the reaction was stirred at room temperature for 16 h. The progress of the reaction was monitored by TLC. After completion of the reaction, the solvent was removed under reduced pressure. The residue was dissolved in ethyl acetate and washed with water. The organic layer was separated, dried over anhydrous sodium sulphate and concentrated under reduced pressure. The crude product was purified by silica gel (100:200 mesh) column chromatography using 10% ethyl acetate in n-hexanes as eluent to afford 3-bromo-5-iodo-2-methoxypyridin-4-amine (i43) (4.6 g, Yield 97%).

$^1$H NMR (400 MHz, DMSO-$d_6$) δ 3.82 (s, 3H), 6.07 (s, 2H), 8.05 (s, 1H).

MS (ESI) m/e (M+1)$^+$: 330.95

3-bromo-2-methoxypyridin-4-amine (i42)

To a stirred solution of 2-methoxypyridin-4-amine (2 g, 16 mmol) in DCM (114 mL), NBS (2.87 g, 16 mmol) was slowly added at 0° C. and the reaction was stirred at room temperature for 2 h. The progress of the reaction was monitored by TLC. After completion, the solvent was concentrated under reduced pressure. The crude product was purified by silica gel (100:200 mesh) column chromatography using 15% ethyl acetate in n-hexanes as eluent to afford 3-bromo-2-methoxypyridin-4-amine (i42) (2.9 g, Yield 89%).

$^1$H NMR (400 MHz, Chloroform-d) δ 3.97 (s, 3H), 4.58 (s, 2H), 6.29 (d, J=5.7 Hz, 1H), 7.73 (d, J=5.6 Hz, 1H).

MS (ESI) m/e (M+1)$^+$: 203

3-bromo-5-iodo-2-methoxypyridin-4-amine (i43)

To a stirred solution of 3-bromo-2-methoxypyridin-4-amine (i42) (2.9 g, 14.3 mmol) in acetonitrile (122 mL) and 5-bromo-2',6'-dichloro-6-methoxy-[3,3'-bipyridin]-4-amine (i44)

3-bromo-5-iodo-2-methoxypyridin-4-amine (i43) (1 g, 3.0 mmol) was reacted with (2,6-dichloropyridin-3-yl)boronic acid (0.7 g, 3.6 mmol) according to procedure A to afford 5-bromo-2',6'-dichloro-6-methoxy-[3,3'-bipyridin]-4-amine (i44) (0.39 g, 38%).

$^1$H NMR (400 MHz, DMSO-$d_6$) δ 3.87 (s, 3H), 6.05 (s, 2H), 7.55 (s, 1H), 7.63 (d, J=7.9 Hz, 1H), 7.84 (d, J=7.9 Hz, 1H).

MS (ESI) m/e (M+1)$^+$: 330.95

8-bromo-2-chloro-7-methoxy-9H-pyrrolo[2,3-b:4,5-c']dipyridine (i45)

Cyclization of 5-bromo-2',6'-dichloro-6-methoxy-[3,3'-bipyridin]-4-amine (i44) (0.38 g, 1.08 mmol) was performed according to procedure B to afford 8-bromo-2-chloro-7-methoxy-9H-pyrrolo[2,3-b:4,5-c']dipyridine (i45) (0.27 g, Yield 87%).

$^1$H NMR (400 MHz, DMSO-d$_6$) δ 4.01 (s, 3H), 7.39 (d, J=8.1 Hz, 1H), 8.56 (d, J=8.1 Hz, 1H), 8.97 (s, 1H), 12.59 (s, 1H),
MS (ESI) m/e (M+2)+: 314.10

2-chloro-7-methoxy-9H-pyrrolo[2,3-b:4,5-c']dipyridine (i46)

To a stirred solution of 8-bromo-2-chloro-7-methoxy-9H-pyrrolo[2,3-b:4,5-c']dipyridine (i45) (0.26 g, 0.83 mmol) in 1,4-dioxane:water (4.5 mL: 0.5 mL), Na$_2$CO$_3$ (0.263, 2.4 mmol) was added and the reaction was degassed with argon for 20 min. PdCl$_2$(dppf) (0.135 g, 0.16 mmol) was added and the reaction was heated at 100° C. for 16 h. The progress of the reaction was monitored by TLC. After completion, the mixture was filtered through celite and the filtrate was concentrated under reduced pressure. The crude product was purified by silica gel (100:200 mesh) column chromatography using 2% methanol in dichloromethane as eluent to afford 2-chloro-7-methoxy-9H-pyrrolo[2,3-b:4,5-c']dipyridine (i46) (0.045 g, Yield 22%).

$^1$H NMR (400 MHz, DMSO-d$_6$) δ 3.93 (s, 3H), 6.74 (s, 1H), 7.32 (d, J=8.1 Hz, 1H), 8.51 (d, J=8.0 Hz, 1H), 8.99 (s, 1H), 12.18 (s, 1H).
MS (ESI) m/e (M+1)$^+$: 234.00

2-chloro-7-methoxy-9-((2-(trimethylsilyl)ethoxy)methyl)-9H-pyrrolo[2,3-b:4,5-c']dipyridine (i47)

SEM protection of 2-chloro-7-methoxy-9H-pyrrolo[2,3-b:4,5-c']dipyridine (i46) (0.14 g, 0.6 mmol) was performed according to procedure E to afford 2-chloro-7-methoxy-9-((2-(trimethylsilyl)ethoxy)methyl)-9H-pyrrolo[2,3-b:4,5-c']dipyridine (i47) (0.17 g, Yield 78%).

$^1$H NMR (400 MHz, DMSO-d$_6$) δ −0.14 (s, 9H), 0.83 (t, J=8.0 Hz, 2H), 3.55 (t, J=8.0 Hz, 2H), 3.95 (s, 3H), 5.75 (s, 2H), 7.08 (s, 1H), 7.42 (d, J=8.0 Hz, 1H), 8.57 (d, J=8.0 Hz, 1H), 9.03 (s, 1H)
MS (ESI) m/e (M+1)$^+$: 363.90

Generic Reaction Scheme for Examples 36-39:

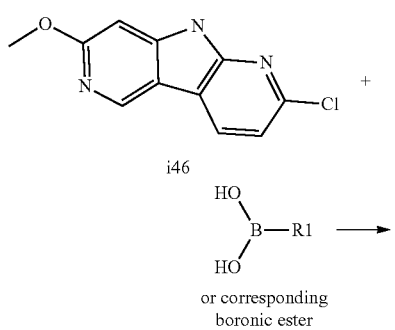

or corresponding boronic ester

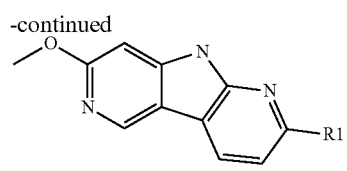

Examples 36-39

Example 36. 2-(6-fluoropyridin-3-yl)-7-methoxy-9H-pyrrolo[2,3-b:4,5-c']dipyridine 2-chloro-7-methoxy-9H-pyrrolo[2,3-b:4,5-c']dipyridine (i46) (0.04 g, 0.17 mmol) was reacted with (6-fluoropyridin-3-yl) boronic acid (0.04 g, 0.28 mmol) according to procedure C to afford 2-(6-fluoropyridin-3-yl)-7-methoxy-9H-pyrrolo[2,3-b:4,5-c']dipyridine (0.024 g, Yield 49%).

$^1$H NMR (400 MHz, DMSO-d$_6$) δ 3.94 (s, 3H), 6.72 (s, 1H), 7.34 (dd, J=8.9, 2.8 Hz, 1H), 7.92 (d, J=8.1 Hz, 1H), 8.55-8.74 (m, 2H), 8.99 (s, 2H), 12.10 (s, 1H).
MS (ESI) m/e (M+1)$^+$: 295

Example 37. 5-(7-methoxy-9H-pyrrolo[2,3-b:4,5-c']dipyridin-2-yl)-N-methylpicolinamide 2-chloro-7-methoxy-9H-pyrrolo[2,3-b:4,5-c']dipyridine (i46) (0.055 g, 0.23 mmol) was reacted with N-methyl-5-(4,4,5,5-tetramethyl-1,3,2-dioxaborolan-2-yl)picolinamide (0.074 g, 0.28 mmol) according to procedure C to afford 5-(7-methoxy-9H-pyrrolo[2,3-b:4,5-c']dipyridin-2-yl)-N-methylpicolinamide (0.042 g, Yield 54%).

$^1$H NMR (400 MHz, DMSO-d$_6$) δ 2.82 (d, J=4.8 Hz, 3H), 3.90 (s, 3H), 6.69 (s, 1H), 7.99 (d, J=8.1 Hz, 1H), 8.12 (d, J=8.2 Hz, 1H), 8.68-8.55 (m, 2H), 8.79 (d, J=5.7 Hz, 1H), 8.98 (s, 1H), 9.36-9.30 (m, 1H), 12.11 (s, 1H).
MS (ESI) m/e (M+1)$^+$: 334.00

Example 38. 7-methoxy-2-(1-methyl-1H-pyrazol-4-yl)-9H-pyrrolo[2,3-b:4,5-c']dipyridine 2-chloro-7-methoxy-9H-pyrrolo[2,3-b:4,5-c']dipyridine (i46) (0.07 g, 0.30 mmol), was reacted with 1-methyl-4-(4,4,5,5-tetramethyl-1,3,2-dioxaborolan-2-yl)-1H-pyrazole (0.094 g, 0.45 mmol) according to procedure C to afford 7-methoxy-2-(1-methyl-1H-pyrazol-4-yl)-9H-pyrrolo[2,3-b:4,5-c']dipyridine (0.039 g, Yield 45%).

$^1$H NMR (400 MHz, DMSO-d$_6$) δ 3.91 (s, 6H), 6.66 (s, 1H), 7.52 (d, J=8.0 Hz, 1H), 8.03 (s, 1H), 8.29 (s, 1H), 8.40 (d, J=8.0 Hz, 1H), 8.88 (s, 1H), 11.87 (s, 1H).
MS (ESI) m/e (M+1)$^+$: 280.15

Example 39. 4-(5-(7-methoxy-9H-pyrrolo[2,3-b:4,5-c']dipyridin-2-yl)pyrimidin-2-yl)morpholine 2-chloro-7-methoxy-9H-pyrrolo[2,3-b:4,5-c']dipyridine (i46) (0.06 g, 0.257 mmol) was reacted with 4-(5-(4,4,5-trimethyl-1,3,2-dioxaborolan-2-yl)pyrimidin-2-yl)morpholine (0.107 g, 0.386 mmol) according to procedure C to afford 4-(5-(7-methoxy-9H-pyrrolo[2,3-b:4,5-c']dipyridin-2-yl)pyrimidin-2-yl)morpholine (0.061 g, Yield 65%).

$^1$H NMR (400 MHz, DMSO-d$_6$) δ 3.80-3.70 (m, 8H), 3.92 (s, 3H), 6.68 (s, 1H), 7.78 (d, J=7.5 Hz, 1H), 8.50 (d, J=7.3 Hz, 1H), 8.94 (s, 1H), 9.12 (s, 2H), 12.03 (s, 1H).
MS (ESI) m/e (M+1)$^+$: 363.00

Example 40. 6-(7-methoxy-9H-pyrrolo[2,3-b:4,5-c']dipyridin-2-yl)-N-methylnicotinamide

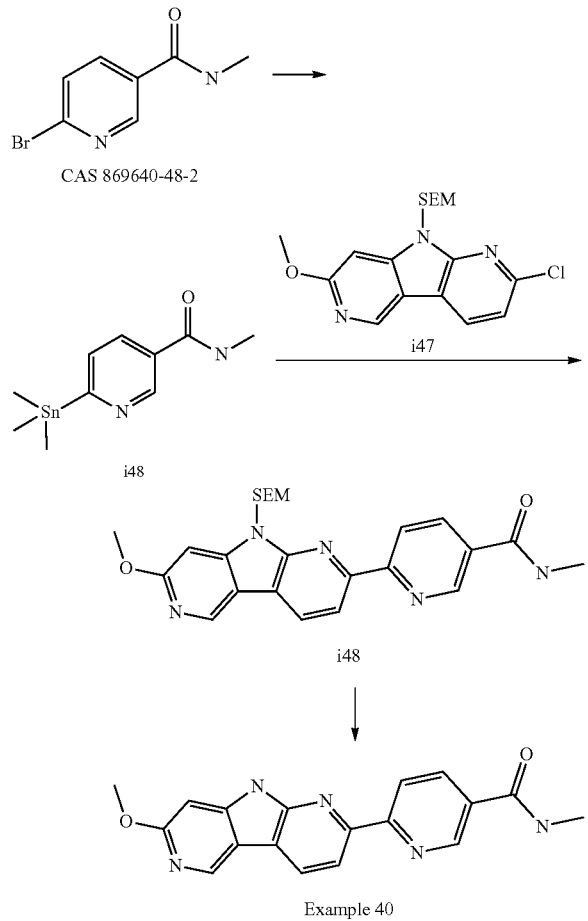

Example 40

N-methyl-6-(trimethylstannyl) nicotinamide (i48)

To a stirred solution of 6-bromo-N-methylnicotinamide (0.2 g, 1.16 mmol) in DME (15 mL), hexamethylditin (0.459 g, 1.4 mmol) was added and the reaction was degassed with argon for 30 min. Pd(PPh₃)₄ (0.067 g, 0.057 mmol) was added and the mixture was further degassed with argon for 10 min. The reaction was heated at 80° C. for 16 h. The progress of the reaction was monitored by TLC. After completion, the reaction mixture was used as such in the next step without any work up and analysis.

6-(7-methoxy-9-((2-(trimethylsilyl)ethoxy)methyl)-9H-pyrrolo[2,3-b:4,5-c']dipyridin-2-yl)-N-methylnicotinamide (i49)

A stirred solution of N-methyl-6-(trimethylstannyl)nicotinamide (i48) (0.346 g, 1.16 mmol) and 2-chloro-7-methoxy-9-((2-(trimethylsilyl)ethoxy)methyl)-9H-pyrrolo[2,3-b:4,5-c']dipyridine (i47) (0.16 g, 0.44 mmol) in DME (15 mL) was degassed with argon for 10 min and the reaction was heated at 110° C. for 16 h. The progress of the reaction was monitored by TLC. After completion of the reaction, the solvent was removed under reduced pressure. The crude product was purified by silica gel (230:400 mesh) column chromatography using 3% methanol in DCM to afford 6-(7-methoxy-9-((2-(trimethylsilyl)ethoxy)methyl)-9H-pyrrolo[2,3-b:4,5-c']dipyridin-2-yl)-N-methylnicotinamide (i49) (0.2 g, Yield 54%).

$^1$H NMR (400 MHz, DMSO-$d_6$) δ −0.19 (s, 9H), 0.88 (t, J=8.0 Hz, 2H), 2.85 (d, J=4.4 Hz, 3H), 3.63 (t, J=8.0 Hz, 2H), 3.97 (s, 3H), 5.93 (s, 2H), 7.06 (s, 1H), 8.35 (d, J=8.0 Hz, 1H), 8.45 (d, J=8.0 Hz, 1H), 8.75-8.59 (m, 3H), 9.06 (s, 1H), 9.11 (s, 1H).

MS (ESI) m/e (M+1)⁺: 464.00

6-(7-methoxy-9H-pyrrolo[2,3-b:4,5-c']dipyridin-2-yl)-N-methylnicotinamide (Example 40)

To a stirred solution of 6-(7-methoxy-9-((2-(trimethylsilyl)ethoxy)methyl)-9H-pyrrolo[2,3-b:4,5-c]dipyridin-2-yl)-N-methylnicotinamide (i49) (0.1 g, 0.215 mmol) in DCM (4 mL), TFA (2 mL) was added at 0° C. and the reaction was stirred at room temperature for 16 h. The solvent was removed under reduced pressure. The residue was dissolved in acetonitrile (4 mL) and ammonium hydroxide (4 mL). The reaction was stirred at room temperature for 2 h. The progress of the reaction was monitored by TLC. After completion, the mixture was filtered. The solid was washed with acetonitrile (4 mL) and pentane (10 mL) and dried under vacuum to afford 6-(7-methoxy-9H-pyrrolo[2,3-b:4,5-c']dipyridin-2-yl)-N-methylnicotinamide (0.023 g, 32%).

$^1$H NMR (400 MHz, DMSO-$d_6$) δ 2.84 (brs, 3H), 3.94 (brs, 3H), 6.74 (s, 1H), 8.32-8.35 (m, 5H), 9.02 (s, 1H), 9.10 (s, 1H), 12.11 (s, 1H).

MS (ESI) m/e (M+1)⁺: 334.00

Example 41. 5-(7-methoxy-9H-pyrrolo[2,3-b:4,5-c']dipyridin-2-yl)pyrimidine-2-carbonitrile

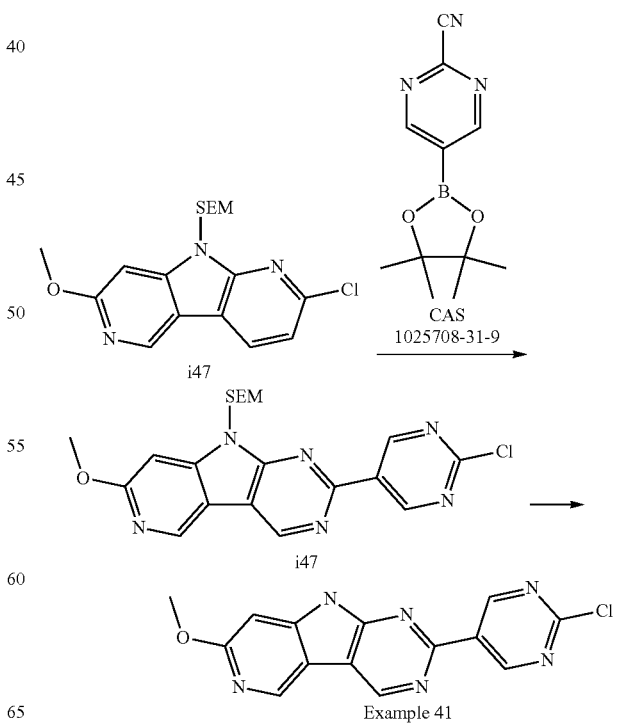

Example 41

5-(7-methoxy-9-((2-(trimethylsilyl)ethoxy)methyl)-9H-pyrrolo[2,3-b:4,5-c']dipyridin-2-yl)pyrimidine-2-carbonitrile (i48)

To a stirred solution of 2-chloro-7-methoxy-9-((2-(trimethylsilyl)ethoxy)methyl)-9H-pyrrolo[2,3-b:4,5-c']dipyridine (i47) (0.17 g, 0.468 mmol) and 5-(4,4,5,5-tetramethyl-1,3,2-dioxaborolan-2-yl)pyrimidine-2-carbonitrile (0.162 g, 0.702 mmol) in dioxane (15 mL), KF (0.135 g, 2.341 mmol) was added and the reaction was degassed with argon for 20 min. Pd$_2$(dba)$_3$ (0.043 g, 0.046 mmol) and X-phos (0.067 g, 0.14 mmol) were added and the mixture was further degassed for another 10 min. The reaction was heated at 100° C. for 2 h. The progress of the reaction was monitored by TLC. After completion of the reaction, the solvent was removed under reduced pressure. The crude product was purified by silica gel (230:400 mesh) column chromatography using 0.5 methanol in DCM to afford 5-(7-methoxy-9-((2-(trimethylsilyl)ethoxy)methyl)-9H-pyrrolo[2,3-b:4,5-c']dipyridin-2-yl)pyrimidine-2-carbonitrile (i48) (0.09 g, Yield 44%).

$^1$H NMR (400 MHz, DMSO-d$_6$) δ −0.18 (s, 9H), 0.86 (t, J=7.9 Hz, 2H), 3.62 (t, J=7.9 Hz, 2H), 3.97 (s, 3H), 5.92 (s, 2H), 7.06 (s, 1H), 8.25 (d, J=8.0 Hz, 1H), 8.73 (d, J=8.0 Hz, 1H), 9.08 (s, 1H), 9.80 (s, 2H).

MS (ESI) m/e (M+1)$^+$: 433.05

5-(7-methoxy-9H-pyrrolo[2,3-b:4,5-c']dipyridin-2-yl)pyrimidine-2-carbonitrile (Example 41)

SEM deprotection of 5-(7-methoxy-9-((2-(trimethylsilyl)ethoxy)methyl)-9H-pyrrolo[2,3-b:4,5-c]dipyridin-2-yl)pyrimidine-2-carbonitrile (i48) (0.06 g, 0.138 mmol) was performed according to procedure F to afford 5-(7-methoxy-9H-pyrrolo[2,3-b:4,5-c']dipyridin-2-yl)pyrimidine-2-carbonitrile (0.03 g, 72%).

$^1$H NMR (400 MHz, DMSO-d$_6$) δ 3.94 (s, 3H), 6.74 (s, 1H), 8.15 (d, J=8.0 Hz, 1H), 8.69 (d, J=7.9 Hz, 1H), 9.05 (s, 1H), 9.70 (s, 2H), 12.30 (s, 1H),

MS (ESI) m/e (M+1)$^+$: 303.00

Compounds of Formula I-A-3

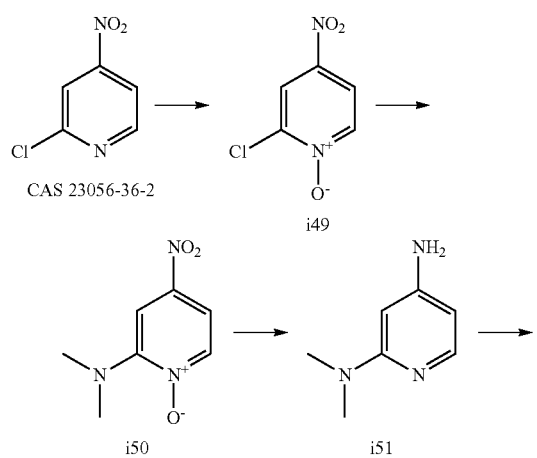

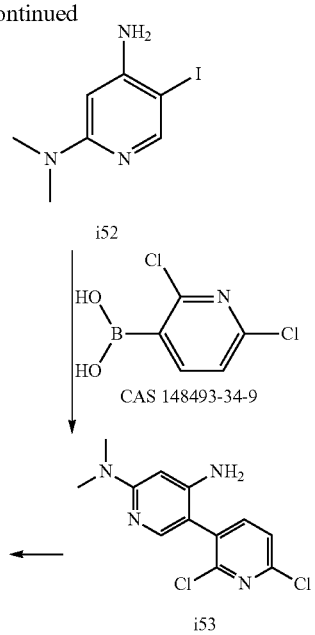

2-chloro-4-nitropyridine 1-oxide (i49)

To a stirred solution of 2-chloro-4-nitropyridine (5 g, 31.54 mmol) and urea. H$_2$O$_2$ (6.23 g, 66.20 mmol) in DCM (75 mL), TFAA (13.24 g, 63 mmol) was slowly added at 0° C. and the reaction was stirred for 30 min at same temperature then at room temperature for 4 h. Ammonia gas was bubbled into the reaction. The progress of the reaction was monitored by TLC. After completion, the mixture was concentrated under reduced pressure. The crude product was purified by silica gel (100:200 mesh) column chromatography using 1% methanol in dichloromethane as eluent to afford 2-chloro-4-nitropyridine 1-oxide (i49) (4.6 g, Yield 84%).

$^1$H NMR (400 MHz, DMSO-d$_6$): δ 8.19 (dd, J=7.2, 3.2 Hz, 1H), 8.64 (d, J=7.2 Hz, 1H), 8.72 (d, J=3.2 Hz, 1H).

2-(dimethylamino)-4-nitropyridine 1-oxide (i50)

To a stirred solution of 2-chloro-4-nitropyridine 1-oxide (i49) (2.1 g, 12 mmol) in THF:Ethanol 1:1 (50 mL), a 2 M dimethylamine solution in THF (1.24 g, 27.6 mmol) was added drop wise and the reaction was heated at 90° C. for 5 h. The progress of the reaction was monitored by TLC. After completion, the mixture was concentrated under reduced pressure. The crude product was purified by silica gel (100:200 mesh) column chromatography using 2% methanol in dichloromethane as eluent to afford 2-(dimethylamino)-4-nitropyridine 1-oxide (i50) (2.0 g, 91%).

$^1$H NMR (400 MHz, Chloroform-d) δ 3.11 (s, 6H), 7.64 (m, 2H), 8.21 (d, J=7.0 Hz, 1H).

MS (ESI) m/e (M+1)$^+$: 184

N$^2$,N$^2$-dimethylpyridine-2,4-diamine (i51)

To a stirred solution of 2-(dimethylamino)-4-nitropyridine 1-oxide (i50) (2 g, 10.92 mmol) in methanol (100 mL), Raney nickel (2 g) was added and the reaction was heated at 50° C. under hydrogen pressure for 22 h. The progress of the reaction was monitored by TLC. After completion, reaction was filtered through celite and the filtrate was concentrated under reduced pressure. The crude product was purified by silica gel (100:200 mesh) column chromatography using 6% methanolic ammonia in dichloromethane as eluent to afford $N^2,N^2$-dimethylpyridine-2,4-diamine (i51) (1.1 g, Yield 74%).

$^1$H NMR (400 MHz, DMSO-$d_6$) δ 2.89 (s, 6H), 5.57 (s, 2H), 5.68 (d, J=1.8 Hz, 1H), 5.84 (dd, J=5.6, 1.8 Hz, 1H), 7.58 (d, J=5.6 Hz, 1H).

MS (ESI) m/e (M+1)$^+$: 138.05

5-iodo-$N^2,N^2$-dimethylpyridine-2,4-diamine (i52)

To a solution of $N^2,N^2$-dimethylpyridine-2,4-diamine (i51) (0.5 g, 3.6 mmol) in acetic acid (20 mL), sodium acetate (0.89 g, 10.8 mmol) was added and the reaction was cooled to 15° C. ICI solution (0.63 g, 3.9 mmol) in acetic acid was added drop wise and the reaction was stirred at 15° C. for 20 min. The progress of the reaction was monitored by TLC. After completion, the mixture was diluted with water and extracted with ethyl acetate. The organic layer was dried over sodium sulphate and concentrated under reduced pressure. The crude product was purified by silica gel (100:200 mesh) column chromatography using 5% methanolic ammonia in dichloromethane as eluent to afford 5-iodo-$N^2,N^2$-dimethylpyridine-2,4-diamine (i52) (0.46 g, Yield 48%).

$^1$H NMR (400 MHz, DMSO-$d_6$) 2.89 (s, 6H), 5.68 (s, 2H), 5.91 (s, 1H), δ 7.93 (s, 1H), MS (ESI) m/e (M+1)$^+$: 263.80

2',6'-dichloro-$N^6,N^6$-dimethyl-[3,3'-bipyridine]-4,6-diamine (i53)

To a stirred solution of 5-iodo-$N^2,N^2$-dimethylpyridine-2,4-diamine (i52) (0.45 g, 1.7 mmol) in dioxane (6 mL) (2,6-dichloropyridin-3-yl) boronic acid (0.392 g, 2.0 mmol) and $K_3PO_4$ (1.08, 5.1 mmol) solution in water (4.0 mL) were added and the reaction was degassed with argon for 20 min. Bis(triphenylphosphine)palladium(II) dichloride (0.179 g, 0.25 mmol) was added and the reaction was heated at 100° C. for 16 h in a sealed tube. The progress of the reaction was monitored by TLC. After completion, the mixture was filtered through celite and the filtrate was concentrated under reduced pressure. The crude product was purified by silica gel (100:200 mesh) column chromatography using 10% methanolic ammonia in dichloromethane as eluent to afford 2',6'-dichloro-$N^6,N^6$-dimethyl-[3,3'-bipyridine]-4,6-diamine (i53) (0.285 g, Yield 59%).

$^1$H NMR (400 MHz, DMSO-$d_6$) δ 2.96 (s, 6H), 5.57 (s, 2H), 7.50 (s, 1H), 7.57 (d, J=8.0 Hz, 1H), 7.79-7.74 (m, 2H).

MS (ESI) m/e (M+1)$^+$: 285

2-chloro-N,N-dimethyl-9H-pyrrolo[2,3-b:4,5-c'] dipyridin-7-amine (i54)

Cyclization of 2',6'-dichloro-$N^6,N^6$-dimethyl-[3,3'-bipyridine]-4,6-diamine (i53) (0.25 g, 0.88 mmol) was performed according to procedure B to afford 2-chloro-N,N-dimethyl-9H-pyrrolo[2,3-b:4,5-c]dipyridin-7-amine (i54) (0.18 g, Yield—83%).

$^1$H NMR (400 MHz, DMSO-$d_6$) δ 3.11 (s, 6H), 6.42 (s, 1H), 7.20 (d, J=8.0 Hz, 1H), 8.32 (d, J=8.0 Hz, 1H), 8.87 (s, 1H), 11.85 (s, 1H).

MS (ESI) m/e (M+1)$^+$: 246.90

Generic Reaction Scheme for Examples 42-44:

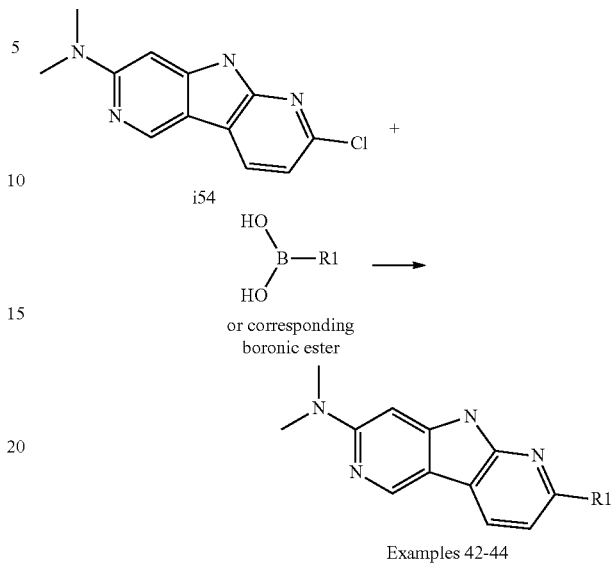

Examples 42-44

Example 42. 2-(6-fluoropyridin-3-yl)-N,N-dimethyl-9H-pyrrolo[2,3-b:4,5-c']dipyridin-7-amine 2-chloro-N,N-dimethyl-9H-pyrrolo[2,3-b:4,5-c']dipyridin-7-amine (i54) (0.06 g, 0.24 mmol) was reacted with (6-fluoropyridin-3-yl) boronic acid (0.051 g, 0.36 mmol) according to procedure C to afford 2-(6-fluoropyridin-3-yl)-N,N-dimethyl-9H-pyrrolo[2,3-b:4,5-c']dipyridin-7-amine (0.03 g, Yield 30%).

$^1$H NMR (400 MHz, DMSO-$d_6$) δ 3.11 (s, 6H), 6.40 (s, 1H), 7.36-7.34 (m, 1H), 7.82 (d, J=8.4 Hz, 1H), 8.40 (d, J=8.4 Hz, 1H), 8.70-8.64 (m, 1H), 8.90 (s, 1H), 8.98 (s, 1H), 11.80 (s, 1H).

MS (ESI) m/e (M+1)$^+$: 308.00

Example 43. 5-(7-(dimethylamino)-9H-pyrrolo[2,3-b:4,5-c']dipyridin-2-yl)-N-methylpicolinamide To a stirred suspension of 2-chloro-N,N-dimethyl-9H-pyrrolo[2,3-b:4,5-c']dipyridin-7-amine (i54) (0.06 g, 0.24 mmol), N-methyl-5-(4,4,5,5-tetramethyl-1,3,2-dioxaborolan-2-yl)picolinamide (0.082 g, 0.312 mmol) in dioxane: water 5:2 (7 mL), $K_3PO_4$ (0.155 g, 0.73 mmol) was added and purged with argon for 15 min. $Pd_2(dba)_3$ (0.022 g, 0.024 mmol) was then added and the reaction was heated at 100° C. for 3 h. The progress of the reaction was monitored by TLC. After completion, the solvent was evaporated to dryness. The crude product was purified by column chromatography on silica gel (230-400 mesh) using 5% methanol in dichloromethane to afford 5-(7-(dimethylamino)-9H-pyrrolo[2,3-b:4,5-c']dipyridin-2-yl)-N-methylpicolinamide (0.035 g, 42%).

$^1$H NMR (400 MHz, DMSO-$d_6$) δ 2.86 (d, J=4.8 Hz, 3H), 3.12 (s, 6H), 6.43 (s, 1H), 7.93 (d, J=8.0 Hz, 1H), 8.14 (d, J=8.2, 1H), 8.43 (d, J=8.0 Hz, 1H), 8.65 (dd, J=8.2, 2.2 Hz, 1H), 8.81 (m, 1H), 8.92 (s, 1H), 9.34 (s, 1H), 11.82 (s, 1H).

MS (ESI) m/e (M+1)$^+$: 347.30

Example 44. N,N-dimethyl-2-(1-methyl-1H-pyrazol-4-yl)-9H-pyrrolo[2,3-b:4,5-c']dipyridin-7-amine 2-chloro-N,N-dimethyl-9H-pyrrolo[2,3-b:4,5-c']dipyridin-7-amine (i54) (0.05 g, 0.20 mmol) was reacted with 1-methyl-4-(4,4,5,5-tetramethyl-1,3,2-dioxaborolan-2-yl)-1H-pyrazole (0.068 g, 0.30 mmol) according to procedure C to afford N,N-dimethyl-2-(1-methyl-1H-pyrazol-4-yl)-9H-pyrrolo[2,3-b:4,5-c']dipyridin-7-amine (0.035 g, 59%) $^1$H NMR (400 MHz, DMSO-d$_6$) δ 3.09 (s, 6H), 3.90 (s, 3H), 6.40 (s, 1H), 7.43 (d, J=8.0 Hz, 1H), 7.99 (S, 1H), 8.23 (m, 2H), 8.80 (s, 1H), 11.56 (s, 1H).
MS (ESI) m/e (M+1)$^+$: 293.20

Compounds of Formula I-A-4

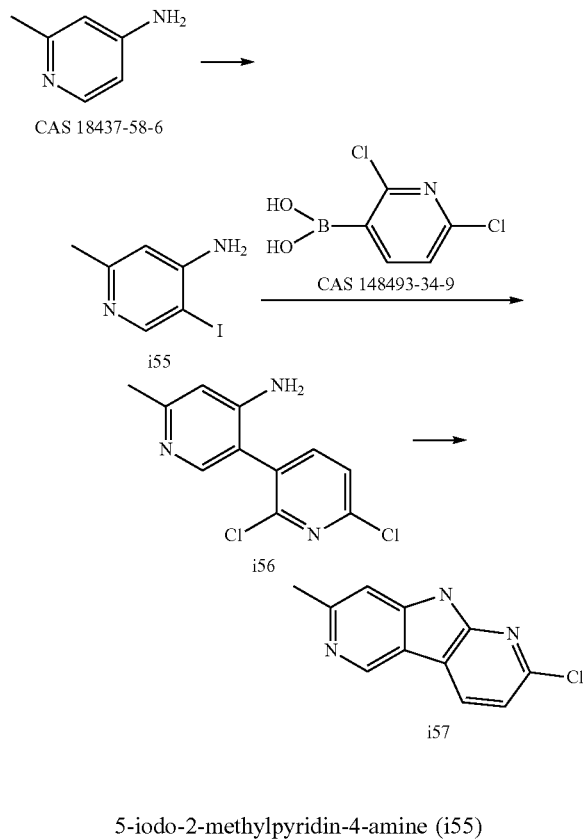

5-iodo-2-methylpyridin-4-amine (i55)

To a solution of 2-methylpyridin-4-amine (5 g, 46 mmol) in water (25 mL), Na$_2$CO$_3$ (3.4 g, 32 mmol) was added and the reaction mixture was refluxed. KI (9.8 g, 59 mmol) and I$_2$ (9.3 g, 36 mmol in 50 mL water) were added and refluxed for 7 h. The reaction mixture was quenched with sodium thiosulphate solution and the compound was extracted with DCM. The organic layer was separated dried over sodium sulphate and concentrated under reduced pressure. The residue obtained was purified by silica gel (100:200 mesh) column chromatography using 25% ethyl acetate in hexane as eluent to afford desired product 5-iodo-2-methylpyridin-4-amine (i55) (0.85 g, Yield 8%).
$^1$H NMR (400 MHz, DMSO-d$_6$): δ 2.20 (s, 3H), 6.00 (s, 2H), 6.49 (s, 1H), 8.22 (s, 1H).
MS (ESI) m/e (M+1)$^+$: 235

2',6'-dichloro-6-methyl-[3,3'-bipyridin]-4-amine (i56)

5-iodo-2-methylpyridin-4-amine (i55) (0.5 g, 2.1 mmol) was reacted with (2,6-dichloropyridin-3-yl)boronic acid (0.530 g, 2.77 mmol) according to procedure A to afford 2',6'-dichloro-6-methyl-[3,3'-bipyridin]-4-amine (i56) (0.22 g, Yield 41%).
$^1$H NMR (400 MHz, DMSO-d$_6$) δ 2.49 (s, 3H), 6.02 (s, 1H), 6.48 (s, 2H), 7.63 (dd, J=7.9, 1.2 Hz, 2H), 7.86-7.74 (m, 1H),
MS (ESI) m/e (M+1)$^+$: 255

2-chloro-7-methyl-9H-pyrrolo[2,3-b:4,5-c']dipyridine (i57)

Cyclization of 2',6'-dichloro-6-methyl-[3,3'-bipyridin]-4-amine (i56) (0.21 g, 0.82 mmol) was performed according to procedure B to afford 2-chloro-7-methyl-9H-pyrrolo[2,3-b:4,5-c']dipyridine (i57) (0.11 g, Yield 61%).
$^1$H NMR (400 MHz, DMSO-d$_6$) δ 2.57 (s, 3H), 7.28-7.39 (m, 2H), 8.57 (d, J=8.1 Hz, 1H), 9.17 (s, 1H), 12.15 (s, 1H),
MS (ESI) m/e (M+1)$^+$: 217.9
Generic Reaction Scheme for Examples 45-47:

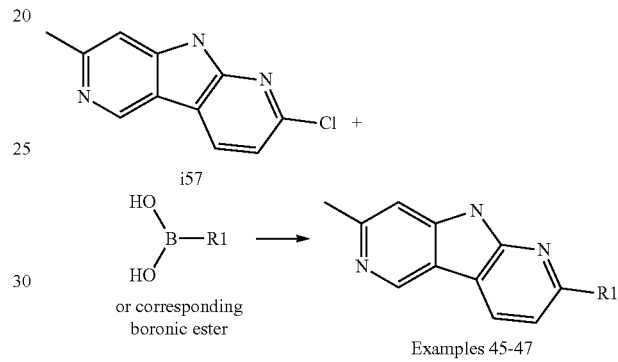

Examples 45-47

Example 45. 2-(6-fluoropyridin-3-yl)-7-methyl-9H-pyrrolo[2,3-b:4,5-c']dipyridine 2-chloro-7-methyl-9H-pyrrolo[2,3-b:4,5-c']dipyridine (i57) (0.08 g, 0.37 mmol), was reacted with (6-fluoropyridin-3-yl) boronic acid (0.078 g, 0.56 mmol) according to procedure C to afford 2-(6-fluoropyridin-3-yl)-7-methyl-9H-pyrrolo[2,3-b:4,5-c']dipyridine (0.034 g, Yield—33%).
$^1$H NMR (400 MHz, DMSO-d$_6$) δ 2.60 (s, 3H), 7.34-7.36 (m, 2H), 7.96 (d, J=8.4 Hz, 1H), 8.67-8.73 (m, 2H), 9.02 (s, 1H), 9.25 (s, 1H), 12.26 (s, 1H).
MS (ESI) m/e (M+1)$^+$: 279

Example 46. N-methyl-5-(7-methyl-9H-pyrrolo[2,3-b:4,5-c']dipyridin-2-yl)picolinamide 2-chloro-7-methyl-9H-pyrrolo[2,3-b:4,5-c']dipyridine (i57) (0.15 g, 0.69 mmol) was reacted with N-methyl-5-(4,4,5,5-tetramethyl-1,3,2-dioxaborolan-2-yl)picolinamide (0.27 g, 1.0 mmol) according to procedure C to afford N-methyl-5-(7-methyl-9H-pyrrolo[2,3-b:4,5-c']dipyridin-2-yl)picolinamide (0.06 g, Yield 28%).
$^1$H NMR (400 MHz, DMSO-d$_6$) δ 2.86 (d, J=4.8 Hz, 3H), 2.62 (s, 3H), 7.35 (s, 1H), 8.08 (d, J=8.1 Hz, 1H), 8.17 (d, J=8.2 Hz, 1H), 8.76-8.67 (m, 2H), 8.85 (d, J=5.1 Hz, 1H), 9.29 (s, 1H), 9.40 (s, 1H), 12.34 (s, 1H).
MS (ESI) m/e (M+1)$^+$: 318.00

Example 47. 3-methyl-7-(1-methyl-1H-pyrazol-4-yl)-5H-pyrrolo[3,2-c:4,5-c']dipyridine 2-chloro-7-methyl-9H-pyrrolo[2,3-b:4,5-c']dipyridine (i57) (0.1 g, 0.46 mmol) was reacted with 1-methyl-4-(4,4, 5,5-tetramethyl-1,3,2-dioxaborolan-2-yl)-1H-pyrazole (0.115 g, 0.55 mmol) according to procedure C to afford 3-methyl-7-(1-methyl-1H-pyrazol-4-yl)-5H-pyrrolo[3,2-c:4,5-c]dipyridine (0.088 g, Yield 73%).

¹H NMR (400 MHz, DMSO-d₆) δ 2.58 (s, 3H), 3.91 (s, 3H), 7.26 (s, 1H), 7.56 (d, J=8.3 Hz, 1H), 8.05 (s, 1H), 8.31 (s, 1H), 8.49 (d, J=8.1 Hz, 1H), 9.14 (s, 1H), 12.02 (s, 1H).

MS (ESI) m/e (M+1)⁺: 264.00

Compounds of Formula I-A-5

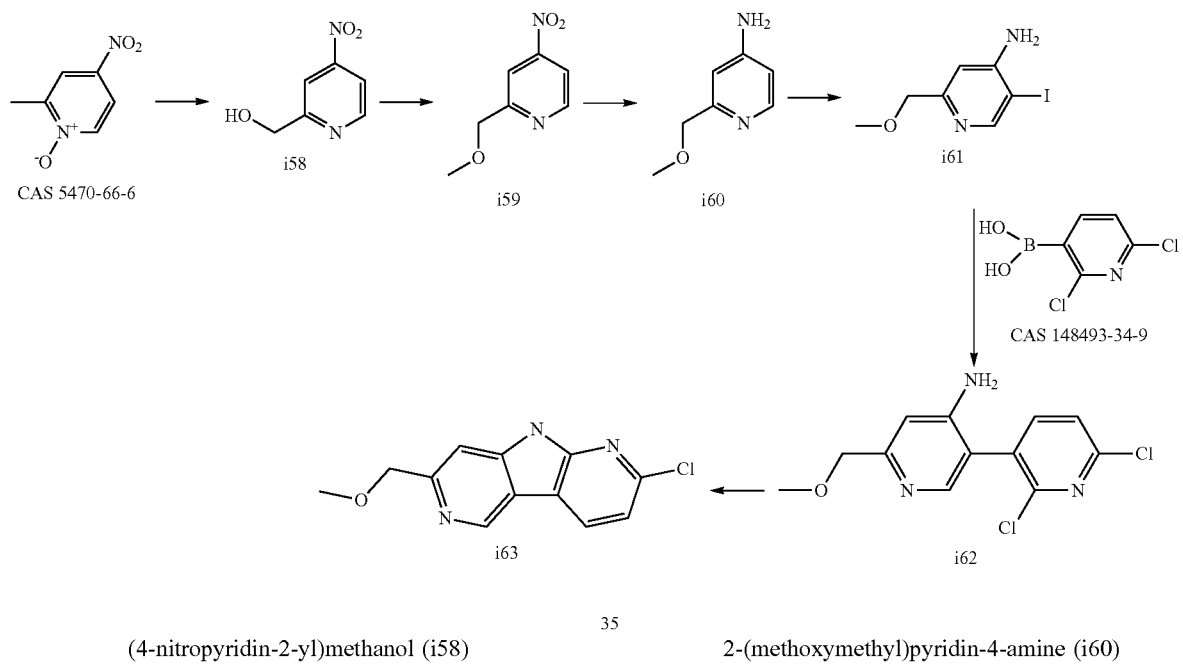

(4-nitropyridin-2-yl)methanol (i58)

To a stirred solution of 2-methyl-4-nitropyridine 1-oxide (5 g, 32.46 mmol) in DCM (50 mL), TFAA (20.44 g, 97.40 mmol) solution in DCM was added drop wise and the reaction was stirred at room temperature for 3 days. The progress of the reaction was monitored by TLC. After completion of the reaction, the solvent was evaporated under reduced pressure. The residue was diluted with methanol (100 mL) and saturated K₂CO₃ solution (50 mL). The resulting solution was stirred at room temperature for 4 h. The solvent was evaporated under reduced pressure. The residue was diluted with water and extracted with ethyl acetate. The organic layer was separated, dried over sodium sulphate and concentrated under reduced pressure to afford (4-nitropyridin-2-yl)methanol (i58) (4.5 g, Yield 97%).

¹H NMR (400 MHz, DMSO-d₆) δ 4.70 (s, 2H), 5.82 (s, 1H), 7.98 (d, J=5.2 Hz, 1H), 8.08 (s, 1H), 8.88 (d, J=5.2 Hz, 1H).

2-(methoxymethyl)-4-nitropyridine (i59)

To a solution of (4-nitropyridin-2-yl)methanol (i58) (2.3 g, 14.93 mmol) in THF (40 mL), NaH (0.89 g, 22.40 mmol) was added at 0° C. and stirred for 5 min. MeI (3.18 g, 22.4 mmol) was added and the reaction mixture allowed to warm to room temperature and stirred for 4 h. The progress of the reaction was monitored by TLC. After completion, the mixture was quenched with water and extracted with ethyl acetate. The organic layer was separated, dried over sodium sulphate and concentrated under reduced pressure. The crude product was purified by silica gel (60:120 mesh) column chromatography using 10% ethyl acetate in n-hexane as eluent to afford 2-(methoxymethyl)-4-nitropyridine (i59) (0.775 g, Yield 31%).

¹H NMR (400 MHz, DMSO-d₆) δ 3.44 (s, 3H), 4.66 (s, 2H), 8.08-8.00 (m, 2H), 8.91 (d, J=5.2 Hz, 1H).

MS (ESI) m/e (M+1)⁺: 169.00

2-(methoxymethyl)pyridin-4-amine (i60)

To a solution of 2-(methoxymethyl)-4-nitropyridine (i59) (1.5 g, 8.92 mmol) in ethanol (150 mL), Pd/C (0.7 g) was added and the reaction was stirred at room temperature under 100 psi hydrogen pressure in an autoclave for 3 h. The progress of the reaction was checked by TLC. After completion, the mixture was filtered through celite and filtrate was concentrated under reduced pressure to afford 2-(methoxymethyl)pyridin-4-amine (i60) (1.1 g, Yield 89%).

¹H NMR (400 MHz, DMSO-d₆) δ 3.43 (s, 3H), 4.26 (s, 2H), 5.98 (s, 2H), 6.34 (dd, J=5.5, 2.3 Hz, 1H), 6.53 (d, J=2.3 Hz, 1H), 7.89 (d, J=5.6 Hz, 1H).

MS (ESI) m/e (M+1)⁺: 139.00

5-iodo-2-(methoxymethyl)pyridin-4-amine (i61)

To a solution of 2-(methoxymethyl)pyridin-4-amine (i60) (1 g, 7.246 mmol) in water (40 mL), Na₂CO₃ (0.599 g, 5.72 mmol) was added and the reaction was heated at 100° C. KI (1.53 g, 9.275 mmol) and iodine (1.45 g, 5.72 mmol) were then added at the same temperature. The reaction was stirred at 100° C. for 2 h. The progress of the reaction monitored by TLC. After completion, the reaction mixture was quenched with water and extracted with ethyl acetate. The organic layer was separated, dried over sodium sulphate and concentrated under reduced pressure. The crude product was purified by silica gel (100-200 mesh) column chromatography using 50% ethyl acetate in n-hexanes as eluent to afford 5-iodo-2-(methoxymethyl)pyridin-4-amine (i61) (0.75 g, Yield 39%).

¹H NMR (400 MHz, DMSO-d₆) δ 3.34 (s, 3H), 4.26 (s, 2H), 6.17 (s, 2H), 6.70 (s, 1H), 8.28 (s, 1H).
MS (ESI) m/e (M+1)⁺: 265.00

2',6'-dichloro-6-(methoxymethyl)-[3,3'-bipyridin]-4-amine (i62)

5-iodo-2-(methoxymethyl)pyridin-4-amine (i61) (0.75 g, 2.84 mmol) was reacted with (2,6-dichloropyridin-3-yl)boronic acid (0.762 g, 3.97 mmol) according to procedure C to afford 2',6'-dichloro-6-(methoxymethyl)-[3,3'-bipyridin]-4-amine (i62) (0.6 g, Yield 75%).

¹H NMR (400 MHz, DMSO-d₆) δ 3.40 (s, 3H), 4.36 (s, 2H), 6.21 (s, 2H), 6.70 (s, 1H), 7.68-7.52 (m, 2H), 7.85 (d, J=6.9 Hz, 1H).
MS (ESI) m/e (M+1)⁺: 284.00

2-chloro-7-(methoxymethyl)-9H-pyrrolo[2,3-b:4,5-c']dipyridine (i63)

Cyclization of 2',6'-dichloro-6-(methoxymethyl)-[3,3'-bipyridin]-4-amine (i62) (1.2 g, 4.24 mmol) was performed according to procedure B to afford 2-chloro-7-(methoxymethyl)-9H-pyrrolo[2,3-b:4,5-c']dipyridine (i63) (0.55 g, Yield 55%).

¹H NMR (400 MHz, DMSO-d₆) δ 3.42 (s, 3H), 4.63 (s, 2H), 7.21-7.30 (m, 1H), 7.37 (d, J=8.1 Hz, 1H), 7.48 (s, 1H), 8.64 (d, J=8.1 Hz, 1H), 9.30 (s, 1H),
MS (ESI) m/e (M+1)⁺: 284.00

Generic Reaction Scheme for Examples 49-51:

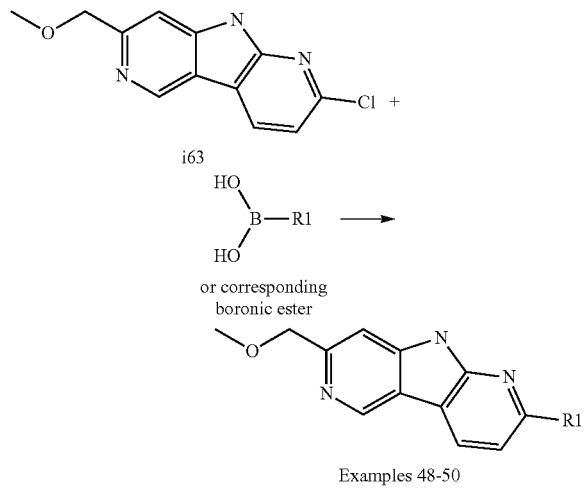

Examples 48-50

Example 48. 2-(6-fluoropyridin-3-yl)-7-(methoxymethyl)-9H-pyrrolo[2,3-b:4,5-c']dipyridine 2-chloro-7-(methoxymethyl)-9H-pyrrolo[2,3-b:4,5-c']dipyridine (i63) (0.08 g, 0.323 mmol) was reacted with (6-fluoropyridin-3-yl)boronic acid (0.068 g, 0.485 mmol) according to procedure D to afford 2-(6-fluoropyridin-3-yl)-7-(methoxymethyl)-9H-pyrrolo[2,3-b:4,5-c']dipyridine (0.046 g, 23%).

¹H NMR (400 MHz, DMSO-d₆) δ 3.44 (s, 3H), 4.64 (s, 2H), 7.36 (dd, J=8.8, 2.9 Hz, 1H), 7.48 (s, 1H), 8.00 (d, J=8.1 Hz, 1H), 8.72 (d, J=7.8 Hz, 2H), 9.03 (s, 1H), 9.32 (s, 1H), 12.38 (s, 1H),
MS (ESI) m/e (M+1)⁺: 309.10

Example 49. 5-(7-(methoxymethyl)-9H-pyrrolo[2,3-b:4,5-c']dipyridin-2-yl)-N-methylpicolinamide 2-chloro-7-(methoxymethyl)-9H-pyrrolo[2,3-b:4,5-c']dipyridine (i63) (0.08 g, 0.323 mmol) was reacted with 1-methyl-4-(4,4,5,5-tetramethyl-1,3,2-dioxaborolan-2-yl)picolinamide (0.127 g, 0.485 mmol) according to procedure C to afford 5-(7-(methoxymethyl)-9H-pyrrolo[2,3-b:4,5-c']dipyridin-2-yl)-N-methylpicolinamide (0.027 g, 24%).

¹H NMR (400 MHz, DMSO-d₆) δ 2.86 (d, J=4.8 Hz, 3H), 3.44 (s, 3H), 4.65 (s, 2H), 7.49 (s, 1H), 8.10 (d, J=8.1 Hz, 1H), 8.17 (d, J=8.3 Hz, 1H), 8.68-8.81 (m, 2H), 8.85 (d, J=5.2 Hz, 1H), 9.34 (s, 1H), 9.40 (d, J=2.2 Hz, 1H), 12.44 (s, 1H),
MS (ESI) m/e (M+1)⁺: 348.00

Example 50. 7-(methoxymethyl)-2-(1-methyl-1H-pyrazol-3-yl)-9H-pyrrolo[2,3-b:4,5-c]dipyridine 2-chloro-7-(methoxymethyl)-9H-pyrrolo[2,3-b:4,5-c']dipyridine (i63) (0.06 g, 0.249 mmol) was reacted with -methyl-4-(4,4,5,5-tetramethyl-1,3,2-dioxaborolan-2-yl)-1H-pyrazole (0.075 g, 0.364 mmol) according to procedure A to afford 7-(methoxymethyl)-2-(1-methyl-1H-pyrazol-3-yl)-9H-pyrrolo[2,3-b:4,5-c']dipyridine (0.019 g, 27%)

¹H NMR (400 MHz, DMSO-d₆) δ 3.42 (s, 3H), 3.92 (s, 3H), 4.62 (s, 2H), 7.42 (s, 1H), 7.60 (d, J=8.1 Hz, 1H), 8.06 (s, 1H), 8.33 (s, 1H), 8.54 (d, J=8.1 Hz, 1H), 9.21 (s, 1H), 12.15 (s, 1H).
MS (ESI) m/e (M+1)⁺: 294.00

Compounds of Formula I-B

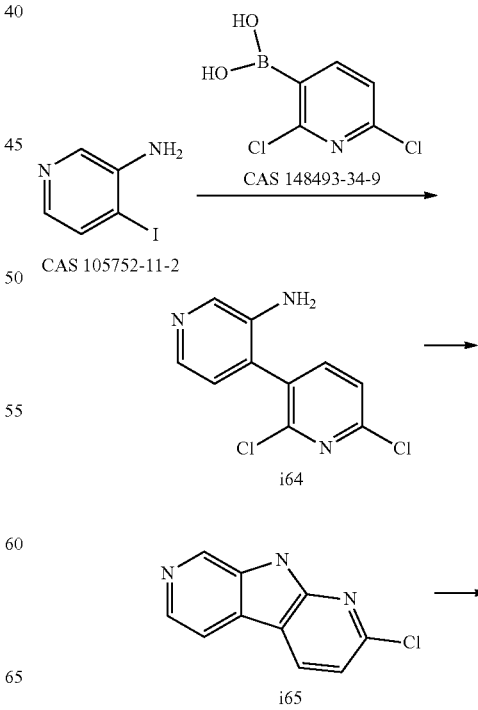

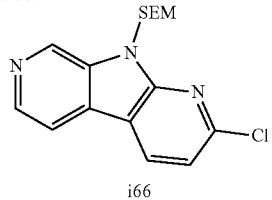

i66

2,6-dichloro-[3,4'-bipyridin]-3'-amine (i64)

To a stirred solution of 4-iodopyridin-3-amine (2 g, 9.0 mmol) in 1,4-dioxane (84 mL), (2,6-dichloropyridin-3-yl) boronic acid (2.4 g, 12.5 mmol) and $K_3PO_4$ (5.6 g, 26.0 mmol) solution in water (28 mL) were added and the reaction was degassed with argon for 20 min. $PdCl_2(PPh_3)_2$ (0.7 g, 0.99 mmol) was added and the reaction was heated in a sealed tube at 100° C. for 16 h. The progress of the reaction was monitored by TLC. After completion, the reaction was diluted with water and filtered. The aqueous layer was extracted with ethyl acetate. The organic layer was separated, dried over anhydrous sodium sulphate and concentrated under reduced pressure. The crude product was purified by silica gel (100:200 mesh) column chromatography using 2% methanol in dichloromethane as eluent to afford 2,6-dichloro-[3,4'-bipyridin]-3'-amine (i64) (1.08 g, Yield 51%).

$^1$H NMR (400 MHz, DMSO-$d_6$) δ 5.26 (s, 2H), 6.93 (d, J=4.9 Hz, 1H), 7.51-7.68 (m, 1H), 7.79-7.89 (m, 2H), 8.08 (s, 1H),

MS (ESI) m/e $(M+1)^+$: 240.00

2-chloro-9H-pyrrolo[2,3-b:5,4-c]dipyridine (i65)

Cyclization of 2,6-dichloro-[3,4'-bipyridin]-3'-amine (i64) (1 g, 4.1 mmol) was performed according to procedure B to afford 2-chloro-9H-pyrrolo[2,3-b:5,4-c]dipyridine (i65) (0.749 g Yield 89%).

$^1$H NMR (400 MHz, DMSO-$d_6$) δ 7.38 (d, J=8.2 Hz, 1H), 7.68 (s, 1H), 8.17 (d, J=7.3 Hz, 1H), 8.45 (d, J=7.1 1H), 8.72 (d, J=8.2 Hz, 1H), 8.97 (s, 1H),

MS (ESI) m/e $(M+1)^+$: 204.00

2-chloro-9-((2-(trimethylsilyl)ethoxy)methyl)-9H-pyrrolo[2,3-b:5,4-c']dipyridine (i66)

SEM protection of 2-chloro-9H-pyrrolo[2,3-b:5,4-c] dipyridine (i65) (0.74 g, 3.6 mmol) was performed according to procedure E to afford 2-chloro-9-((2-(trimethylsilyl) ethoxy)methyl)-9H-pyrrolo[2,3-b:5,4-c]dipyridine (i66) (0.31 g, Yield 26%).

$^1$H NMR (400 MHz, DMSO-$d_6$) δ -0.15 (s, 9H). 0.77-0.89 (m, 2H), 3.48-3.60 (m, 2H), 5.95 (s, 2H), 7.48 (d, J=8.2 Hz, 1H), 8.23 (d, J=5.3 Hz, 1H), 8.55 (d, J=5.2 Hz, 1H), 8.78 (d, J=8.1 Hz, 1H), 9.17 (s, 1H),

MS (ESI) m/e $(M+1)^+$: 334.00

Example 51. 2-(1-methyl-1H-pyrazol-4-yl)-9H-pyrrolo[2,3-b:5,4-c]dipyridine

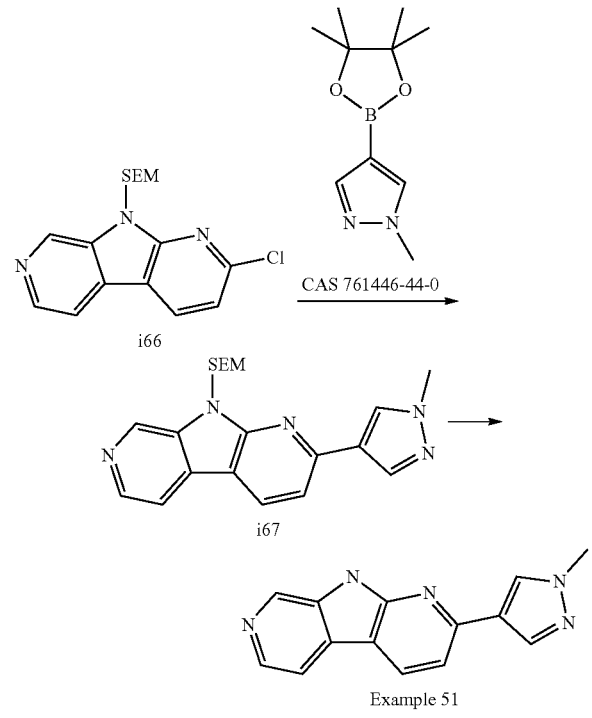

Example 51

2-(1-methyl-1H-pyrazol-4-yl)-9-((2-(trimethylsilyl) ethoxy)methyl)-9H-pyrrolo[2,3b:5,4c']dipyridine (i67)

2-chloro-9-((2-(trimethylsilyl)ethoxy)methyl)-9H-pyrrolo[2,3-b:5,4-c]dipyridine (i66) (0.2 g, 0.59 mmol) was reacted with 1-methyl-4-(4,4,5,5-tetramethyl-1,3,2-dioxaborolan-2-yl)-1H-pyrazole (0.160 g, 0.77 mmol) according to procedure C to afford 2-(1-methyl-1H-pyrazol-4-yl)-9-((2-(trimethylsilyl)ethoxy)methyl)-9H-pyrrolo[2,3b:5,4c'] dipyridine (i67) (0.105 g, Yield 47%).

$^1$H NMR (400 MHz, DMSO-$d_6$) δ -0.19 (s, 9H), 0.90 (t, J=8.1 Hz, 2H), 3.57 (t, J=8.1 Hz, 2H), 3.93 (s, 3H), 5.99 (s, 2H), 7.67 (d, J=8.1 Hz, 1H), 8.09-8.19 (m, 2H), 8.40-8.50 (m, 2H), 8.63 (d, J=8.1 Hz, 1H), 9.06 (s, 1H),

MS (ESI) m/e $(M+1)^+$: 380.00

2-(1-methyl-1H-pyrazol-4-yl)-9H-pyrrolo[2,3-b:5,4-c]dipyridine (Example 51)

SEM deprotection of 2-(1-methyl-1H-pyrazol-4-yl)-9-((2-(trimethylsilyl)ethoxy)methyl)-9H-pyrrolo[2,3b:5,4c'] dipyridine (i67) (0.1 g, 0.26 mmol) was performed according to procedure F to afford 2-(1-methyl-1H-pyrazol-4-yl)-9H-pyrrolo[2,3-b:5,4-c]dipyridine (0.03 g, Yield 47%).

$^1$H NMR (400 MHz, Methanol-$d_4$) δ 3.98 (s, 3H), 7.58 (d, J=8.0 Hz, 1H), 8.06 (d, J=5.8 Hz, 1H), 8.13 (s, 1H), 8.26 (s, 1H), 8.34 (d, J=5.4 Hz, 1H), 8.52 (d, J=7.8 Hz, 1H), 8.82 (s, 1H), MS (ESI) m/e $(M+1)^+$: 250.05

Example 52. 2-(1H-pyrazol-4-yl)-9H-pyrrolo[2,3-b:5,4-c]dipyridine

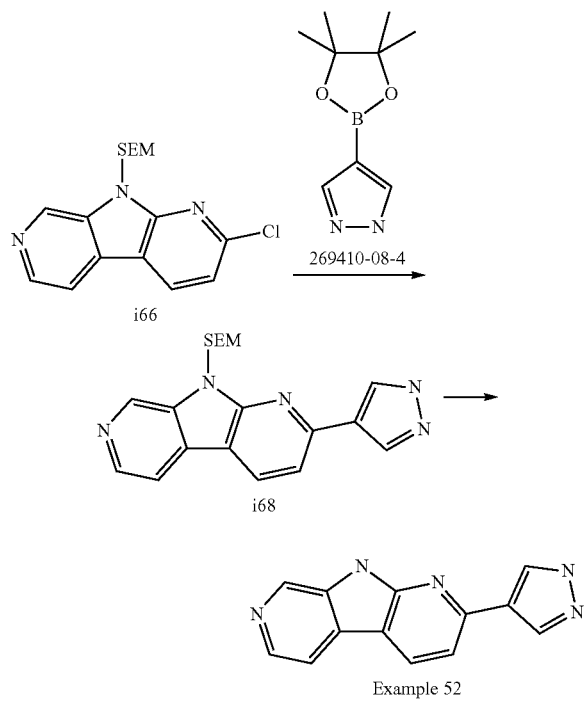

Example 52

2-(1H-pyrazol-4-yl)-9-((2-(trimethylsilyl)ethoxy)methyl)-9H-pyrrolo[2,3-b:5,4-c]dipyridine (i68)

2-chloro-9-((2-(trimethylsilyl)ethoxy)methyl)-9H-pyrrolo[2,3-b:5,4-c]dipyridine (i66) (0.2 g, 0.59 mmol) was reacted with 4-(4,4,5,5-tetramethyl-1,3,2-dioxaborolan-2-yl)-1H-pyrazole (0.152 g, 0.78 mmol) according to procedure G to afford 2-(1H-pyrazol-4-yl)-9-((2-(trimethylsilyl)ethoxy)methyl)-9H-pyrrolo[2,3-b:5,4-c]dipyridine (i68) (0.1 g, Yield 47%).

$^1$H NMR (400 MHz, DMSO-d$_6$) δ −0.19 (s, 9H), 0.95 (t, J=8.1 Hz, 2H), 3.57 (t, J=8.1 Hz, 2H), 6.01 (s, 2H), 7.69-7.76 (m, 1H), 8.12 (d, J=5.1 Hz, 1H), 8.20-8.26 (m, 1H), 8.44-8.52 (m, 2H), 8.64 (dd, J=8.2, 1.9 Hz, 1H), 9.06 (s, 1H), 13.17 (s, 1H),

MS (ESI) m/e (M+1)$^+$: 366.00

2-(1H-pyrazol-4-yl)-9H-pyrrolo[2,3-b:5,4-c]dipyridine (Example 52)

SEM deprotection of 2-(1H-pyrazol-4-yl)-9-((2-(trimethylsilyl)ethoxy)methyl)-9H-pyrrolo[2,3-b:5,4-c]dipyridine (i68) (0.1 g, 0.27 mmol) was performed according to procedure F to afford 2-(1H-pyrazol-4-yl)-9H-pyrrolo[2,3-b:5,4-c]dipyridine (0.03 g, Yield 48%).

$^1$H NMR (400 MHz, DMSO-d$_6$) δ 7.62-7.70 (m, 1H), 8.04-8.10 (m, 1H), 8.16 (s, 1H), 8.31-8.50 (m, 2H), 8.56-8.64 (m, 1H), 8.84 (s, 1H), 12.08 (s, 1H), 13.14 (s, 1H).

MS (ESI) m/e (M+1)$^+$: 236.05

Example 53. N-methyl-5-(9H-pyrrolo[2,3-b:5,4-c]dipyridin-2-yl)picolinamide

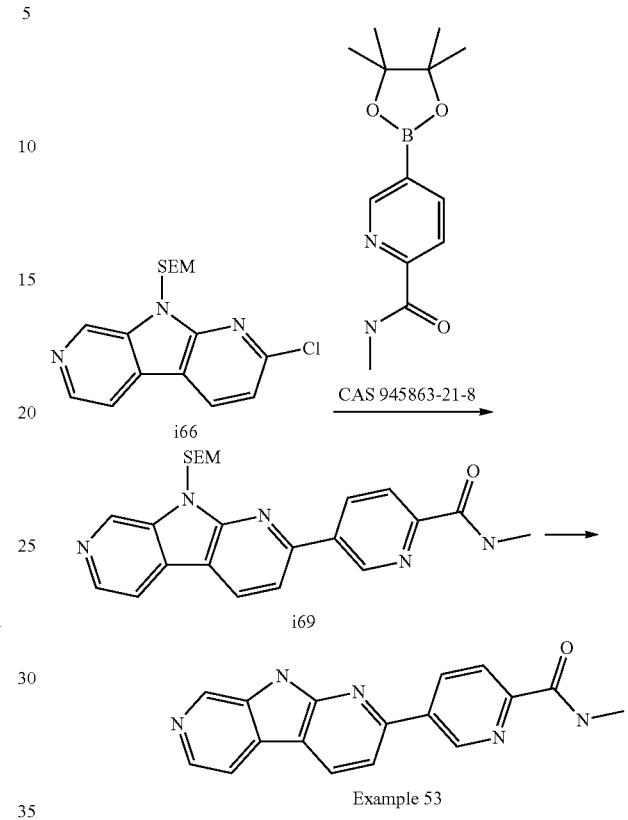

Example 53

N-methyl-5-(9-((2-(trimethylsilyl)ethoxy)methyl)-9H-pyrrolo[2,3-b:5,4-c]dipyridin-2-yl)picolinamide (i69)

2-chloro-9-((2-(trimethylsilyl)ethoxy)methyl)-9H-pyrrolo[2,3-b:5,4-c]dipyridine (i66) (0.2 g, 0.59 mmol) was reacted with N-methyl-5-(4,4,5,5-tetramethyl-1,3,2-dioxaborolan-2-yl)picolinamide (0.204 g, 0.78 mmol) according to procedure G to afford N-methyl-5-(9-((2-(trimethylsilyl)ethoxy)methyl)-9H-pyrrolo[2,3-b:5,4-c]dipyridin-2-yl)picolinamide (i69) (0.13 g, Yield 50%).

$^1$H NMR (400 MHz, DMSO-d$_6$) δ −0.22 (s, 9H), 0.93 (t, J=8.1 Hz, 2H), 2.87 (d, J=4.9 Hz, 3H), 3.67 (t, J=8.1 Hz, 2H), 6.09 (s, 2H), 8.13-8.29 (m, 3H), 8.55 (dd, J=5.2, 1.2 Hz, 1H), 8.79-8.92 (m, 3H), 9.17 (d, J=1.2 Hz, 1H), 9.50 (brs, 1H).

MS (ESI) m/e (M+1)$^+$: 434.00

N-methyl-5-(9H-pyrrolo[2,3-b:5,4-c]dipyridin-2-yl)picolinamide (Example 53)

SEM deprotection of N-methyl-5-(9-((2-(trimethylsilyl)ethoxy)methyl)-9H-pyrrolo[2,3-b:5,4-c]dipyridin-2-yl)picolinamide (i69) (0.12 g, 0.27 mmol) was performed according to procedure F to afford N-methyl-5-(9H-pyrrolo[2,3-b:5,4-c]dipyridin-2-yl)picolinamide (0.048 g, Yield 59%).

$^1$H NMR (400 MHz, DMSO-d$_6$) δ 2.87 (d, J=4.8 Hz, 3H), 8.09 (d, J=8.2 Hz, 1H), 8.19 (t, J=6.2 Hz, 2H), 8.45 (d, J=5.2 Hz, 1H), 8.75 (dd, J=8.2, 2.4 Hz, 1H), 8.85-8.87 (m, 2H), 8.93 (s, 1H), 9.42 (s, 1H), 12.35 (s, 1H).

MS (ESI) m/e (M+1)$^+$: 305.10

Reaction Scheme for Examples 54-55:

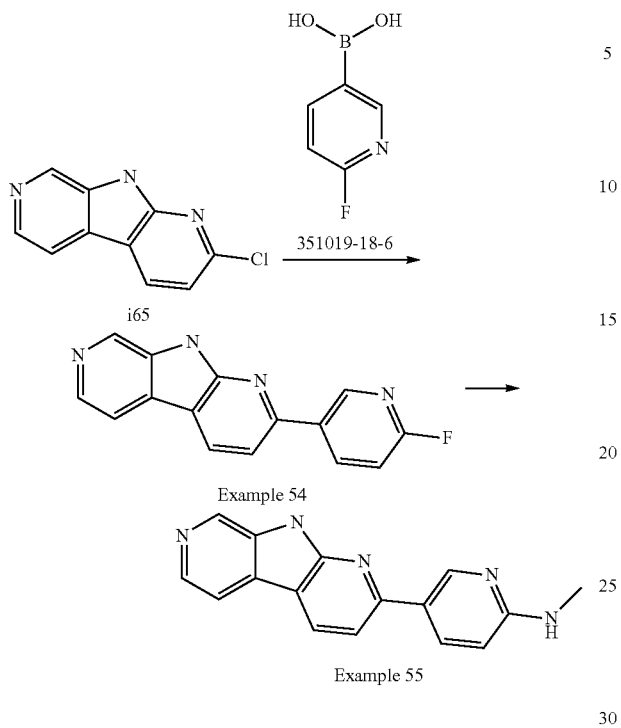

Example 54

Example 55

Example 54. 2-(6-fluoropyridin-3-yl)-9H-pyrrolo[2,3-b:5,4-c]dipyridine 2-chloro-9H-pyrrolo[2,3-b:5,4-c]dipyridine (i65) (0.4 g, 1.9 mmol) was reacted with (6-fluoropyridin-3-yl)boronic acid (0.33 g, 2.3 mmol) according to procedure A to afford 2-(6-fluoropyridin-3-yl)-9H-pyrrolo[2,3-b:5,4-c]dipyridine (0.105 g, Yield 20%).

$^1$H NMR (400 MHz, DMSO-$d_6$) δ 7.38 (dd, J=8.75, 2.92 Hz, 1H), 8.01 (d, J=8.08 Hz, 1H), 8.19 (d, J=5.39 Hz, 1H), 8.45 (d, J=5.39 Hz, 1H), 8.71-8.84 (m, 2H), 8.92 (s, 1H), 9.06 (d, J=2.24 Hz, 1H), 12.31 (s, 1H),

MS (ESI) m/e (M+1)$^+$: 265.1

Example 55. N-methyl-5-(9H-pyrrolo[2,3-b:5,4-c]dipyridin-2-yl)pyridin-2-amine 2-(6-fluoropyridin-3-yl)-9H-pyrrolo[2,3-b:5,4-c']dipyridine (example 54) (0.05 g, 0.18 mmol) was added to a methyl amine solution (4 mL) and the reaction mixture was heated at 120° C. for 16 h. The progress of the reaction was monitored by TLC. After completion, the reaction mixture was concentrated under reduced pressure to obtain a residue. The residue was washed with sodium bicarbonate solution and filtered. The obtained solid was washed with water, pentane and acetonitrile, dried to afford N-methyl-5-(9H-pyrrolo[2,3-b:5,4-c]dipyridin-2-yl)pyridin-2-amine (0.025 g, Yield 48%).

$^1$H NMR (400 MHz, DMSO-$d_6$) δ 2.82 (s, 3H), 7.36 (dd, J=8.6, 2.9 Hz, 1H), 7.50 (d, J=5.7 Hz, 1H), 8.01 (d, J=8.1 Hz, 1H), 8.51 (d, J=5.7 Hz, 1H), 8.60 (m, 1H), 8.74 (m, 2H), 8.42 (m, 2H), 12.40 (s, 1H),

MS (ESI) m/e (M+1)$^+$: 275.9

Example 56. 2-(4-methoxy-1H-pyrazol-1-yl)-9H-pyrrolo[2,3-b:5,4-c]dipyridine

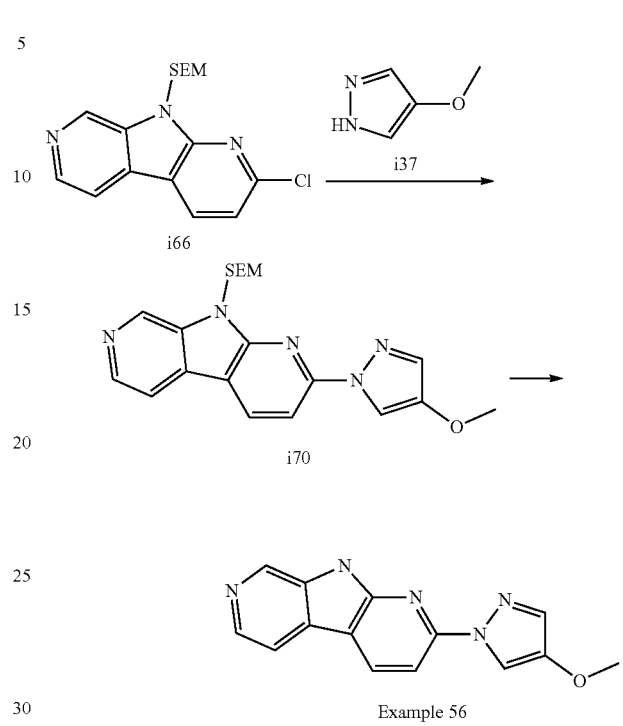

Example 56

2-(4-methoxy-1H-pyrazol-1-yl)-9-((2-(trimethylsilyl)ethoxy)methyl)-9H-pyrrolo[2,3-b:5,4-c]dipyridine (i70)

2-chloro-9-((2-(trimethylsilyl)ethoxy)methyl)-9H-pyrrolo[2,3-b:5,4-c]dipyridine (i66) (0.25 g, 0.75 mmol) was reacted with 4-methoxy-1H-pyrazole (i37) (0.088 g, 0.9 mmol) according to procedure J to afford 2-(4-methoxy-1H-pyrazol-1-yl)-9-((2-(trimethylsilyl)ethoxy)methyl)-9H-pyrrolo[2,3-b:5,4-c]dipyridine (i70) (0.11 g, Yield 37%).

$^1$H NMR (400 MHz, DMSO-$d_6$) δ −0.19 (s, 9H), 0.87 (t, J=7.7 Hz, 2H), 3.58 (t, J=7.7 Hz, 2H), 3.85 (s, 3H), 6.04 (s, 2H), 7.73 (d, J=8.0 Hz, 1H), 7.88 (d, J=8.5 Hz, 1H), 8.16 (d, J=7.5 Hz, 1H), 8.46-8.56 (m, 2H), 8.80 (d, J=8.4 Hz, 1H), 9.10 (s, 1H).

MS (ESI) m/e (M+1)$^+$: 396.00

2-(4-methoxy-1H-pyrazol-1-yl)-9H-pyrrolo[2,3-b:5,4-c]dipyridine (Example 56)

SEM deprotection of 2-(4-methoxy-1H-pyrazol-1-yl)-9-((2-(trimethylsilyl)ethoxy)methyl)-9H-pyrrolo[2,3-b:5,4-c]dipyridine (i70) (0.1 g, 0.25 mmol) was performed according to procedure F to afford 2-(4-methoxy-1H-pyrazol-1-yl)-9H-pyrrolo[2,3-b:5,4-c]dipyridine (0.04 g, Yield 59%).

$^1$H NMR (400 MHz, DMSO-$d_6$) δ 3.84 (s, 3H). 7.72 (s, 1H), 7.83 (d, J=8.5 Hz, 1H), 8.11 (d, J=5.2 Hz, 1H), 8.31 (s, 1H), 8.42 (d, J=5.3 Hz, 1H), 8.76 (d, J=8.4 Hz, 1H), 8.88 (s, 1H), 12.22 (s, 1H)

MS (ESI) m/e (M+1)$^+$: 266.00

Compounds of Formula I-C

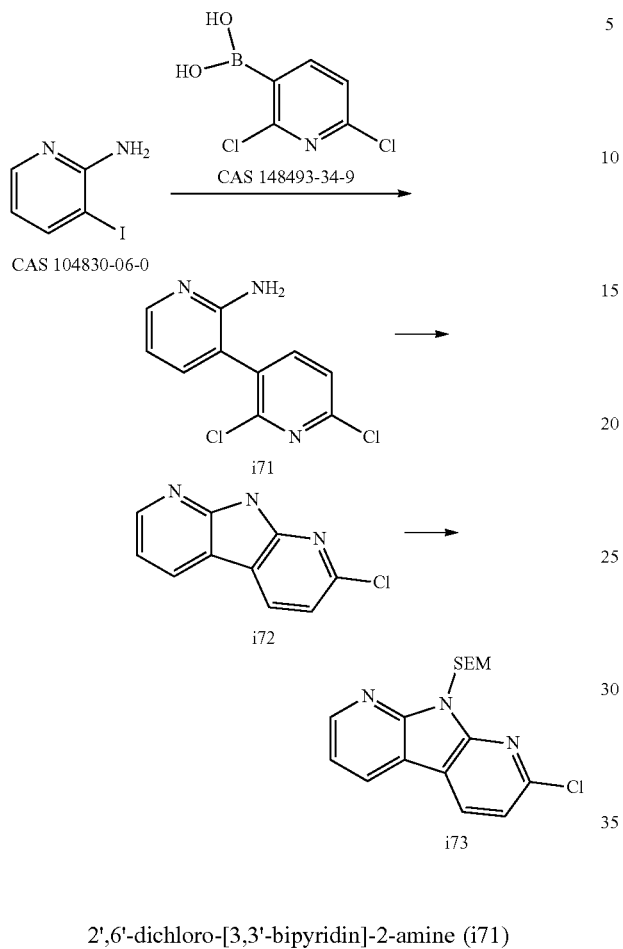

2',6'-dichloro-[3,3'-bipyridin]-2-amine (i71)

3-iodopyridin-2-amine (0.5 g, 2.27 mmol) was reacted with (2,6-dichloropyridin-3-yl)boronic acid (0.607 g, 3.1 mmol) according to procedure A to afford 2',6'-dichloro-[3,3'-bipyridin]-2-amine (i71) (0.227 g, Yield 22%).

$^1$H NMR (400 MHz, DMSO-$d_6$) δ 5.77 (brs, 2H), 6.62 (m, 1H), 7.28 (dd, J=7.3, 1.8 Hz, 1H), 7.43-7.67 (m, 1H), 7.83 (d, J=7.9 Hz, 1H), 8.02 (m, 1H).
MS (ESI) m/e (M+1)$^+$: 240

2-chloro-9H-pyrrolo[2,3-b:5,4-b]dipyridine (i72)

Cyclization of 2',6'-dichloro-[3,3'-bipyridin]-2-amine (i71) was performed according to procedure B to afford 2-chloro-9H-pyrrolo[2,3-b:5,4-b]dipyridine (i72) (0.5 g, Yield 65%).

$^1$H NMR (400 MHz, DMSO-$d_6$) δ 7.32-7.36 (m, 2H), 8.51 (m, 1H), 8.62-8.56 (m, 2H), 12.61 (s, 1H).
MS (ESI) m/e (M+1)$^+$: 204

2-chloro-9-((2-(trimethylsilyl)ethoxy)methyl)-9H-pyrrolo[2,3-b:5,4-b]dipyridine (i73)

SEM protection of 2-chloro-9H-pyrrolo[2,3-b:5,4-b] dipyridine (i72) was performed according to procedure E to afford 2-chloro-9-((2-(trimethylsilyl)ethoxy)methyl)-9H-pyrrolo[2,3-b:5,4-b]dipyridine (i73) (0.163 mg, Yield 43%).

$^1$H NMR (400 MHz, DMSO-$d_6$) δ −0.15 (s, 9H), 0.80-0.92 (m, 2H), 3.52-3.62 (m, 2H), 5.85 (s, 2H), 7.38-7.51 (m, 2H), 8.55-8.72 (m, 3H).
MS (ESI) m/e (M+1)$^+$: 334

Example 57. 2-(6-fluoropyridin-3-yl)-9H-pyrrolo[2,3-b:5,4-b]dipyridine

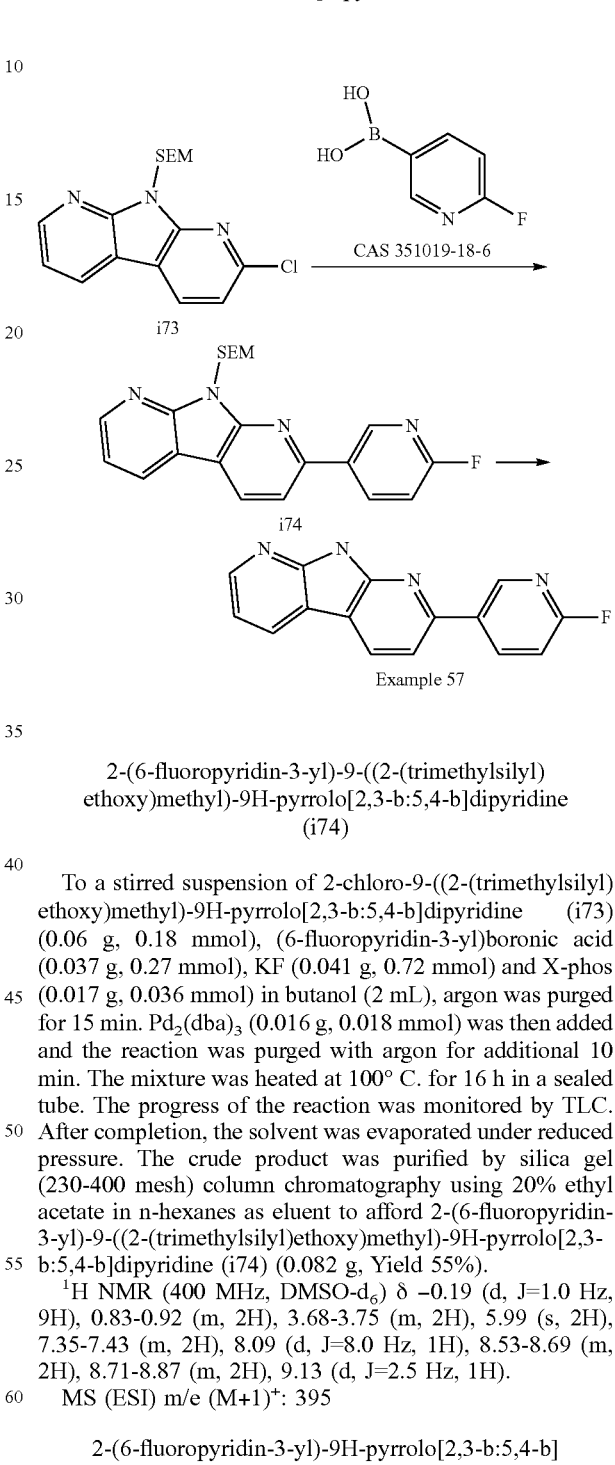

Example 57

2-(6-fluoropyridin-3-yl)-9-((2-(trimethylsilyl)ethoxy)methyl)-9H-pyrrolo[2,3-b:5,4-b]dipyridine (i74)

To a stirred suspension of 2-chloro-9-((2-(trimethylsilyl)ethoxy)methyl)-9H-pyrrolo[2,3-b:5,4-b]dipyridine (i73) (0.06 g, 0.18 mmol), (6-fluoropyridin-3-yl)boronic acid (0.037 g, 0.27 mmol), KF (0.041 g, 0.72 mmol) and X-phos (0.017 g, 0.036 mmol) in butanol (2 mL), argon was purged for 15 min. Pd$_2$(dba)$_3$ (0.016 g, 0.018 mmol) was then added and the reaction was purged with argon for additional 10 min. The mixture was heated at 100° C. for 16 h in a sealed tube. The progress of the reaction was monitored by TLC. After completion, the solvent was evaporated under reduced pressure. The crude product was purified by silica gel (230-400 mesh) column chromatography using 20% ethyl acetate in n-hexanes as eluent to afford 2-(6-fluoropyridin-3-yl)-9-((2-(trimethylsilyl)ethoxy)methyl)-9H-pyrrolo[2,3-b:5,4-b]dipyridine (i74) (0.082 g, Yield 55%).

$^1$H NMR (400 MHz, DMSO-$d_6$) δ −0.19 (d, J=1.0 Hz, 9H), 0.83-0.92 (m, 2H), 3.68-3.75 (m, 2H), 5.99 (s, 2H), 7.35-7.43 (m, 2H), 8.09 (d, J=8.0 Hz, 1H), 8.53-8.69 (m, 2H), 8.71-8.87 (m, 2H), 9.13 (d, J=2.5 Hz, 1H).
MS (ESI) m/e (M+1)$^+$: 395

2-(6-fluoropyridin-3-yl)-9H-pyrrolo[2,3-b:5,4-b]dipyridine (Example 57)

SEM deprotection of 2-(6-fluoropyridin-3-yl)-9-((2-(trimethylsilyl)ethoxy)methyl)-9H-pyrrolo[2,3-b:5,4-b]dipyridine (i74) (0.04 g, 0.12 mmol) was performed according to procedure F to afford 2-(6-fluoropyridin-3-yl)-9H-pyrrolo[2,3-b:5,4-b]dipyridine (0.026 g, 88%).

$^1$H NMR (400 MHz, DMSO-d$_6$) δ 7.29-7.37 (m, 2H), 7.97 (dd, J=8.2, 1.2 Hz, 1H), 8.50 (dd, J=5.8, 1.6 Hz, 1H), 8.59 (dd, J=7.9, 1.7 Hz, 1H), 8.65-8.78 (m, 2H), 9.03 (d, J=2.6 Hz, 1H), 12.50 (s, 1H).

MS (ESI) m/e (M+1)$^+$: 265

Example 58. 2-(4-(3-fluoropropyl)piperidin-1-yl)-9H-pyrrolo[2,3-b:5,4-b]dipyridine nol (40 mL), Pd(OH)$_2$ (0.236 g) was added and the reaction was heated under hydrogen pressure at 50° C. for 12 h. The progress of the reaction was monitored by TLC. After completion, reaction was filtered through celite bed and filtrate was evaporated under reduced pressure to afford 3-(piperidin-4-yl)propan-1-ol (i77) (2.075 g, crude).

$^1$H NMR (400 MHz, DMSO-d$_6$) δ 0.87-1.46 (m, 8H), 1.55 (m, 2H), 2.34-2.44 (m, 2H), 2.83-2.93 (m, 2H), 3.22 (s, 1H), 3.31-3.40 (m, 2H).

MS (ESI) m/e (M+1)$^+$: not recorded

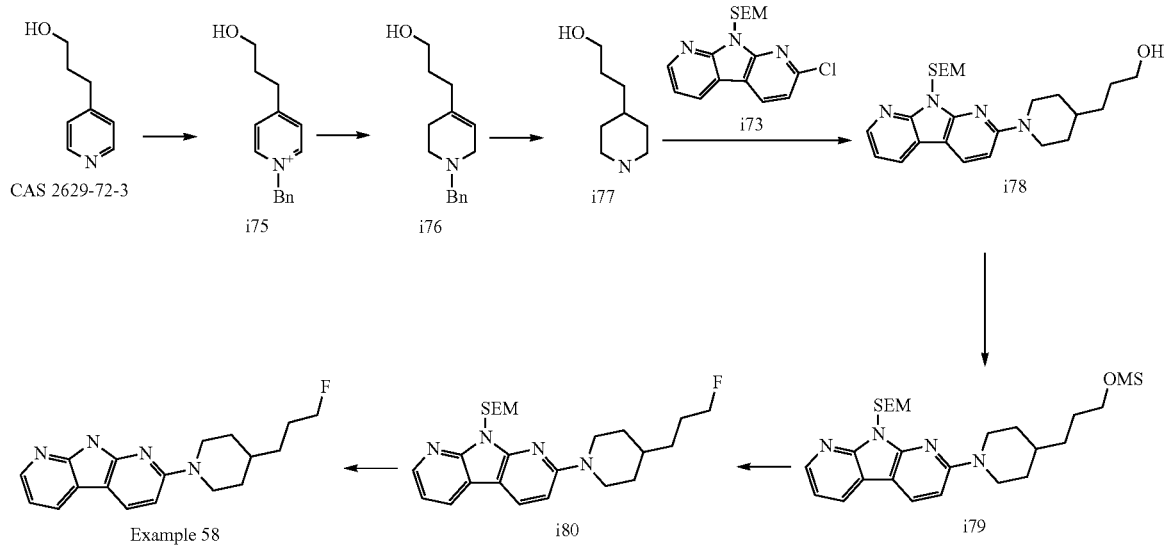

1-benzyl-4-(3-hydroxypropyl)pyridin-1-ium bromide (i75)

To a stirred solution of 3-(pyridin-4-yl) propan-1-ol (2 g, 14.59 mmol) in acetone (20 mL), benzyl bromide (1.9 mL, 16 mmol) was added and the reaction was heated at 65° C. for 1 h. The progress of the reaction was monitored by TLC. After completion of the reaction, the solvent was evaporated under reduced pressure to afford 1-benzyl-4-(3-hydroxypropyl)pyridin-1-ium bromide (i75) (5.1 g, crude) which was used as such for next step without further purification and analysis.

3-(1-benzyl-1,2,3,6-tetrahydropyridin-4-yl)propan-1-ol (i76)

To a stirred solution of 1-benzyl-4-(3-hydroxypropyl) pyridin-1-ium bromide (i75) (5.1 g, 22.36 mmol) in methanol (29 mL) and water (7.2 mL), NaBH$_4$ (1.69 g, 44.72 mmol) was added at 0° C. and the reaction was heated at 90° C. for 2 h. The progress of the reaction was monitored by TLC. After completion of the reaction, the solvent was evaporated under reduced pressure. The residue was diluted with ethyl acetate and washed with saturated sodium bicarbonate solution. The organic layer was separated, dried over anhydrous sodium sulphate and concentrated under reduced pressure to afford 3-(1-benzyl-1,2,3,6-tetrahydropyridin-4-yl)propan-1-ol (i76) (3.1 g) which was used as such for next step without further purification and analysis.

3-(piperidin-4-yl)propan-1-ol (i77)

To a stirred solution of 3-(1-benzyl-1,2,3,6-tetrahydropyridin-4-yl)propan-1-ol (i76) (3.1 g, 13.41 mmol) in etha- 3-(1-(9-((2-(trimethylsilyl)ethoxy)methyl)-9H-pyrrolo[2,3-b:5,4-b]dipyridin-2-yl)piperidin-4-yl)propan-1-ol (i78)

To a stirred solution of 3-(piperidin-4-yl)propan-1-ol (i77) (0.163 g, 1.13 mmol) and 2-chloro-9-((2-(trimethylsilyl)ethoxy)methyl)-9H-pyrrolo[2,3-b:5,4-b]dipyridine (i73) (0.186 g, 0.56 mmol) in DMF (4 mL), K$_2$CO$_3$ (0.235 g, 1.68 mmol) was added and the reaction was heated at 130° C. for 64 h in a sealed tube. The progress of the reaction was monitored by TLC. After completion, the mixture was quenched with ice and extracted with ethyl acetate. The organic layer was separated, washed with cold water, dried over anhydrous sodium sulphate and concentrated under reduced pressure. The crude product was purified by silica gel (100:200 mesh) column chromatography using 5% methanol in dichloromethane as eluent to afford 3-(1-(9-((2-(trimethylsilyl)ethoxy)methyl)-9H-pyrrolo[2,3-b:5,4-b]dipyridin-2-yl)piperidin-4-yl)propan-1-ol (i78) (0.155 g, Yield 84%).

$^1$H NMR (400 MHz, DMSO-d$_6$) δ −0.13 (s, 9H), 0.84 (m, 2H), 1.19 (m, 3H), 1.40-1.55 (m, 3H), 1.77 (m, 2H), 2.89 (m, 2H), 3.39 (m, 2H), 3.65 (m, 2H), 4.36 (m, 1H), 4.49 (m, 2H), 5.75 (s, 2H), 6.81 (d, J=8.8 Hz, 1H), 7.21 (m, 1H), 8.19-8.32 (m, 3H).

MS (ESI) m/e (M+1)$^+$:441.00

3-(1-(9-((2-(trimethylsilyl)ethoxy)methyl)-9H-pyrrolo[2,3-b:5,4-b]dipyridin-2-yl)piperidin-4-yl)propyl methanesulfonate (i79)

To a stirred solution of 3-(1-(9-((2-(trimethylsilyl)ethoxy)methyl)-9H-pyrrolo[2,3-b:5,4-b]dipyridin-2-yl)piperidin-4- yl)propan-1-ol (i78) (0.31 g, 0.7 mmol) in DCM (8 mL), TEA (0.187 mL, 1.4 mmol) was added at 0° C. followed by mesyl chloride (0.06 mL, 0.77 mmol) at the same temperature. The reaction was stirred at 0° C. for 1 h. TLC showed some starting material intact hence extra mesyl chloride (0.027 mL. 0.35 mmol) was added at 0° C. and stirred at the same temperature for 3 h. The progress of the reaction was monitored by TLC. After completion, the mixture was diluted with water and extracted with ethyl acetate. The organic layer was separated, dried over anhydrous sodium sulphate and concentrated under reduced pressure to afford 3-(1-(9-((2-(trimethylsilyl)ethoxy)methyl)-9H-pyrrolo[2,3-b:5,4-b]dipyridin-2-yl)piperidin-4-yl)propyl methanesulfonate (i79) (0.408 g, crude).

$^1$H NMR (400 MHz, DMSO-d$_6$) δ -0.13 (s, 9H), 0.80-0.89 (m, 2H), 1.11-1.37 (m, 5H), 1.66-1.82 (m, 4H), 2.32 (s, 3H), 2.86-2.97 (m, 2H), 3.61-3.70 (m, 2H), 4.20 (m, 2H), 4.50 (m, 2H), 5.76 (s, 2H), 6.84 (d, J=8.9 Hz, 1H), 7.23 (dd, J=7.6, 4.9 Hz, 1H), 8.20-8.33 (m, 3H).

2-(4-(3-fluoropropyl)piperidin-1-yl)-9-((2-(trimethylsilyl)ethoxy)methyl)-9H-pyrrolo[2,3-b:5,4-b]dipyridine (i80)

To a stirred solution of 3-(1-(9-((2-(trimethylsilyl)ethoxy)methyl)-9H-pyrrolo[2,3-b:5,4-b]dipyridin-2-yl)piperidin-4-yl)propyl methanesulfonate (i79) (0.2 g, 0.38 mmol) in t-butanol (5 mL), cesium fluoride (0.175 g, 1.1 mmol) was added and heated at 80° C. for 36 h. The progress of the reaction was monitored by TLC. After completion, the mixture was diluted with water and extracted with ethyl acetate. The organic layer was separated, dried over anhydrous sodium sulphate and concentrated under reduced pressure. The crude product was purified by silica gel (100-200 mesh) column chromatography using 10% ethyl acetate in n-hexane as eluent to afford 2-(4-(3-fluoropropyl)piperidin-1-yl)-9-((2-(trimethylsilyl)ethoxy)methyl)-9H-pyrrolo[2,3-b:5,4-b]dipyridine (i80) (0.088 g, Yield 52%).

$^1$H NMR (400 MHz, DMSO-d$_6$) δ -0.13 (s, 9H), 0.84 (m, 2H), 1.09-1.36 (m, 5H), 1.60-1.82 (m, 4H), 2.91 (m, 4H), 3.61-3.70 (m, 2H), 4.46-4.54 (m, 2H), 5.75 (s, 2H), 6.82 (d, J=8.8 Hz, 1H), 7.21 (m, 1H), 8.19-8.32 (m, 3H).

MS (ESI) m/e (M+1)$^+$: 443.20

2-(4-(3-fluoropropyl)piperidin-1-yl)-9H-pyrrolo[2,3-b:5,4-b]dipyridine (Example 58)

SEM deprotection of 2-(4-(3-fluoropropyhpiperidin-1-yl)-9-((2-(trimethylsilyl)ethoxy)methyl)-9H-pyrrolo[2,3-b:5,4-b]dipyridine (i80) (0.17 g, 0.39 mmol) was performed according to procedure F to afford 2-(4-(3-fluoropropyhpiperidin-1-yl)-9H-pyrrolo[2,3-b:5,4-b]dipyridine (0.088 g, Yield 73%).

$^1$H NMR (400 MHz, DMSO-d$_6$) δ 1.07-1.36 (m, 4H), 1.48-1.82 (m, 5H), 2.87 (m, 2H), 4.34-4.54 (m, 4H), 6.74 (m, 1H), 7.11 (m, 1H), 8.14-8.25 (m, 3H), 11.74 (s, 1H).

MS (ESI) m/e (M+1)$^+$: 313.25

Compounds of Formula I-D

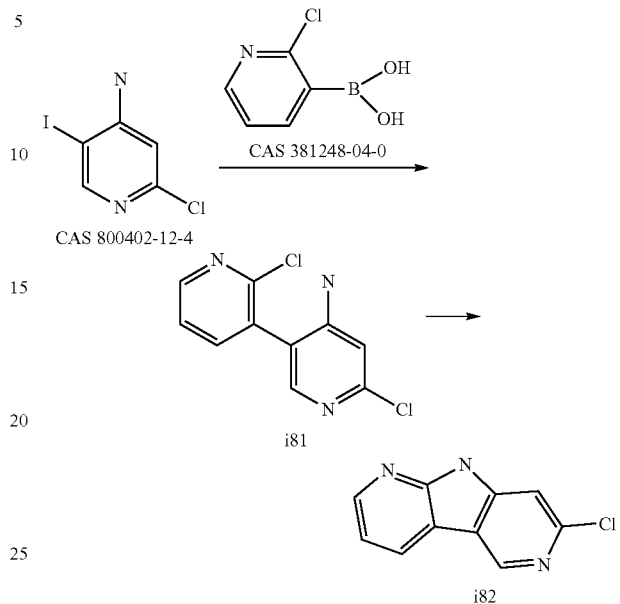

2',6-dichloro-[3,3'-bipyridin]-4-amine (i81)

2-chloro-5-iodopyridin-4-amine (1 g, 3.9 mmol) was reacted with (2-chloropyridin-3-yl)boronic acid (0.804 g, 5.1 mmol) according to procedure A to afford 2',6-dichloro-[3,3'-bipyridin]-4-amine (i81) (0.76, Yield 81%).

$^1$H NMR (400 MHz, DMSO-d$_6$) δ 6.24 (s, 2H), 6.66 (s, 1H), 7.54-7.60 (m, 1H), 7.71 (s, 1H), 7.80 (d, J=7.6 Hz, 1H), 8.47 (d, J=4.9 Hz, 1H).

MS (ESI) m/e (M+1)$^+$: 240.00

7-chloro-9H-pyrrolo[2,3-b:4,5-c']dipyridine (i82)

Cyclization of 2',6-dichloro-[3,3'-bipyridin]-4-amine (i81) was performed according to procedure B to afford 7-chloro-9H-pyrrolo[2,3-b:4,5-c']dipyridine (i82) (1.4 g, Yield 75%).

$^1$H NMR (400 MHz, DMSO-d$_6$) δ 7.35 (dd, J=7.8, 4.9 Hz, 1H), 7.47-7.69 (m, 1H), 8.52 (m, 1H), 8.64 (dd, J=7.8, 1.7 Hz, 1H), 9.20 (s, 1H), 12.43 (s, 1H).

MS (ESI) m/e (M+1)$^+$: 204.00

Generic Reaction Scheme for Examples 59-61:

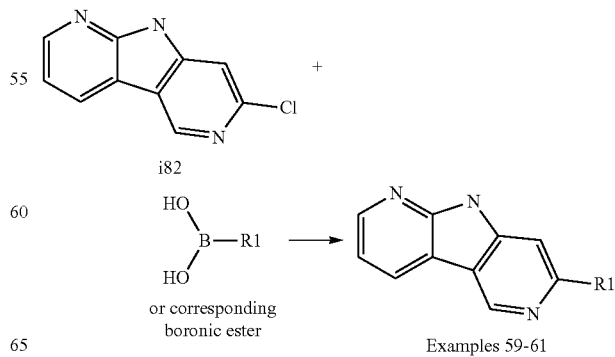

Examples 59-61

Example 59. 7-(6-fluoropyridin-3-yl)-9H-pyrrolo[2,3-b:4,5-c']dipyridine 7-chloro-9H-pyrrolo[2,3-b:4,5-c']dipyridine (i82) (0.15 g, 0.738 mmol) was reacted with (6-fluoropyridin-3-yl)boronic acid (0.115 g, 1.108 mmol) according to procedure C to afford 7-(6-fluoropyridin-3-yl)-9H-pyrrolo[2,3-b:4,5-c']dipyridine (0.048 g, Yield 25%).

$^1$H NMR (400 MHz, DMSO-d$_6$) δ 7.28-7.39 (m, 2H), 8.03 (s, 1H), 8.52 (d, J=5.4 Hz, 1H), 8.63-8.78 (m, 2H), 9.04 (d, J=5.4 Hz, 1H), 9.48 (s, 1H), 12.46 (s, 1H).

MS (ESI) m/e (M+1)$^+$: 265

Example 60. N-methyl-5-(9H-pyrrolo[2,3-b:4,5-c']dipyridin-7-yl)picolinamide 7-chloro-9H-pyrrolo[2,3-b:4,5-c']dipyridine (i82) (1 g, 3.9 mmol) was reacted with (2-chloropyridin-3-yl)boronic acid (0.804 g, 5.1 mmol) according to procedure C to afford N-methyl-5-(9H-pyrrolo[2,3-b:4,5-c']dipyridin-7-yl)picolinamide (0.76 g, Yield 81%).

$^1$H NMR (400 MHz, DMSO-d$_6$) δ 6.24 (brs, 2H) 6.66 (s, 1H) 7.48-7.66 (m, 4H) 7.69 (s, 1H) 7.76-7.85 (m, 1H) 8.43-8.53 (m, 1H) (3H's merged in solvent peak)

MS (ESI) m/e (M+1)$^+$: 240.00

Example 61. 7-(1-methyl-1H-pyrazol-4-yl)-9H-pyrrolo[2,3-b:4,5-c']dipyridine 7-chloro-9H-pyrrolo[2,3-b:4,5-c']dipyridine (i82) was reacted with 1-methyl-4-(4,4,5,5-tetramethyl-1,3,2-dioxaborolan-2-yl)-1H-pyrazole (0.229 g, 1.108 mmol) according to procedure D to afford 7-(1-methyl-1H-pyrazol-4-yl)-9H-pyrrolo[2,3-b:4,5-c']dipyridine (0.082 g, Yield 45%).

$^1$H NMR (400 MHz, DMSO-d$_6$) δ 3.90 (s, 3H) 7.28 (dd, J=7.63, 4.86 Hz, 1H) 7.62 (s, 1H) 8.06 (s, 1H) 8.35 (s, 1H) 8.44 (dd, J=5.09, 1.39 Hz, 1H) 8.55 (d, J=7.40 Hz, 1H) 9.28 (s, 1H) 12.19 (s, 1H)

MS (ESI) m/e (M+1)$^+$: 250.00

Preparation of the [$^3$H]-Radiolabelled Examples 62-65:

Example 62

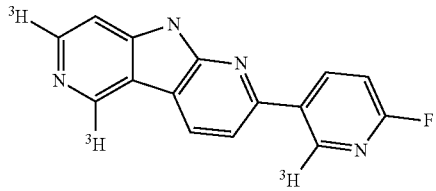

Example 63

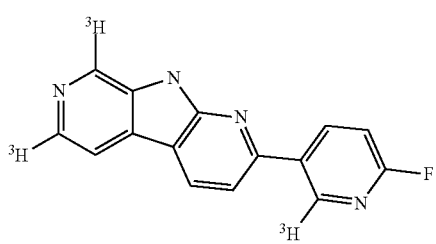

Example 64

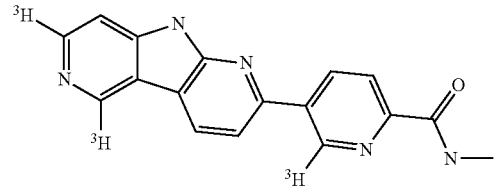

Example 65

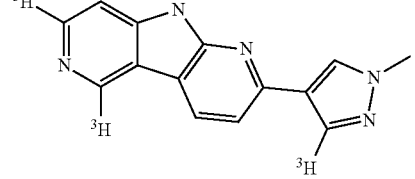

Example 62. 2-[6-fluoro(2-$^3$H)pyridin-3-yl](5,7-$^3$H$_2$)-9H-pyrrolo[2,3-b:4,5-c']dipyridine 2-(6-fluoropyridin-3-yl)-9H-pyrrolo[2,3-b:4,5-c']dipyridine obtained according to procedure C was reacted with tritium gas according to procedure K to afford 2-[6-fluoro(2-$^3$H)pyridin-3-yl](5,7-$^3$H$_2$)-9H-pyrrolo[2,3-b:4,5-c']dipyridine (RCP>98%; SA: 30.3 Ci/mmol).

Example 63. 2-[6-fluoro(2-$^3$H)pyridin-3-yl](6,8-$^3$H$_2$)-9H-pyrrolo[2,3-b:5,4-c]dipyridine 2-(6-fluoropyridin-3-yl)-9H-pyrrolo[2,3-b:5,4-c']dipyridine (example 54) was reacted with tritium gas according to procedure K to afford 2-[6-fluoro(2-$^3$H)pyridin-3-yl](6,8-$^3$H$_2$)-9H-pyrrolo[2,3-b:5,4-c']dipyridine (RCP>98%; SA: 25.0 Ci/mmol).

Example 64. N-methyl-5-[(5,7-$^3$H$_2$)-9H-pyrrolo[2,3-b:4,5-c']dipyridin-2-yl](6-$^3$H)pyridine-2-carboxamide N-methyl-5-(9H-pyrrolo[2,3-b:4,5-c']dipyridin-2-yl)pyridine-2-carboxamide (example 11) was reacted with tritium gas according to procedure K to afford N-methyl-5-[(5,7-$^3$H$_2$)-9H-pyrrolo[2,3-b:4,5-c']dipyridin-2-yl](6-$^3$H)pyridine-2-carboxamide (RCP>98%; SA: 20.2 Ci/mmol).

Example 65. 2-[1-methyl(3-$^3$H)-1H-pyrazol-4-yl](5,7-$^3$H$_2$)-9H-pyrrolo[2,3-b:4,5-c']dipyridine 2-(1-methyl-1H-pyrazol-4-yl)-9H-pyrrolo[2,3-b:4,5-c']dipyridine (example 4) was reacted with tritium gas according to procedure K to afford 2-[1-methyl(3-$^3$H)-1H-pyrazol-4-yl](5,7-$^3$H$_2$)-9H-pyrrolo[2,3-b:4,5-c']dipyridine (RCP>98%; SA: 17.8 Ci/mmol).

Biological Results of Compounds

Materials and Methods

K18/K19 Recombinant Tau Fibrils Preparation

His tagged K18 Tau (4 repeats MTBR) and His tagged K19 Tau (3 repeats MTBR) were cloned into a pET Expression vector. Expression vectors were transformed into *E. coli* strain BL21 (DE3), cultured and induced with IPTG. Harvested cells were lysed using mechanical lysis before purification with Ni-NTA superflow (Qiagen, Venlo, Netherlands).

His-Tag from K18 Tau was removed by cleavage with TEV protease. Ni-NTA was used to remove cleaved tag and TEV. K18 and K19 His-tagged Tau buffer was exchanged into PBS, pH 7.4, flash frozen and stored at −80° C.

Tau K18 and Tau K19-His were thawed and mixed (both at ~300 µM). Mixture was filtered through a 0.22 µm membrane. Sample was shaken in thermomixer (Eppendorf, Rotselaer, Belgium) at 750 rpm, 37° C. for 96 hours. Fibril mixture was recovered, aliquotted and stored at 4° C. or −80° C.

Radioligand In Vitro Binding Assays on Recombinant and Native Tau Protein

[$^3$H]compound binding to Tau protein methods were adapted from Nobuyuki et al (2013). Biological samples as described above (0.2-50 µg proteins per assays) were incubated for 60 min at 25° C. with [$^3$H]compound in 0.2 ml of PBS containing 0.1% bovine serum albumin (Sigma-Aldrich, Diegem, Belgium). At the end of the incubation period, the protein-bound radioligand was recovered by reduced pressure filtration through GF/F glass fiber filters (GE Healthcare, Diegem, Belgium) pre-soaked in 0.1% polyethyleneimine (Sigma-Aldrich, Diegem, Belgium). Filters were washed with at least 4 times the assay volume of ice-cold PBS (pH 7.4). The entire filtration step did not exceed 10 sec The filters were dried and the radioactivity determined by liquid scintillation. Saturation binding assays were carried out using increasing concentrations of [$^3$H] compound (0.5 to 100 nM). Competition binding experiments were carried out at constant [$^3$H]compounds concentration (15 nM) and increasing concentrations of unlabeled competing compounds (10 concentration data point from 10 µM to 0.1 nM). $pIC_{50}$ were corrected to pKi according to Cheng and Prusoff (1973). In all experiments, the NSB was defined as the residual binding of [$^3$H]compound observed in the presence of 10 µM T807.

Selectivity Profile

Compound selectivity for Tau protein was assessed as compared to a broad panel of receptors, enzymes and ion channels. Selectivity profiling of 10 µM compounds against a panel of 81 targets (n=1 with data in duplicate) was performed. Compounds affinity for rat MAO-A enzyme was assessed in rat cerebral cortex by competition experiment for 10 nM [$^3$H]Ro 41-1049 and increasing concentrations of test compounds. Compounds affinity for human MAO-A enzyme (1 µg/assay, Sigma-Aldrich, Diegem, Belgium) was assessed by saturation binding experiment performed as described above with [3H]compounds.

Binding Data Analysis

Binding data analysis was performed by computerized curve fitting (Graphpad Prism® software, version 4.0, San Diego, CA) according to equations describing specific saturation binding in one or two sites, and competitive binding model.

Rat Brain Free Fraction (Fu) Measurement

The Brain free faction was carried out in duplicate at a single concentration of 1 µM after 4 h of equilibrium dialysis.

Male Sprague-Dawley Rat (Harlan, Bresso, Italy) brain homogenate were prepared in PBS, pH 7.4 at 25% w/vy using a Precellys 24-dual tissue homogenizer (BERTIN technologies, Montigny-le-Bretonneux, France).

200 µL brain homogenate was incubated with 1 µM test compound or reference compound (propranolol, Sigma, St Louis, United states) (1% DMSO final) for at least 30 min at 37° C. under agitation before loading in a retentate chamber of a RED Device insert (8K MWCO, Thermo Scientific™ Pierce™ RED Device, Waltham, United states). 350 µL PBS pH 7.4 was loaded in the other chamber of the insert. The Red device reusable base counting insert containing insert with both samples and buffer was sealed and incubated during 4 h at 37° C., 300 rpm, on an orbital shaker.

At the end of the incubation, all brain samples were diluted 1:1 with PBS and PBS samples were diluted 1:1 with control brain homogenate. All samples were then diluted 1:3 with an internal standard (dextromethorphan 10 ng/mL in acetonitrile, Sigma, St Louis, United states), mixed and centrifuged 5 min at 3000 rpm at 4° C. Supernatant was diluted 1:2 with 0.1% formic acid in water (Biosolve, Dieuze, France) before analysis by LC/MS/MS. The LC system used was an Agilent 1290 (Agilent, Santa Clara, United states) coupled with a API5000 mass spectrometer (ABSciex, Framingham, United states). The software was analyst 1.5.2. (Agilent, Santa Clara, United states), the analytical column was an Aquity UPLC HSS T3 (30×2.1 mm, 1.8 µm, Waters, Saint-Quentin, France) operated at 40° C. Analysis were performed in the gradient described below. Gradient Used for LC MS/MS:

| Total Time (min) | Flow Rate (µl/min) | B (%) |
|---|---|---|
| 0.00 | 1000 | 5 |
| 0.50 | 1000 | 5 |
| 1.96 | 1000 | 70 |
| 1.97 | 1000 | 95 |
| 2.50 | 1000 | 95 |
| 2.51 | 1000 | 5 |
| 3.00 | 1000 | 5 |

Where eluent A was 0.1% formic acid in $H_2O$ (Biosolve, Dieuze, France), eluent B was 0.1% formic acid in acetonitrile (Biosolve, Dieuze, France).

The flow was directly injected into the electrospray source.

The Fu brain (%) was calculated using the following equation:

$$Fu\ brain\ (\%) = (1/(1+((1/((fu\ homogenate)-1)\times D)))\times 100$$

Where Fu homogenate=peak area ratio buffer/peak area ratio brain and D=dilution factor of the homogenate.

TABLE 1

BINDING RESULTS
Tau binding and rat brain free fraction

| EXAMPLE # | IUPAC NAME | pIC50 TAU_K18K19 (−log M) | Fu Rat Brain (%) |
|---|---|---|---|
| 1 | 2-(pyridin-4-yl)-9H-pyrrolo[2,3-b:4,5-c']dipyridine | 7.0 | |
| 2 | 2-(2-methoxypyridin-4-yl)-9H-pyrrolo[2,3-b:4,5-c']dipyridine | 7.7 | 0.9 |
| 3 | 2-(pyridin-3-yl)-9H-pyrrolo[2,3-b:4,5-c']dipyridine | 7.0 | |
| 4 | 2-(1-methyl-1H-pyrazol-4-yl)-9H-pyrrolo[2,3-b:4,5-c']dipyridine | 7.4 | 7.5 |
| 5 | 2-(6-methoxypyridin-3-yl)-9H-pyrrolo[2,3-b:4,5-c']dipyridine | 7.8 | 0.6 |
| 6 | 5-(9H-pyrrolo[2,3-b:4,5-c']dipyridin-2-yl)pyridin-2(1H)-one | 7.2 | 9.8 |
| 7 | 2-(5-fluoro-6-methoxypyridin-3-yl)-9H-pyrrolo[2,3-b:4,5-c']dipyridine | 7.6 | 0.5 |
| 8 | 2-(furan-3-yl)-9H-pyrrolo[2,3-b:4,5-c']dipyridine | 7.5 | |
| 9 | 2-(1H-pyrazol-4-yl)-9H-pyrrolo[2,3-b:4,5-c']dipyridine | 7.6 | 3.6 |
| 10 | 2-[2-(morpholin-4-yl)pyrimidin-5-yl]-9H-pyrrolo[2,3-b:4,5-c']dipyridine | 7.8 | 1.1 |
| 11 | N-methyl-5-(9H-pyrrolo[2,3-b:4,5-c']dipyridin-2-yl)pyridine-2-carboxamide | 8.0 | 2.8 |
| 12 | 3-fluoro-5-(9H-pyrrolo[2,3-b:4,5-c']dipyridin-2-yl)pyridin-2-amine | 7.8 | 0.5 |
| 13 | 2-[4-(pyrimidin-2-yl)piperazin-1-yl]-9H-pyrrolo[2,3-b:4,5-c']dipyridine | 7.0 | 1.1 |
| 14 | 2-[4-(pyridin-4-yl)piperazin-1-yl]-9H-pyrrolo[2,3-b:4,5-c']dipyridine | 7.1 | 1.9 |
| 15 | 2-(1H-pyrazol-3-yl)-9H-pyrrolo[2,3-b:4,5-c']dipyridine | 7.5 | 5.6 |
| 16 | 4-(9H-pyrrolo[2,3-b:4,5-c']dipyridin-2-yl)pyridin-2-amine | 7.4 | |
| 17 | 4-(9H-pyrrolo[2,3-b:4,5-c']dipyridin-2-yl)pyridin-2(1H)-one | 7.4 | |
| 18 | 2-(5-fluoropyridin-2-yl)-9H-pyrrolo[2,3-b:4,5-c']dipyridine | 7.0 | |
| 19 | 2-fluoro-5-(9H-pyrrolo[2,3-b:4,5-c']dipyridin-2-yl)pyridin-3-amine | 7.1 | |
| 20 | N-methyl-5-(9H-pyrrolo[2,3-b:4,5-c']dipyridin-2-yl)pyrimidin-2-amine | 7.5 | |
| 21 | 2-[6-(morpholin-4-yl)pyridin-3-yl]-9H-pyrrolo[2,3-b:4,5-c']dipyridine | 7.6 | 0.5 |
| 22 | N-(2-methoxyethyl)-5-(9H-pyrrolo[2,3-b:4,5-c']dipyridin-2-yl)pyrimidin-2-amine | 7.5 | |
| 23 | 2-[2-(piperazin-1-yl)pyrimidin-5-yl]-9H-pyrrolo[2,3-b:4,5-c']dipyridine | 7.4 | |
| 24 | 2-(5-methyl-1H-pyrazol-3-yl)-9H-pyrrolo[2,3-b:4,5-c']dipyridine | 7.6 | 2.0 |
| 25 | 2-[1-(2-fluoroethyl)-1H-pyrazol-4-yl]-9H-pyrrolo[2,3-b:4,5-c']dipyridine | 7.3 | 8.7 |
| 26 | N-methyl-2-[4-(9H-pyrrolo[2,3-b:4,5-c']dipyridin-2-yl)-1H-pyrazol-1-yl]acetamide | 7.0 | |
| 27 | N-methyl-6-(9H-pyrrolo[2,3-b:4,5-c']dipyridin-2-yl)pyridine-3-carboxamide | 7.6 | |
| 28 | N,N-dimethyl-5-(9H-pyrrolo[2,3-b:4,5-c']dipyridin-2-yl)pyridine-2-carboxamide | 7.4 | |
| 29 | N-(2-fluoroethyl)-5-(9H-pyrrolo[2,3-b:4,5-c']dipyridin-2-yl)pyridine-2-carboxamide | 7.4 | |
| 30 | N-(2-methoxyethyl)-5-(9H-pyrrolo[2,3-b:4,5-c']dipyridin-2-yl)pyridine-2-carboxamide | 7.4 | |
| 31 | 2-(4-methoxy-1H-pyrazol-1-yl)-9H-pyrrolo[2,3-b:4,5-c']dipyridine | 7.4 | 0.7 |
| 32 | 2-[2-(morpholin-4-yl)-1,3-thiazol-5-yl]-9H-pyrrolo[2,3-b:4,5-c']dipyridine | 7.6 | 0.5 |
| 33 | 1-{4-[5-(9H-pyrrolo[2,3-b:4,5-c']dipyridin-2-yl)pyrimidin-2-yl]piperazin-1-yl}ethanone | 7.1 | |
| 34 | 6-fluoro-N-(9H-pyrrolo[2,3-b:4,5-c']dipyridin-2-yl)pyridine-3-carboxamide | 7.2 | |
| 35 | 6-(methylamino)-N-(9H-pyrrolo[2,3-b:4,5-c']dipyridin-2-yl)pyridine-3-carboxamide | 7.2 | 0.5 |
| 36 | 2-(6-fluoropyridin-3-yl)-7-methoxy-9H-pyrrolo[2,3-b:4,5-c']dipyridine | 7.5 | 0.5 |

TABLE 1-continued

BINDING RESULTS
Tau binding and rat brain free fraction

| EXAMPLE # | IUPAC NAME | pIC50 TAU_K18K19 (−log M) | Fu Rat Brain (%) |
|---|---|---|---|
| 37 | 5-(7-methoxy-9H-pyrrolo[2,3-b:4,5-c']dipyridin-2-yl)-N-methylpyridine-2-carboxamide | 8.0 | |
| 38 | 7-methoxy-2-(1-methyl-1H-pyrazol-4-yl)-9H-pyrrolo[2,3-b:4,5-c']dipyridine | 7.4 | |
| 39 | 7-methoxy-2-[2-(morpholin-4-yl)pyrimidin-5-yl]-9H-pyrrolo[2,3-b:4,5-c']dipyridine | 7.5 | |
| 40 | 6-(7-methoxy-9H-pyrrolo[2,3-b:4,5-c']dipyridin-2-yl)-N-methylpyridine-3-carboxamide | 7.4 | |
| 41 | 5-(7-methoxy-9H-pyrrolo[2,3-b:4,5-c']dipyridin-2-yl)pyrimidine-2-carbonitrile | 7.7 | |
| 42 | 2-(6-fluoropyridin-3-yl)-N,N-dimethyl-9H-pyrrolo[2,3-b:4,5-c']dipyridin-7-amine | 7.5 | |
| 43 | 5-[7-(dimethylamino)-9H-pyrrolo[2,3-b:4,5-c']dipyridin-2-yl]-N-methylpyridine-2-carboxamide | 7.7 | |
| 44 | N,N-dimethyl-2-(1-methyl-1H-pyrazol-4-yl)-9H-pyrrolo[2,3-b:4,5-c']dipyridin-7-amine | 7.2 | |
| 45 | 2-(6-fluoropyridin-3-yl)-7-methyl-9H-pyrrolo[2,3-b:4,5-c']dipyridine | 7.4 | 1.1 |
| 46 | N-methyl-5-(7-methyl-9H-pyrrolo[2,3-b:4,5-c']dipyridin-2-yl)pyridine-2-carboxamide | 7.6 | |
| 47 | 7-methyl-2-(1-methyl-1H-pyrazol-4-yl)-9H-pyrrolo[2,3-b:4,5-c']dipyridine | 7.4 | 2.8 |
| 48 | 2-(6-fluoropyridin-3-yl)-7-(methoxymethyl)-9H-pyrrolo[2,3-b:4,5-c']dipyridine | 7.6 | |
| 49 | 5-[7-(methoxymethyl)-9H-pyrrolo[2,3-b:4,5-c']dipyridin-2-yl]-N-methylpyridine-2-carboxamide | 7.3 | |
| 50 | 7-(methoxymethyl)-2-(1-methyl-1H-pyrazol-4-yl)-9H-pyrrolo[2,3-b:4,5-c']dipyridine | 7.6 | 4.0 |
| 51 | 2-(1-methyl-1H-pyrazol-4-yl)-9H-pyrrolo[2,3-b:5,4-c']dipyridine | 7.6 | 4.5 |
| 52 | 2-(1H-pyrazol-4-yl)-9H-pyrrolo[2,3-b:5,4-c']dipyridine | 7.4 | 2.6 |
| 53 | N-methyl-5-(9H-pyrrolo[2,3-b:5,4-c']dipyridin-2-yl)pyridine-2-carboxamide | 7.5 | 1.5 |
| 54 | 2-(6-fluoropyridin-3-yl)-9H-pyrrolo[2,3-b:5,4-c']dipyridine | 7.6 | 1.9 |
| 55 | N-methyl-5-(9H-pyrrolo[2,3-b:5,4-c']dipyridin-2-yl)pyridin-2-amine | 7.8 | 0.5 |
| 56 | 2-(4-methoxy-1H-pyrazol-1-yl)-9H-pyrrolo[2,3-b:5,4-c']dipyridine | 7.5 | |
| 57 | 2-(6-fluoropyridin-3-yl)-9H-pyrrolo[2,3-b:5,4-b']dipyridine | 7.3 | 1.3 |
| 58 | 2-[4-(3-fluoropropyl)piperidin-1-yl]-9H-pyrrolo[2,3-b:5,4-b']dipyridine | 7.3 | |
| 59 | 7-(6-fluoropyridin-3-yl)-9H-pyrrolo[2,3-b:4,5-c']dipyridine | 7.3 | |
| 60 | N-methyl-5-(9H-pyrrolo[2,3-b:4,5-c']dipyridin-7-yl)pyridine-2-carboxamide | 7.6 | 0.5 |
| 61 | 7-(1-methyl-1H-pyrazol-4-yl)-9H-pyrrolo[2,3-b:4,5-c']dipyridine | 7.1 | |

TABLE 2

Rat MAO-A binding Results

| Example # | IUPAC_NAME | Rat MAO-A Binding INHIB 10 nM (%) | Rat MAO-A Binding INHIB 100 nM (%) |
|---|---|---|---|
| 4 | 2-(1-methyl-1H-pyrazol-4-yl)-9H-pyrrolo[2,3-b:4,5-c']dipyridine | 21 | 50 |
| 5 | 2-(6-methoxypyridin-3-yl)-9H-pyrrolo[2,3-b:4,5-c']dipyridine | 8 | 39 |
| 9 | 2-(1H-pyrazol-4-yl)-9H-pyrrolo[2,3-b:4,5-c']dipyridine | −5 | 7 |
| 11 | N-methyl-5-(9H-pyrrolo[2,3-b:4,5-c']dipyridin-2-yl)pyridine-2-carboxamide | −12 | −7 |

TABLE 2-continued

Rat MAO-A binding Results

| Example # | IUPAC_NAME | Rat MAO-A Binding INHIB 10 nM (%) | Rat MAO-A Binding INHIB 100 nM (%) |
|---|---|---|---|
| 12 | 3-fluoro-5-(9H-pyrrolo[2,3-b:4,5-c']dipyridin-2-yl)pyridin-2-amine | 8 | 13 |
| 22 | N-(2-methoxyethyl)-5-(9H-pyrrolo[2,3-b:4,5-c']dipyridin-2-yl)pyrimidin-2-amine | 8 | 15 |
| 24 | 2-(5-methyl-1H-pyrazol-3-yl)-9H-pyrrolo[2,3-b:4,5-c']dipyridine | 7 | 9 |
| 25 | 2-[1-(2-fluoroethyl)-1H-pyrazol-4-yl]-9H-pyrrolo[2,3-b:4,5-c']dipyridine | 13 | 2 |
| 29 | N-(2-fluoroethyl)-5-(9H-pyrrolo[2,3-b:4,5-c']dipyridin-2-yl)pyridine-2-carboxamide | 8 | 23 |
| 30 | N-(2-methoxyethyl)-5-(9H-pyrrolo[2,3-b:4,5-c']dipyridin-2-yl)pyridine-2-carboxamide | 2 | 9 |
| 31 | 2-(4-methoxy-1H-pyrazol-1-yl)-9H-pyrrolo[2,3-b:4,5-c']dipyridine | 16 | 39 |
| 32 | 2-[2-(morpholin-4-yl)-1,3-thiazol-5-yl]-9H-pyrrolo[2,3-b:4,5-c']dipyridine | 7 | 46 |
| 44 | N,N-dimethyl-2-(1-methyl-1H-pyrazol-4-yl)-9H-pyrrolo[2,3-b:4,5-c']dipyridin-7-amine | 2 | 9 |
| 46 | N-methyl-5-(7-methyl-9H-pyrrolo[2,3-b:4,5-c']dipyridin-2-yl)pyridine-2-carboxamide | 11 | 12 |
| 47 | 7-methyl-2-(1-methyl-1H-pyrazol-4-yl)-9H-pyrrolo[2,3-b:4,5-c']dipyridine | −1 | 10 |
| 49 | 5-[7-(methoxymethyl)-9H-pyrrolo[2,3-b:4,5-c']dipyridin-2-yl]-N-methylpyridine-2-carboxamide | −9 | −4 |
| 50 | 7-(methoxymethyl)-2-(1-methyl-1H-pyrazol-4-yl)-9H-pyrrolo[2,3-b:4,5-c']dipyridine | 1 | 7 |
| 51 | 2-(1-methyl-1H-pyrazol-4-yl)-9H-pyrrolo[2,3-b:5,4-c']dipyridine | 3 | 6 |
| 53 | N-methyl-5-(9H-pyrrolo[2,3-b:5,4-c']dipyridin-2-yl)pyridine-2-carboxamide | −10 | −13 |
| 54 | 2-(6-fluoropyridin-3-yl)-9H-pyrrolo[2,3-b:5,4-c']dipyridine | 10 | 12 |
| 55 | N-methyl-5-(9H-pyrrolo[2,3-b:5,4-c']dipyridin-2-yl)pyridin-2-amine | 6 | 9 |
| 57 | 2-(6-fluoropyridin-3-yl)-9H-pyrrolo[2,3-b:5,4-b']dipyridine | 1 | 8 |
| 60 | N-methyl-5-(9H-pyrrolo[2,3-b:4,5-c']dipyridin-7-yl)pyridine-2-carboxamide | −3 | −1 |

The invention claimed is:

1. A compound of general formula I-A, or a pharmaceutically acceptable acid addition salt, a racemic mixture or its corresponding enantiomer and/or optical isomers thereof,

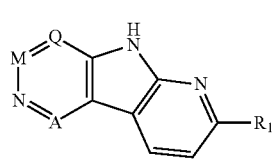

I-A wherein

R1 is pyrazole, thiazole, pyridine, or pyrimidine each of which is optionally substituted by one or two substituents independently selected from (1) fluorine; (2) methyl, ethyl or propyl, each of which is optionally substituted by fluorine or methoxy; (3) cyano; (4) amino optionally substituted by methyl or fluoro-ethyl; (5) —C(O)NHR1A where R1A is methyl, ethyl, or propyl, each of which is optionally substituted by fluorine or methoxy; (6) methoxy, ethoxy or propoxy, each of which is optionally substituted by fluorine or methoxy; or (7) morpholine, piperazine or piperidine, each of which is optionally substituted by fluorine or fluoromethyl;

M is C—R3, and Q is CH; or M is CH, and Q is CR3;

R3 is (1) H; (2) fluorine; (3) methyl, ethyl or propyl, each of which is optionally substituted by fluorine, hydroxy or methoxy; (4) methoxy, ethoxy or propoxy, each of which is optionally substituted by fluorine, hydroxyl or methoxy; (4) di-methyl-amino; or (5) —NHR3A where R3A is methyl, ethyl or propyl, each of which is optionally substituted by fluorine, hydroxy or methoxy; and wherein any hydrogen of formula I-A is H, $^2$H or $^3$H;

any carbon of formula I-A is C, $^{14}$C or $^{11}$C; and any fluorine of formula I-A is F or $^{18}$F;

provided that the compound of formula I is not a compound of general formula Ro I

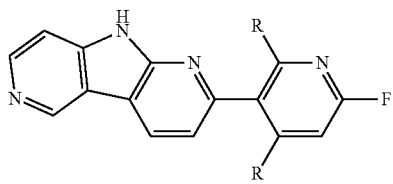

Ro I wherein
R is hydrogen or tritium;
F is fluoro or $^{18}$fluoro;
or a pharmaceutically acceptable acid addition salt thereof.

2. A pharmaceutical composition comprising a compound according to claim 1 and a pharmaceutically acceptable excipient.

3. A method of diagnosing or monitoring tau aggregates in the brain of a subject, the method comprising administering a radiolabeled compound containing an isotope according to claim 1 to the subject.

4. A method of treating a subject with a neurodegenerative disease in which tau aggregates in the brain are implicated, the method comprising administering to the subject an effective amount of compound according to claim 1.

* * * * *